(12) United States Patent
Davies et al.

(10) Patent No.: US 6,902,900 B2
(45) Date of Patent: Jun. 7, 2005

(54) NUCLEIC ACID PROBES AND METHODS TO DETECT AND/OR QUANTIFY NUCLEIC ACID ANALYTES

(75) Inventors: Martin Davies, Kent (GB); Ian Bruce, East Sussex (GB); Andreas Wolter, Esmarchstrasse (DE)

(73) Assignee: Prolico, LLC, Boulder, CO (US)

( * ) Notice: Subject to any disclaimer, the term of this patent is extended or adjusted under 35 U.S.C. 154(b) by 0 days.

(21) Appl. No.: 10/278,047

(22) Filed: Oct. 21, 2002

(65) Prior Publication Data

US 2003/0143591 A1 Jul. 31, 2003

Related U.S. Application Data

(60) Provisional application No. 60/336,432, filed on Oct. 19, 2001.

(51) Int. Cl.[7] ........................... C12Q 1/68; C07H 21/00; C07H 21/02; C07H 21/04; C09B 39/00
(52) U.S. Cl. ..................... 435/6; 536/23.1; 536/24.3; 536/24.32; 536/25.32; 536/25.33; 536/25.34; 534/727
(58) Field of Search .................. 536/23.1, 24.32, 536/25.32, 25.33, 25.34, 24.3, 24.33, 25.6, 25.3; 563/24.3; 534/727; 435/6, 91.1, 91.2

(56) References Cited

U.S. PATENT DOCUMENTS

| | | | |
|---|---|---|---|
| 5,210,015 A | 5/1993 | Gelfand et al. ............... | 435/6 |
| 5,998,135 A | 12/1999 | Rabbani et al. | |
| 6,251,600 B1 | 6/2001 | Winger et al. ............... | 435/6 |
| 2001/0014452 A1 | 8/2001 | Makino et al. ............... | 435/6 |
| 2002/0034754 A1 * | 3/2002 | Reed et al. ................... | 435/6 |

FOREIGN PATENT DOCUMENTS

| | | | |
|---|---|---|---|
| EP | 1215498 A1 | 6/2002 | |
| WO | WO 00/40751 | * | 7/2000 |

OTHER PUBLICATIONS

Sahoo et al. Pyrene Excimer Fluorescence: A spatially sensitive probe to monitor lipid–induced helical rearrangement of apolipophorin II. Biochemistry. vol. 39. pp. 6594–6601, 2000.*

Cardullo et al. (Dec. 1988) Proc. Natl. Acad. Sci. USA 85:8790–8794.

Espy et al. (Feb. 2000) J. Clin. Microbiol. 38:795–799.

Heid et al. (1996) Genome Research 6:986–994.

Higuchi et al. (Apr. 1992) Biotechnology 10:412–417.

Holland et al. (Aug. 1991) Proc. Natl. Acad. Sci. USA 88:7276–7280.

Marras et al. (1999) Genetic Analysis 14: 151–156.

Shinozuka et al. (1994) J. Chem. Soc., Chem. Comm. 1377–1378.

Tyagi and Kramer (Mar. 1996) Nat. Biotechnol. 14:303–308.

Whitcombe et al. (Aug. 1999) Nat. Biotechnol. 17:804–807.

Wittmer et al. (Jan. 1997) BioTechniques 22:130–138.

Masuko et al. *Nucleic Acid Research*, (2000), vol. 28, No. 8 pp. e34, i–viii.

* cited by examiner

*Primary Examiner*—Kenneth R. Horlick
*Assistant Examiner*—Cynthia Wilder
(74) *Attorney, Agent, or Firm*—Swanson & Bratschun, L.L.C.

(57) ABSTRACT

The invention comprises novel methods and strategies to detect and/or quantify nucleic acid analytes. The methods involve nucleic acid probes with covalently conjugated dyes, which are attached either at adjacent nucleotides or at the same nucleotide of the probe and novel linker molecules to attach the dyes to the probes. The nucleic acid probes generate a fluorescent signal upon hybridization to complementary nucleic acids based on the interaction of one of the attached dyes, which is either an intercalator or a DNA groove binder, with the formed double stranded DNA. The methods can be applied to a variety of applications including homogeneous assays, real-time PCR monitoring, transcription assays, expression analysis on nucleic acid microarrays and other microarray applications such as genotyping (SNP analysis). The methods further include pH-sensitive nucleic acid probes that provide switchable fluorescence signals that are triggered by a change in the pH of the medium.

25 Claims, 21 Drawing Sheets

Figure 20

NUCLEIC ACID PROBES AND METHODS TO DETECT AND/OR QUANTIFY NUCLEIC ACID ANALYTES

This application claims benefit of U.S. Provisional No. 60/336,432 filed Oct. 19, 2001.

FIELD OF INVENTION

The present invention relates to the field of molecular biology. More specifically, the present invention relates to the field of assays that utilize nucleic acid probes to detect and/or quantify nucleic acid analytes.

BACKGROUND OF THE INVENTION

Advances in DNA technology and sequencing, specifically the sequencing of whole genomes including the human genome, have resulted in a significantly increased need to detect and/or quantify specific nucleic acid sequences. Applications include the fields of in vitro diagnostics, including clinical diagnostics, research in the fields of molecular biology, high throughput drug screening, veterinary diagnostics, agricultural-genetics testing, environmental testing, food testing, industrial process monitoring and insurance testing. In vitro diagnostics and clinical diagnostics is related to the analysis of nucleic acid samples drawn from the body to detect the existence of a disease or condition, its stage of development and/or severity, and the patient's response to treatment. In high throughput drug screening and development nucleic acids are used similarly to other agents, such as, antigens, antibodies, receptors, etc, to analyze the response of biological systems upon exposure to libraries of compounds in a high sample number setting to identify drug leads. Veterinary diagnostics and agricultural genetics testing involve samples from a non-human animal or a plant species similar to in vitro diagnostics and to provide means of quality control for agricultural genetic products and processes. In environmental testing, organisms and their toxins that indicate the pollution of an environmental medium, e.g. soil, water, air, etc., are analyzed. Food testing includes the quantitation of organisms, e.g. bacteria, fungi, etc., as a means of quality control. In industrial process monitoring, nucleic acids are detected and/or quantified to indicate proper control of a production process and/or to generate a signal if such processes are out of control. In insurance testing organisms and/or their toxins are identified in screening tests to determine the risk category of a client or to help approve candidates. There are various other applications of the detection and/or quantitation of nucleic acids and new applications are being developed constantly.

The most common techniques to detect and measure nucleic acid analytes are based on the sequence-specific hybridization of the analyte with a complimentary nucleotide sequence probe which is marked with a detectable label, typically a fluorescent label, a radioactive label or another chemical label that can be detected in a secondary reaction. The probe is combined with the nucleic acid analyte, either in situ as part of a biological system or as isolated DNA or RNA fragments. The hybridization conditions are those that allow the probe to form a specific hybrid with the analyte, while not becoming bound to non-complementary nucleic acid molecules. The analyte can be either free in solution or immobilized on a solid substrate. The probe's detectable label provides a means for determining whether hybridization has occurred and thus, for detecting the nucleic acid analyte. The signal that is generated via the detectable sample can in some instances be measured quantitatively to back-calculate the quantity and the concentration of the analyte.

Current methods used to detect and measure nucleic acid analytes are briefly described below.

PCR Methods

The polymerase chain reaction (PCR) amplification of nucleic acids is regularly performed using fluorescently labeled oligonucleotide primers to produce an amplified DNA product that can be detected and quantified absolutely. A wide range of fluorochromes are now commercially available with spectral characteristics ($\lambda_{max}$ excitation and $\lambda_{max}$ emission) covering the wavelength range 350 to 700 nm, and into the near infra-red region of the electromagnetic spectrum. Thus, simultaneous, multiple detection of labeled molecules can be performed on the same sample, for example, following 'multiplex' PCR amplification of several nucleic acid sequences using pairs of oligonucleotide primers labeled with different fluorophores. Each pair gives rise to a separate amplified product that can be unambiguously identified due to its fluorescent label.

FISH Methods

Fluorescent in situ hybridization (FISH) is an important tool for clinical diagnosis and gene mapping. Labeled nucleic acid probes are used with multiple, simultaneous fluorescent detection to locate specific nucleic acid sequences in cells and tissues, and with the number of fluorochromes available there is the potential to visualize several fluorescent signals relating to different genetic sequences within the same sample.

Nucleic Acid Microarrays

Microarrays of nucleic acids that are prepared by combinatorial chemistry methods provide a convenient means to assay multiple, up to tens of thousands, analytes simultaneously. Typically, microarrays are probed with fluorescently labeled nucleic acid species, for example, from a clinical sample, and the position of any hybridized, labeled nucleic acid identified using fluorescence microscopy. The position relates to a known nucleic acid sequence immobilized at that part of the microarray.

Fluorescence Energy-Transfer (FRET) Methods

FRET relies upon the interaction of a fluorescent donor dye and a fluorescent acceptor dye, both of which are attached to the same molecule. If the donor and acceptor dyes are in proximity to one another, the acceptor dye quenches the fluorescent signal of the donor dye upon excitation. However, when the two dyes are held apart from one another, the fluorescence of the donor dye can be detected.

Molecular Beacon Methods

Molecular beacons are nucleic acid probes that contain both a covalently attached fluorescent dye and a non-fluorescent quencher moiety. Molecular beacons allow the diagnostic detection of specific nucleic acid sequences through their structural characteristics. The probes possess hairpin-forming regions, and in the absence of a complementary nucleic acid strand, the fluorescent dye and the quencher are in close proximity to one another and quenching of the fluorescent signal results. When incubated with a target nucleic acid analyte that possesses a complementary sequence, the probe anneals to the target, such that the fluorescent dye and the probe are held apart from one another, and fluorescence can be detected signifying the presence of a particular nucleic acid sequence.

Preferably, methods to detect and/or quantify nucleic acid analytes are carried out as homogeneous assays, which require no separate analyte manipulation or post-assay processing. Classically, agarose gel electrophoresis, possibly followed by Southern-blot hybridization or enzyme-linked immunoassays was used to detect and quantitate nucleic acid. Maniatis et al. (1982) "Molecular Cloning: A Laboratory Manual," Cold Spring Harbor Laboratory Press, NY, which is incorporated herein by reference in its entirety. Such procedures, and other methods that similarly rely on end-point analysis are generally labor intensive, require several separate and distinct handling processes and skilled personnel, are relatively slow to produce a result, and are prone to contamination and false positives due to the open system. In comparison, the advantages of a homogeneous assay, which represents a fully enclosed homogenous real-time detection system, include a faster turn-around time, especially when using microvolumes, higher throughput, better options for automation and multi-parallel analysis, and the use of a fully enclosed test system, which reduces the likelihood of contamination.

Homogeneous assays are particularly desirable with PCR methods and other amplification methods, because the amplification and the detection of the nucleic acid analyte can be carried out in one step without any risk of cross-contamination, which is a severe problem with all methods that rely on extensive amplification, especially in high-throughput analysis labs.

Prior art homogeneous detection and quantification methods for nucleic acid analytes involve a variety of chemistries and formats, which are exemplified below. Each of these methods is associated with certain disadvantages that create a need for improved detection/quantification strategies.

Hydrolysis Probes

Hydrolysis probes are described in Holland and Gelfand (1991) Proc. Natl. Acad. Sci. USA 88:7376–80 and U.S. Pat. No. 5,210,015, each of which is incorporated herein by reference in its entirety. This method takes advantage of the 5'-exonuclease activity present in the thermostable Taq DNA polymerase enzyme used in PCR (TAQMAN™ probe technology, Perkin-Elmer Applied Biosystems, Foster City, Calif., USA) and is amplified to homogeneous detection in PCR, as described by Heid et al. (1996) Genome Methods 6:986–94, which is incorporated herein by reference in its entirety. This method involves the use of a nucleic acid probe is used which is labeled with a fluorescent detector dye and an acceptor dye. Typically, the 2 dyes are attached to the 5'- and 3'-termini of the probe and when the probe is intact, the fluorescence of the detector dye is quenched by fluorescence resonance energy transfer (FRET). The probe anneals downstream of the amplification target site on the template DNA in PCR reactions. Amplification is directed by standard primers upstream of the probe, using the polymerase activity of the Taq enzyme. FRET quenching continues until the Taq polymerase reaches the region where the labeled probe is annealed. Taq polymerase recognizes the probe-template hybrid as a substrate, hydrolyzing the 5' detector dye during primer-directed DNA amplification. The hydrolysis reaction releases the quenching effect of the quencher dye on the reporter dye, thus resulting in increasing detector fluorescence with each successive PCR cycle.

Mixed RNA/DNA sequence probes can also serve as hydrolysis probes to monitor PCR reactions, as described by Winger et al., U.S. Pat. No. 6,251,600 B1, which is hereby incorporated herein by reference in its entirety. The mixed RNA/DNA probes contain blocks of DNA nucleotides at either end of the probe and a stretch of RNA nucleotide sequence between the flanking DNA blocks. This type of probe also contains a detector and an acceptor dye, which are attached to the respective DNA blocks of the probe. Upon hybridization to a nucleic acid analyte, the resulting hybrid contains two stretches of DNA:DNA duplex structure, flanking a stretch of DNA:RNA duplex structure. In the presence of the enzyme RNAse H, the DNA:RNA duplex structure is subject to cleavage, because RNAse H specifically recognizes DNA:RNA duplexes and cleaves the RNA portion of these duplexes. As a result the two blocks of DNA nucleotide sequence of the probe are separated, which in turn results in an increased fluorescence of the detector dye, which is no longer quenched by the acceptor.

The efficiency of hydrolysis probes in homogeneous assays is generally limited by their inherent fluorescence background, which is caused by incomplete quenching. Fluorescence quenching in these probes is caused by fluorescence energy transfer (FRET), which decreases with the inverse sixth power of the distance between the donor and the acceptor. Since the two dyes of the FRET pair are not in close molecular proximity, the quenching in hydrolysis probes is inherently incomplete resulting in an observable fluorescence background and therefore in a low signal to noise ratio. Additionally, the efficiency of hydrolysis probes is highly dependent on the purity of the probes, because contamination with singly labeled probes results in unquenched fluorescence and therefore a high background.

Hairpin Probes

Hairpin probes or molecular beacons are described by Tyagi et at. (1996) Nat. Biotechnol. 14:303–308, and are applied to homogeneous detection in PCR, as described by Marras et al. (1999) Genetic Analysis 14:151–156, each of which is incorporated herein by reference in its entirety. Molecular beacons are nucleic acid probes that are able to form a hairpin substructure due to the presence of two inverted repeat sequences. They carry covalently attached detector and quencher dyes at the end of both arms of the hairpin substructure of the probe. This design allows for self-complementary hybridization of the two inverted repeat sequences to form a stable, hairpin structure in the absence of a specific target. The detector and quencher dyes are in close proximity to one another in this conformation, which results in quenching of the detector fluorescence. The stretch of nucleotide sequence between the inverted repeat sequences of a molecular beacon is complementary to its target, thus directing specific probe-target hybridization, which results in efficient separation of the quencher dye from the detector dye with subsequent light emission. Thus, in the presence of a complementary target sequence, the hairpin structure is eliminated and the separated dye fluoresces. No overlap is required between the emission spectrum of the fluorophore and the absorption spectrum of the quencher. This allows for a wider range of fluorophores to be used in molecular beacons as compared with hydrolysis probes (TAQMAN™ probes). Hairpin probes are most commonly used as "free-floating" probes to detect amplicons as they are produced by standard PCR amplification, but can also be attached to one of the primers to act as a self-probing beacon as described by Whitcombe et al. (1999) Nat. Biotechnol. 17:804–807, which is incorporated herein by reference in its entirety.

Hairpin probes are particularly difficult to design because their successful application requires several design conditions to be fulfilled simultaneously. Firstly, the two inverted repeats of the hairpin structure must have complementary counterparts in the target nucleic acid, which in turn requires the presence of inverted repeats in the target as well, a condition that is not generally met. Secondly, the $T_m$ of the loop portion of the hairpin structure with a complementary nucleic acid sequence and the $T_m$ of the stem portion need to be carefully balanced with respect to the temperature of the assay to allow the specific unfolding of the hairpin probe in the presence of the target without unspecific unfolding. Improper design of hairpin probes results in high fluorescence background and therefore a low signal to noise ratio. The efficiency of hairpin probes is particularly sensitive to the purity of the probes, because even minimal amounts of singly labeled impurities result in a high background in the assay.

Hybridization Probes

Hybridization probe design entails the use of two sequence-specific nucleic acid probes, each labeled with a fluorescent dye, one dye being a donor dye, the other dye being an acceptor dye. Typically, the two probes are designed to hybridize to a nucleic acid analyte close to each other in a head-to-tail arrangement that brings the two dyes into close proximity. In this arrangement, as demonstrated by Cardullo et al. (1988) Proc. Natl. Acad. Sci. USA 85:8790–04, which is incorporated herein by reference in its entirety, the fluorescence of the acceptor dye is enhanced if the donor is excited due to the radiationless uptake of energy from the donor. This method is applicable to PCR reactions (LIGHTCYCLER™ PCR technology, Roche Diagnostics, Indianapolis, Ind., USA), as demonstrated by e.g. Espy et al. (2000) J. Clin. Microbiol. 38:795–799, which is incorporated herein by reference in its entirety. For use with the LIGHTCYCLER™ instrument of Roche Diagnostics the 3'-end of one probe is labeled with fluorescein as a donor and the 5'-end of the other probe can be labeled with LC Red 640 or LC Red 705 as an acceptor. Upon the occurrence of FRET between the donor and the acceptor, the fluorescence of the acceptor is detected. The transfer of fluorescent resonance energy only occurs when both probes hybridize to the target in very close proximity, the optimal distance being one to five intervening bases between probes. Hybridization probes are used in conjunction with standard primers to direct the PCR amplification.

Assays based on hybridization probes require the design of two oligonucleotide probes and their synthesis and purification, which adds cost and increases the complexity of assays. The use of two different probes in each analysis is particularly disadvantageous in high-throughput settings where a multitude of samples need to be analyzed due to the linear relationship of the number of involved probes and the number of analyses to be performed. Additionally, assays based on hybridization probes are more difficult to multiplex due to the presence of a higher number of probes, each of which could potentially generate artifacts, such as false positives in a multiplexed analysis.

Probeless Detection

Probeless detection of nucleic acids takes advantage of the affinity of certain dyes for double stranded DNA. Ideally, a dye that is suitable for a probeless detection displays low or no fluorescence at all when not bound to double stranded DNA, but a bright fluorescence when attached to the DNA. Thus, upon binding of the dye to DNA, a fluorescent signal is generated that indicates the presence of the DNA. The binding of the dye occurs in a non-covalent manner and is not specific for the sequences of the DNA analyte. The method is applicable to PCR reactions where the presence or absence of amplicons can be monitored as the PCR reactions progress. Examples of probeless detection strategies for PCR reactions are exemplified by Higuchi et al. (1992) Biotechnology 10:412–417 and Wittwer et al. (1997) BioTechniques 22:130–138, each which is incorporated herein by reference in its entirety. Probeless detection strategies also involve the use of covalently linked dye pairs, wherein one of the dyes is a fluorescent intercalator, as described by Makino et al., U.S. patent application Ser. No. 2001/0014452A1. In this technique, the fluorescence of the intercalator is quenched by the second dye, the efficiency of the quenching being dependent on the presence of double stranded DNA. Upon the interaction of the covalently linked dye pair with double stranded DNA the quenching becomes less efficient and a fluorescence signal can be detected.

Probeless detection and quantitation strategies are inherently disadvantageous due to their non-specific nature. In general, these methods detect any kind of double stranded DNA regardless of the presence or absence of specific sequences. Therefore, probeless detection methods are prone to generate "false positives," caused by e.g. the formation of primer dimers or non-specific amplification products in PCR reactions.

The detection of nucleic acid targets has also been described with a variety of other strategies that involve fluorescent detection. For example, Cardullo et al. (1998) Proc. Natl. Acad. Sci. USA 85:8790–04, describe the use of competitive hybridization probes, i.e. a pair of complementary oligodeoxynucleotides, each member of the pair being labeled with a covalently attached fluorescent dye at the 5'-terminus, which form a short stretch of double stranded DNA in the assay. The two dyes of the oligodeoxynucleotide pair form a FRET system in which the fluorescence of the donor dye is quenched while the oligodeoxynucleotides are hybridized to each other. In the presence of a target nucleic acid analyte, the probes competitively hybridize with the target, which separates the two components of the FRET system resulting in observable fluorescence of the donor component. This method suffers from the disadvantage of being dependent on a FRET mechanism with the associated high fluorescence background. In addition, two probes are required per assay, which increases the complexity and the cost of the assay.

None of the described fluorescence based methods combines the desired features of homogeneous methods to detect and/or quantify nucleic acid analytes, i.e. high specificity, low fluorescence background and therefore a high signal to noise ratio, ease of probe design without restrictions caused by the sequence of the target, and low complexity associated with low cost.

The instant invention includes novel fluorescence based methods to detect and/or quantify nucleic acid analytes and novel nucleic acid probes that combine the desired features of homogeneous assays. The methods and probes of this invention have significant advantages and do not suffer from the limitations inherent to the prior art methods and probes. The nucleic acid probes described in this invention carry a multitude of covalently attached dyes in close molecular proximity and therefore have a very low intrinsic fluorescence background. They are highly sequence specific and not limited by complex design criteria, as for example hairpin probes, and are applied as a single probe per assay. They can easily be adopted in homogeneous assays, in particular in PCR based assays, and provide the results of the assays in real time. They are amendable to multiplexing in such assays and can be used as primers of a PCR reaction, which further simplifies PCR based assays. The probes are also applicable in assays conducted on nucleic acid microarrays. Furthermore, in one embodiment of the invention the probes provide switchable labels that can be activated and deactivated by an adjustment of the pH of the assay.

Probes that carry two covalently attached dyes in close molecular proximity have been described by Shinozuka et al. (1994) J. Chem. Soc. Chem. Comm. 1377–1378, which is incorporated herein by reference in its entirety. However, the probes disclosed by Shinozuka display a high fluorescence that is reduced upon the interaction with a complementary nucleic acid target. These probes, despite their usefulness in general studies of nucleic acid association and hybridization, cannot be applied effectively in homogeneous assays because of their intrinsic high fluorescence. The probes of this invention have a very low intrinsic fluorescence and are therefore superior to the prior art probes.

SUMMARY OF THE INVENTION

The present invention includes novel methods for detecting nucleic acid analytes through their interactions with a nucleic acid probe. The nucleic acid probes of the invention are comprised of a nucleic acid that is derivatized with two or more non-identical covalently attached dyes, at least one of the dyes being a detector dye, which is fluorescent. The nucleic acid probes are further characterized in that the attached dyes are in close molecular proximity, as defined by being attached through linkers at either the same or at adjacent nucleotides of the nucleic acid probe. The methods provided by the invention are based on the specific interaction of one of the dyes of a nucleic acid probe with the analyte. The specific interaction of the dye with the analyte results in a change of fluorescence of the detector dye which can be measured to detect or quantify the analyte.

In the preferred embodiments of the invention the nucleic acid probes, as defined herein, are comprised of the following combinations of covalent dyes:

I) a fluorescent intercalator and a non-fluorescent quencher;

II) a fluorescent intercalator and a donor dye of a FRET system;

III) a fluorescent intercalator and an acceptor dye of a FRET system;

IV) an intercalator and two dyes forming an excimer pair;

V) an intercalator and two dyes forming an exciplex pair;

VI) a fluorescent groove binder and a non-fluorescent quencher;

VII) a fluorescent groove binder and a donor dye of a FRET system;

VIII) a fluorescent groove binder and an acceptor dye of a FRET system;

IX) a groove binder and two dyes forming an excimer pair; and

X) a groove binder and two dyes forming an exciplex pair.

The probes described herein generally provide low fluorescent backgrounds, display enhanced binding affinities to complementary nucleic acid analytes, do not rely on changes in their secondary structure upon hybridization and do not require secondary reactions, such as enzymatic reactions, to generate a fluorescent signal.

In other embodiments, the present invention discloses novel synthetic methods to covalently attach multiple dyes to nucleic acids via multi-functional linker molecules. In addition "universal" quencher molecules are introduced to attach two dyes, typically a non-fluorescent quencher and a fluorescent intercalator, to nucleic acids.

The nucleic acid probes described herein are particularly useful in homogeneous assays, which do not require post-assay manipulations of the reagents and assay products, can be carried out in closed tubes to avoid cross-contamination, do not require particularly trained personnel to conduct the assays, and provide the analysis of samples in real time. The present invention includes applications for PCR reactions in order to provide the detection and/or quantification of PCR products in real time, and transcription assays that provide the analysis of mRNA transcripts in real time. Further applications of the novel nucleic acid probes include assays that are conducted on nucleic acid microarrays, in particular expression analysis and genotyping, especially the detection of single nucleotide polymorphisms on genomic DNA.

In yet another embodiment, the invention discloses nucleic acid probes comprised of a covalently attached pH-sensitive dye and second fluorescent dye in close molecular proximity. These probes are useful as pH sensitive probes and provide switchable labels that allow the fluorescent signal of an assay to be turned on and off depending on pH.

BRIEF DESCRIPTIONS OF THE DRAWINGS

Figure 4:
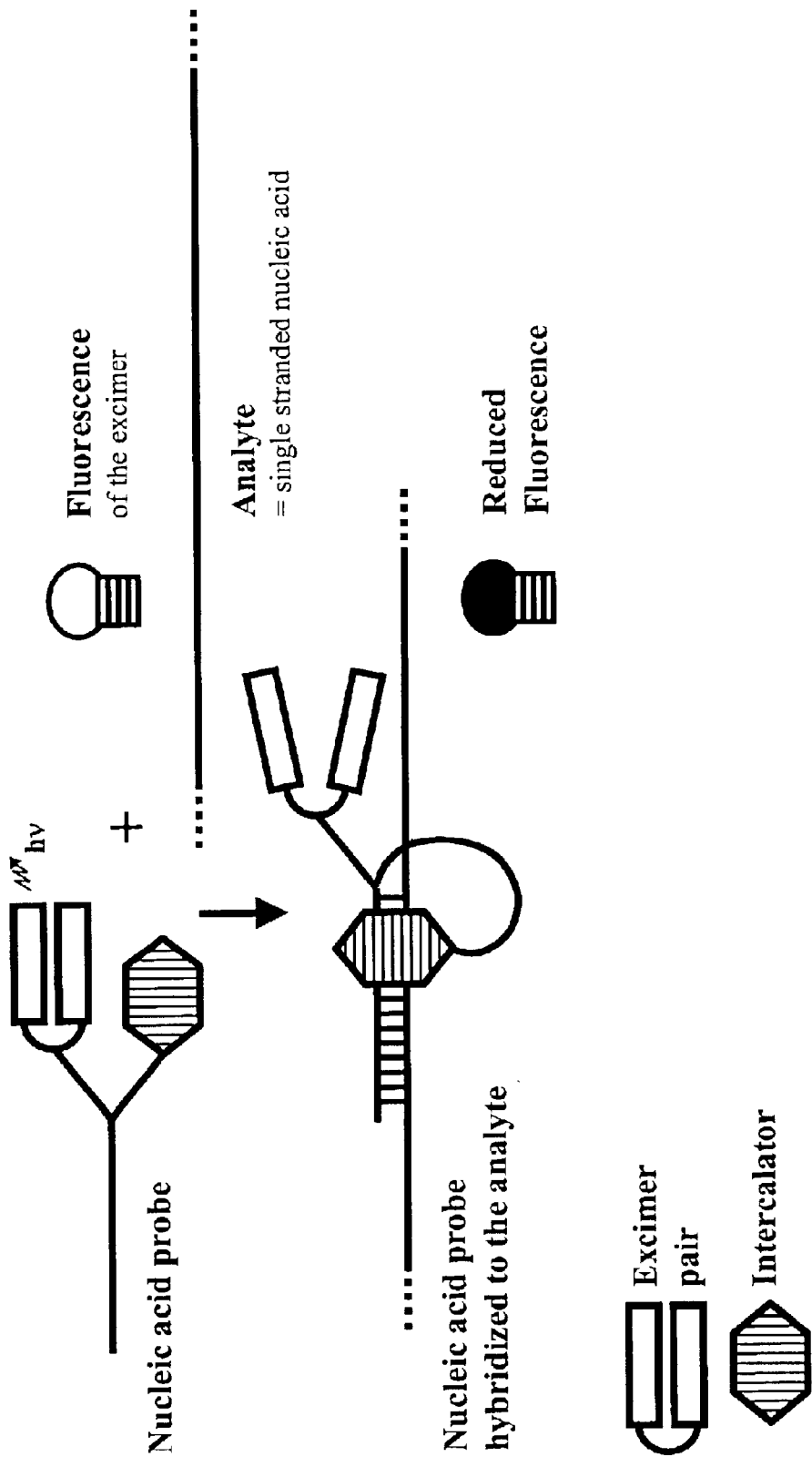

FIG. 4 is a schematic representation of a method for detecting and quantifying nucleic acid analytes employing specific nucleic acid probes, which carry an intercalator and two dyes forming an excimer pair (type IV nucleic acid probes). Upon hybridization of the probe and subsequent incorporation of the intercalator into the double stranded region the distance of the paired dyes increases leading to a reduced fluorescence.

Figure 5:
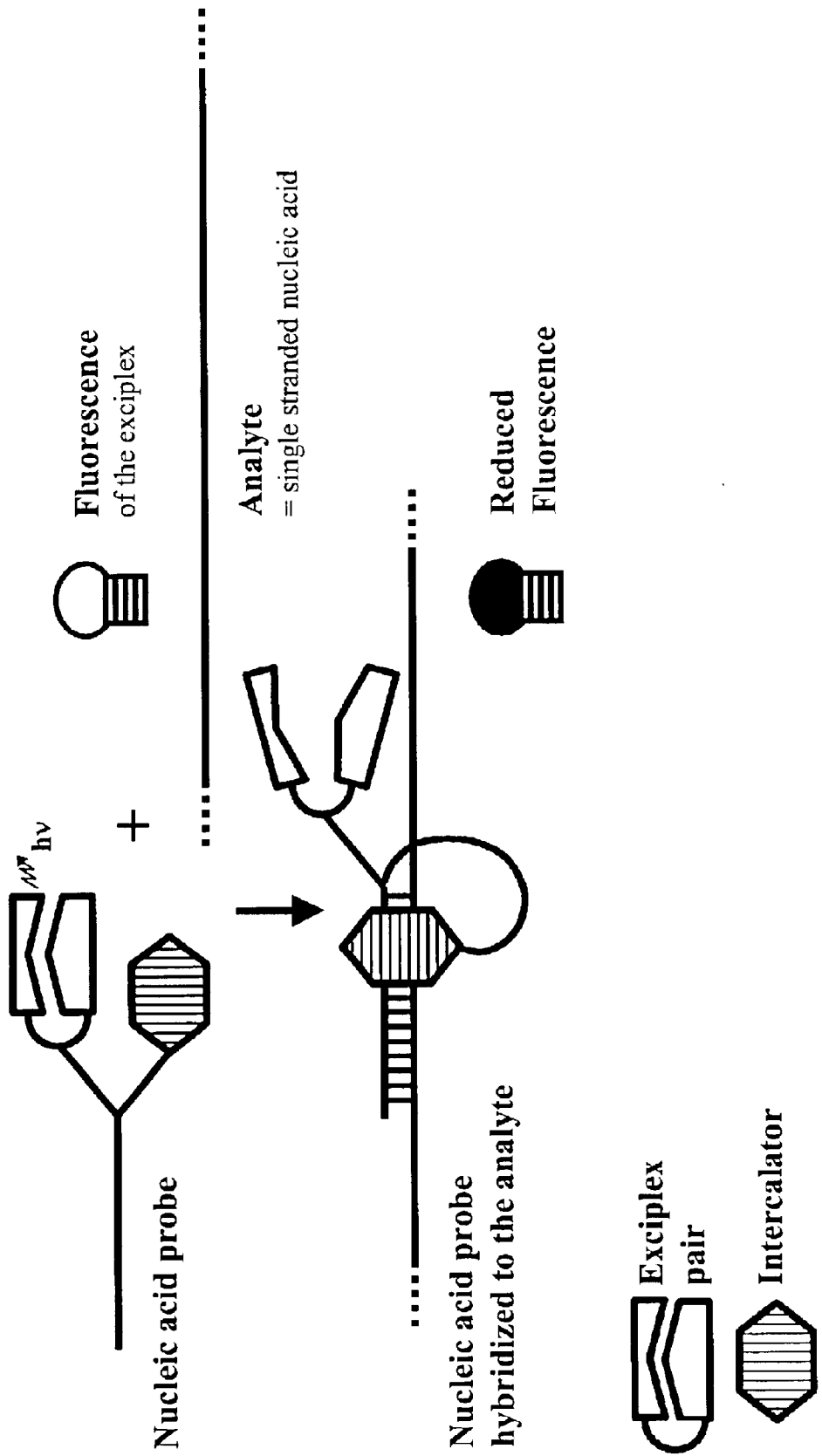

FIG. 5 is a schematic representation of a method for detecting and quantifying nucleic acid analytes employing specific nucleic acid probes, which carry an intercalator and two dyes forming an exciplex pair (type V nucleic acid probes). Upon hybridization of the probe and subsequent incorporation of the intercalator into the double stranded region the distance of the paired dyes increases leading to a reduced fluorescence.

Figure 6:
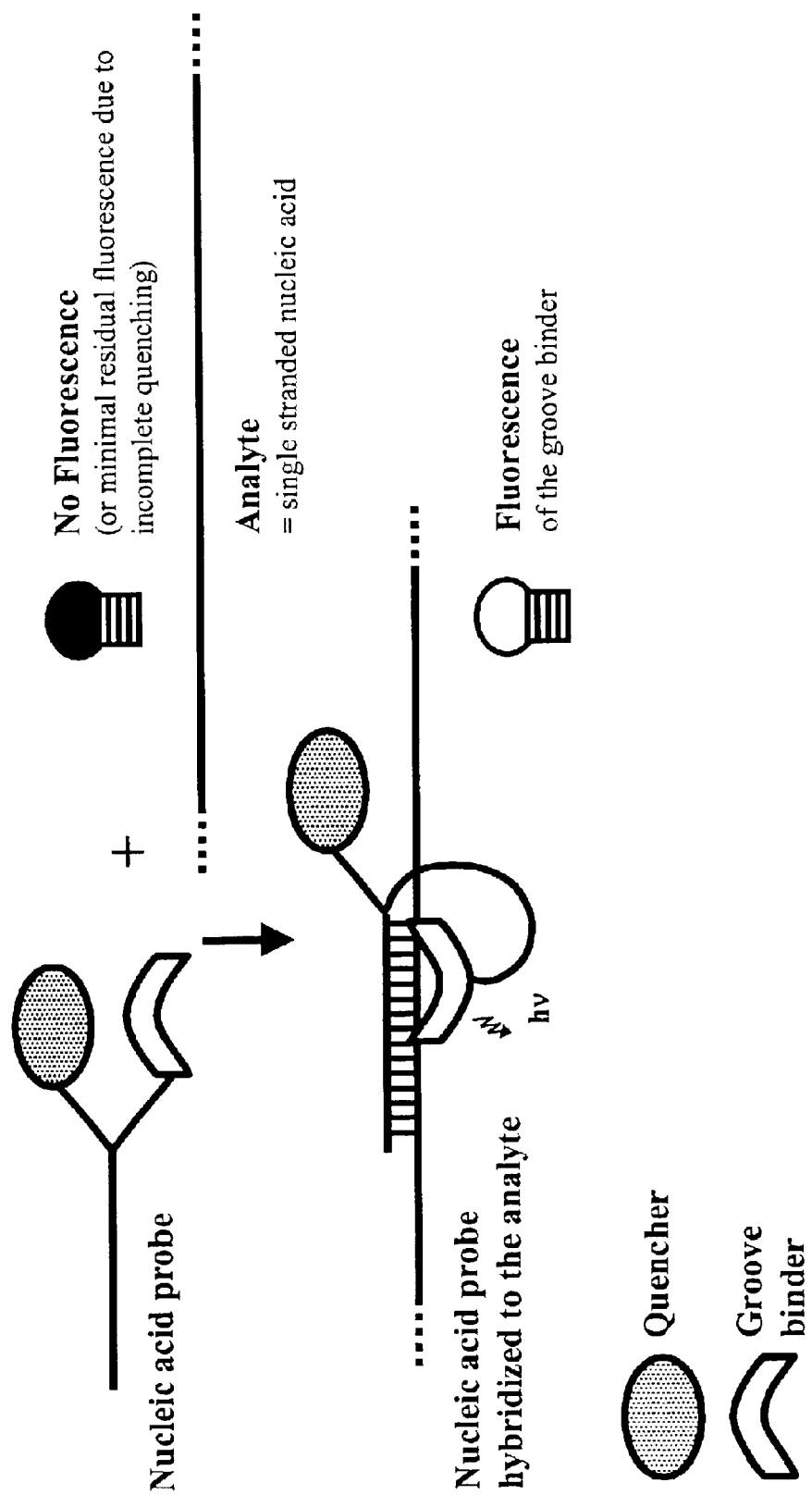

FIG. 6 depicts a schematic representation of a method for detecting and quantifying nucleic acid analytes employing specific nucleic acid probes, which carry both a groove binder serving as detector dye and a non-fluorescent quencher (type VI nucleic acid probes).

Figure 7:
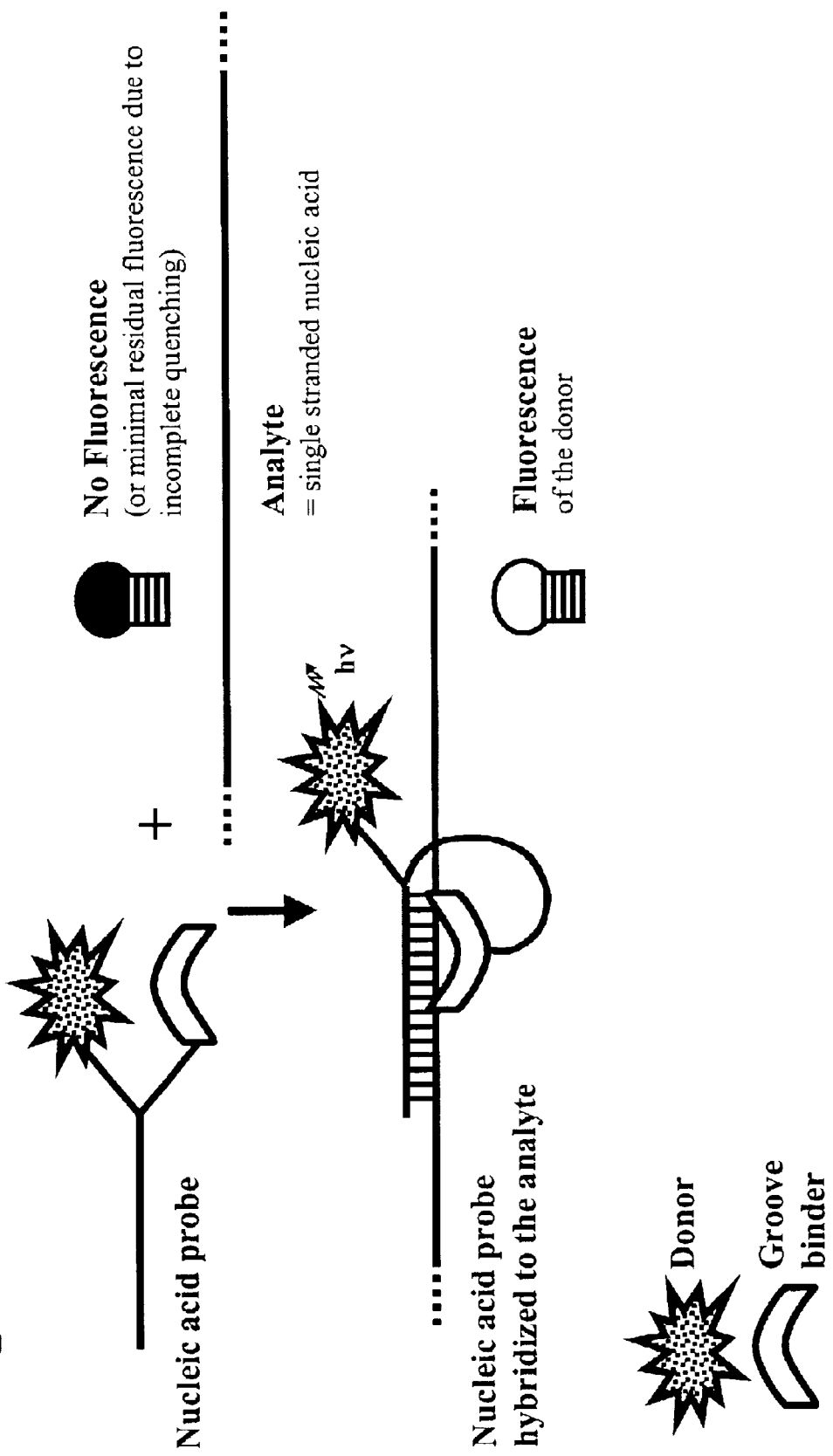

FIG. 7 depicts a schematic representation of a method for detecting and quantifying nucleic acid analytes employing specific nucleic acid probes, which are attached to a FRET system composed of a donor dye and a fluorescent groove binder serving as detector dye (type VII nucleic acid probes).

Figure 8:
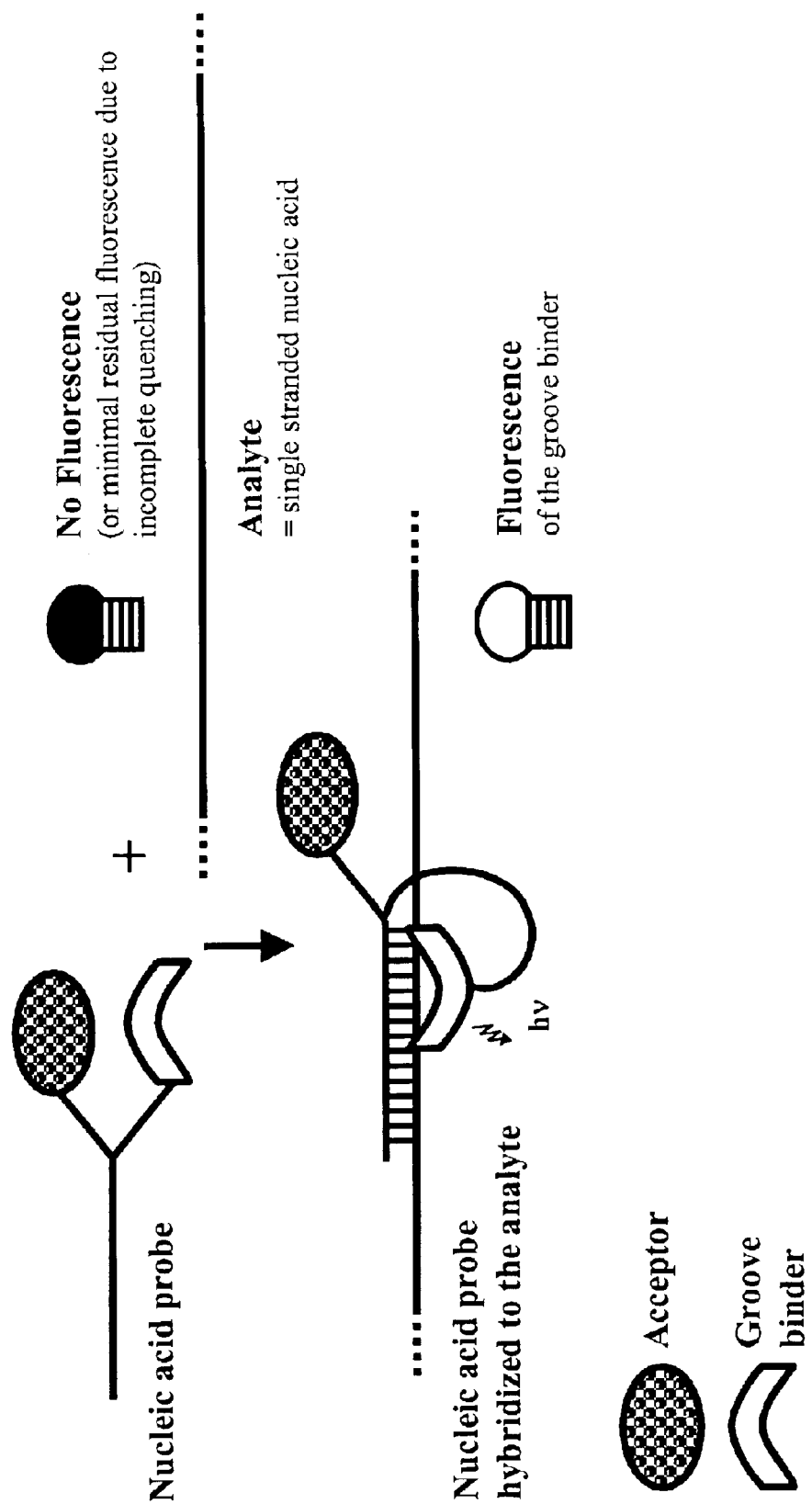

FIG. 8 depicts is a schematic representation of a method for detecting and quantifying nucleic acid analytes employing specific nucleic acid probes, which are attached to a FRET system composed of an acceptor dye and a fluorescent groove binder serving as detector dye (type VIII nucleic acid probes).

Figure 9:
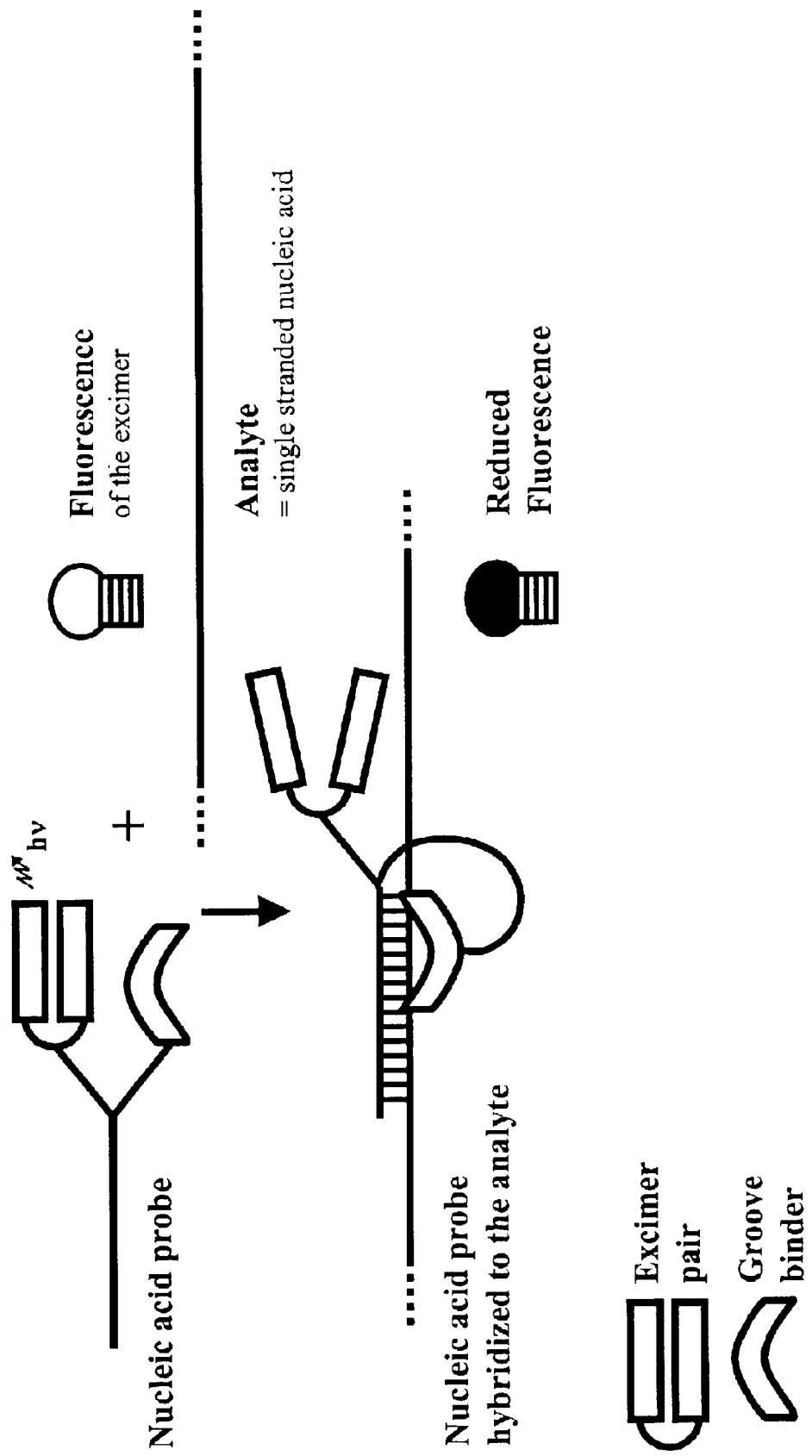

FIG. 9 is a schematic representation of a method for detecting and quantifying nucleic acid analytes employing specific nucleic acid probes, which carry a groove binder and two dyes forming an excimer pair (type IX nucleic acid probes). Upon hybridization of the probe and subsequent interaction of the groove binder with the double stranded region the distance of the paired dyes increases leading to a reduced fluorescence.

Figure 10:
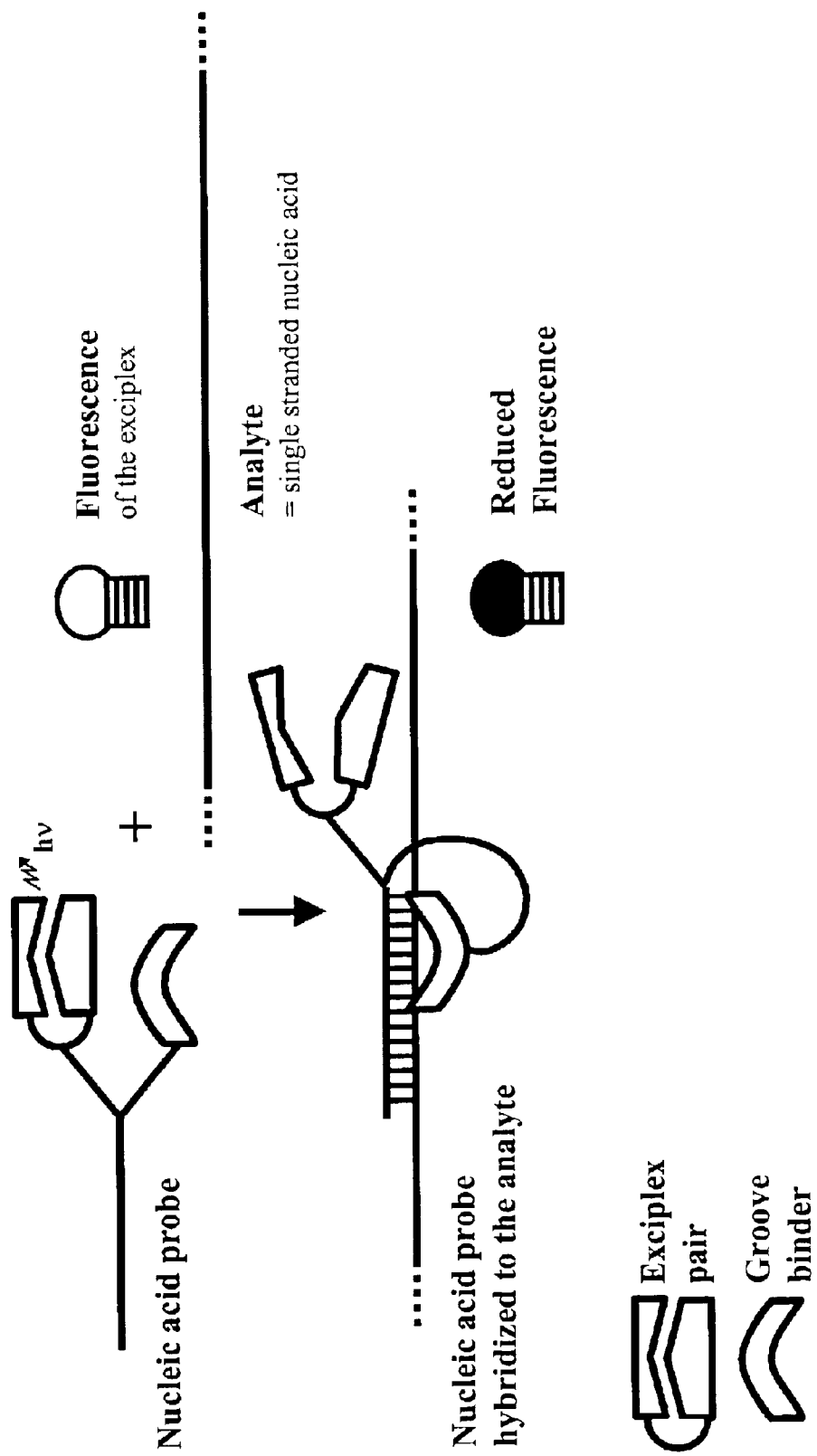

FIG. 10 is a schematic representation of a method for detecting and quantifying nucleic acid analytes employing specific nucleic acid probes, which carry a groove binder and two dyes forming an exciplex pair (type X nucleic acid probes). Upon hybridization of the probe and subsequent interaction of the groove binder with the double stranded region the distance of the paired dyes increases leading to a reduced fluorescence.

Figure 11:
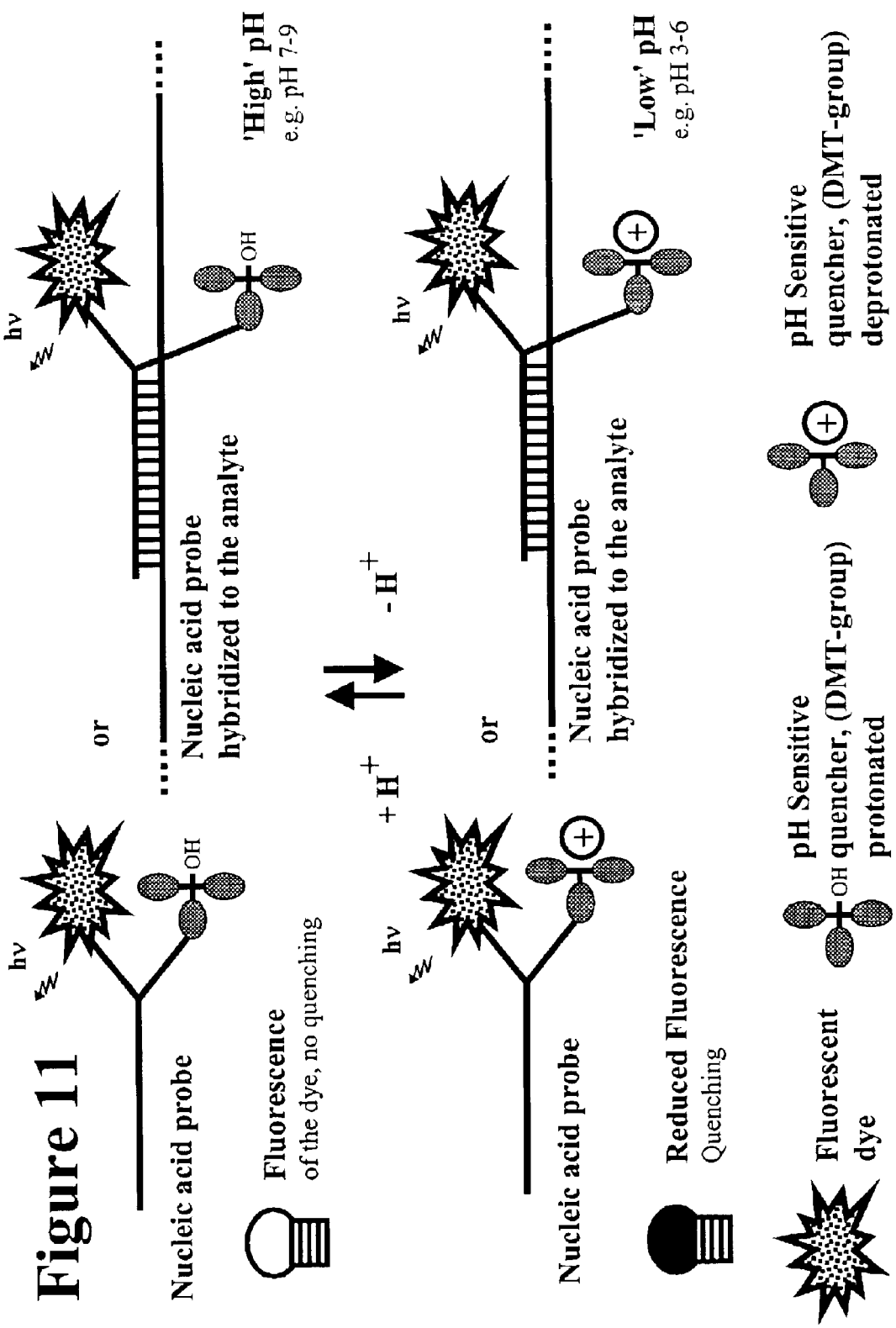

FIG. 11 is a schematic representation of the principle of nucleic acid probes that carry both a pH sensitive dye, which is represented as a trityl group, e.g. a DMT-group, and another fluorescent dye (type XI nucleic acid probes). At high pH, e.g. pH 7–9, the pH-sensitive trityl group exists in its protonated form and has essentially no absorbance. Under these conditions of pH the fluorescence of the second dye is observable. Upon a change in the pH towards more acidic conditions, e.g. pH 3–6, a trityl cation is formed that absorbs strongly at approximately 500 nm and the fluorescence of the second dye is efficiently quenched leading to a reduced fluorescence.

Figure 12:
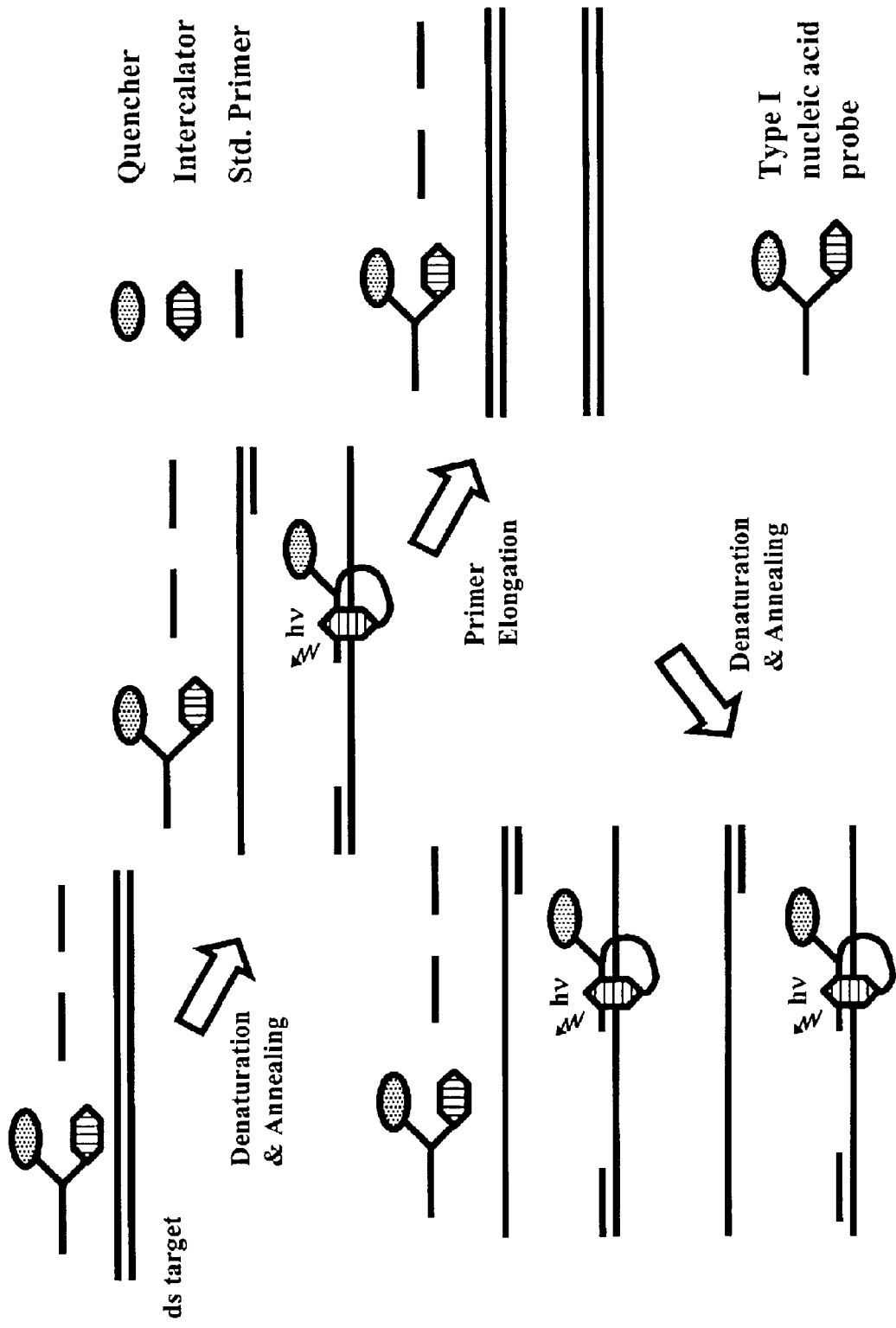

FIG. 12 is a schematic representation of a method for detecting and quantifying nucleic acid analytes employing specific nucleic acid probes, which carry an intercalator serving as detector dye and a non-fluorescent quencher (type I nucleic acid probes), in homogenous assays simultaneously with a PCR reaction. A fluorescence signal is generated in the annealing step of each cycle of the PCR that is proportional to the amount of amplicon formed in the reaction.

Figure 13:
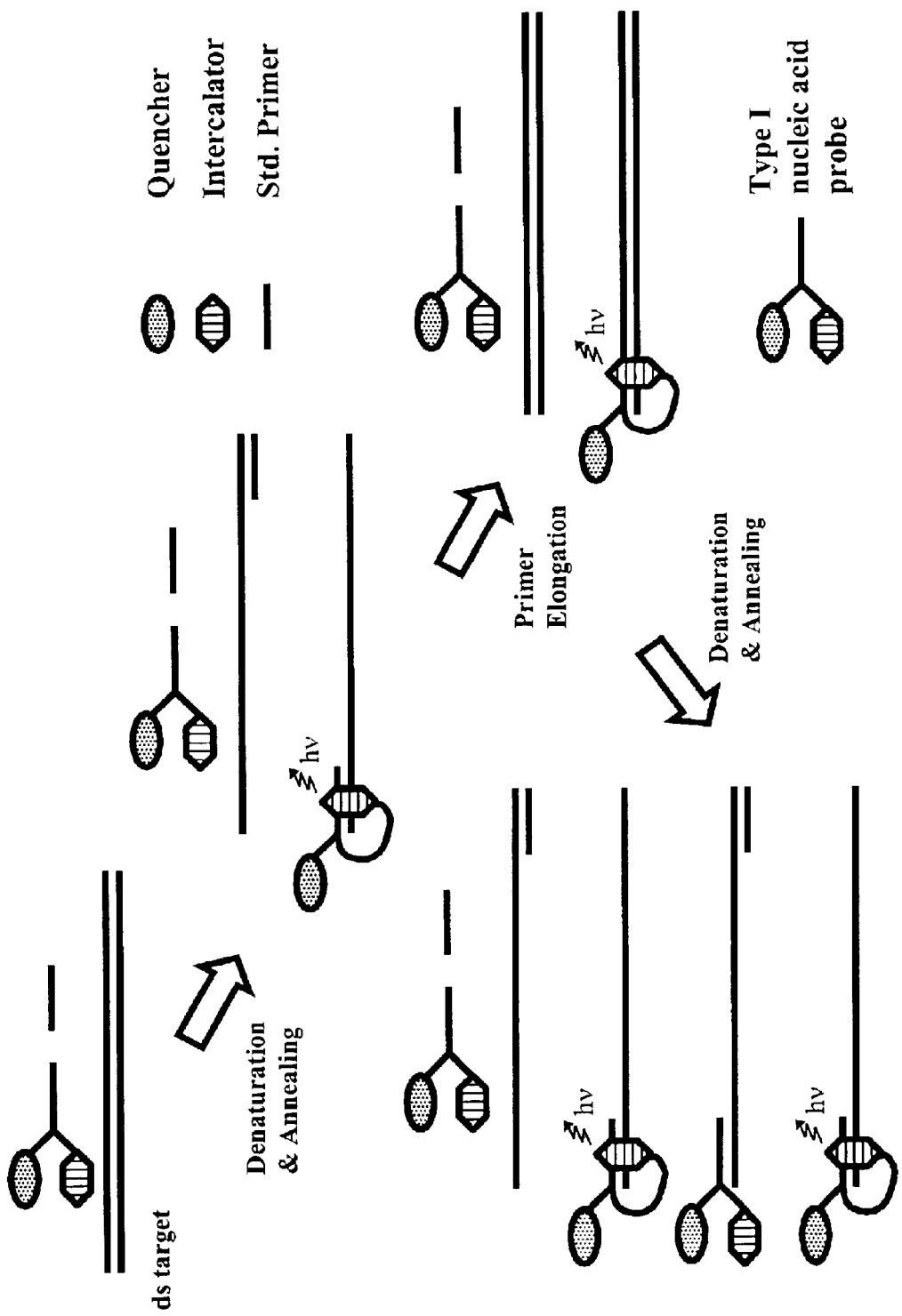

FIG. 13 is a schematic representation of a method for detecting and quantifying nucleic acid analytes employing specific nucleic acid probes, which carry an intercalator serving as detector dye and a non-fluorescent quencher (type I nucleic acid probes), as sequence specific primers of a PCR reaction in homogenous assays. A fluorescence signal is generated that is proportional to the amount of amplicon formed in the reaction.

Figure 14:
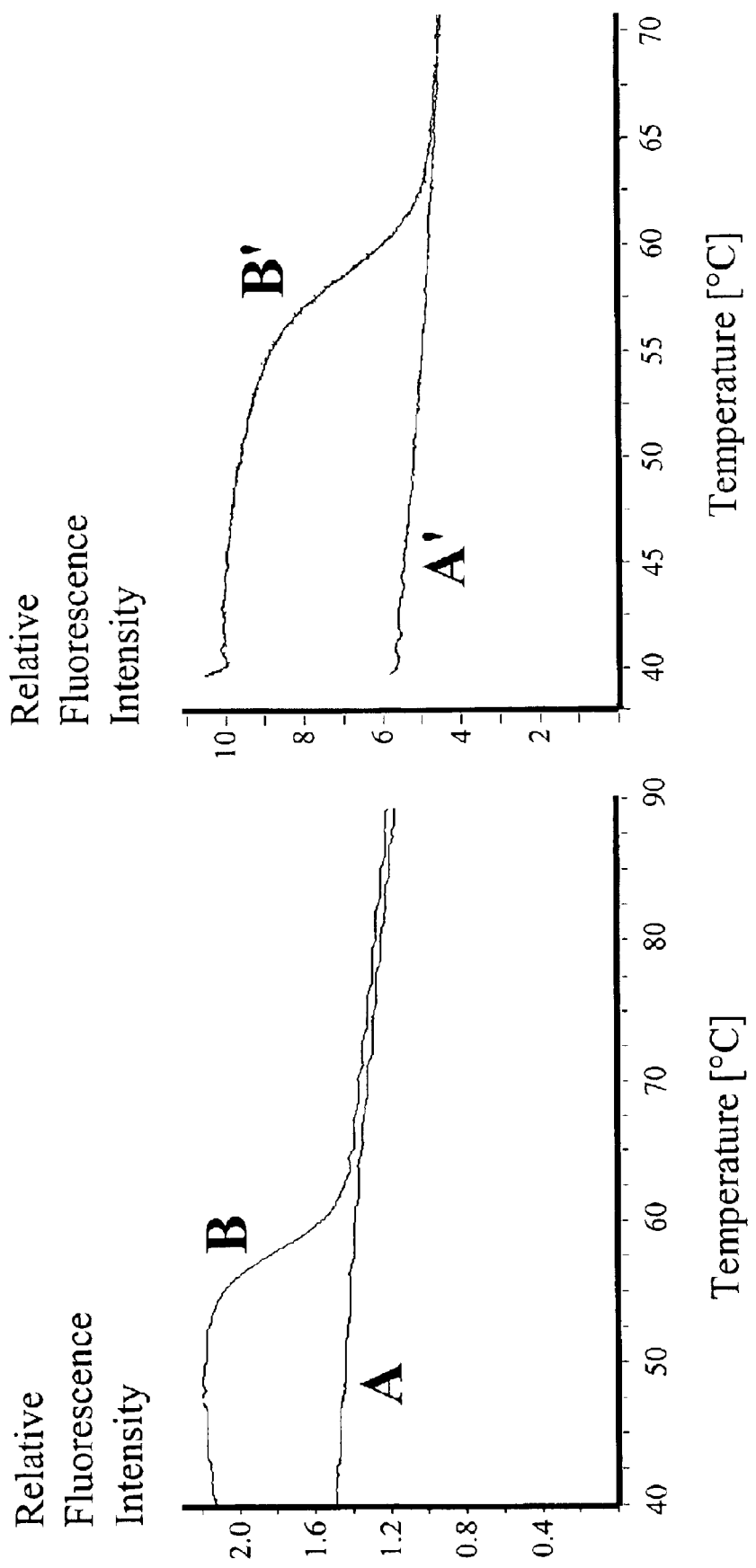

FIG. 14 displays the temperature dependence of the relative fluorescence intensity of nucleic acid probe (17.2) in the absence and in the presence of a complementary sequence monitored at emission wavelengths of 530 nm and 645 nm upon excitation at 470 nm, as described in Example 10.

Figure 15:
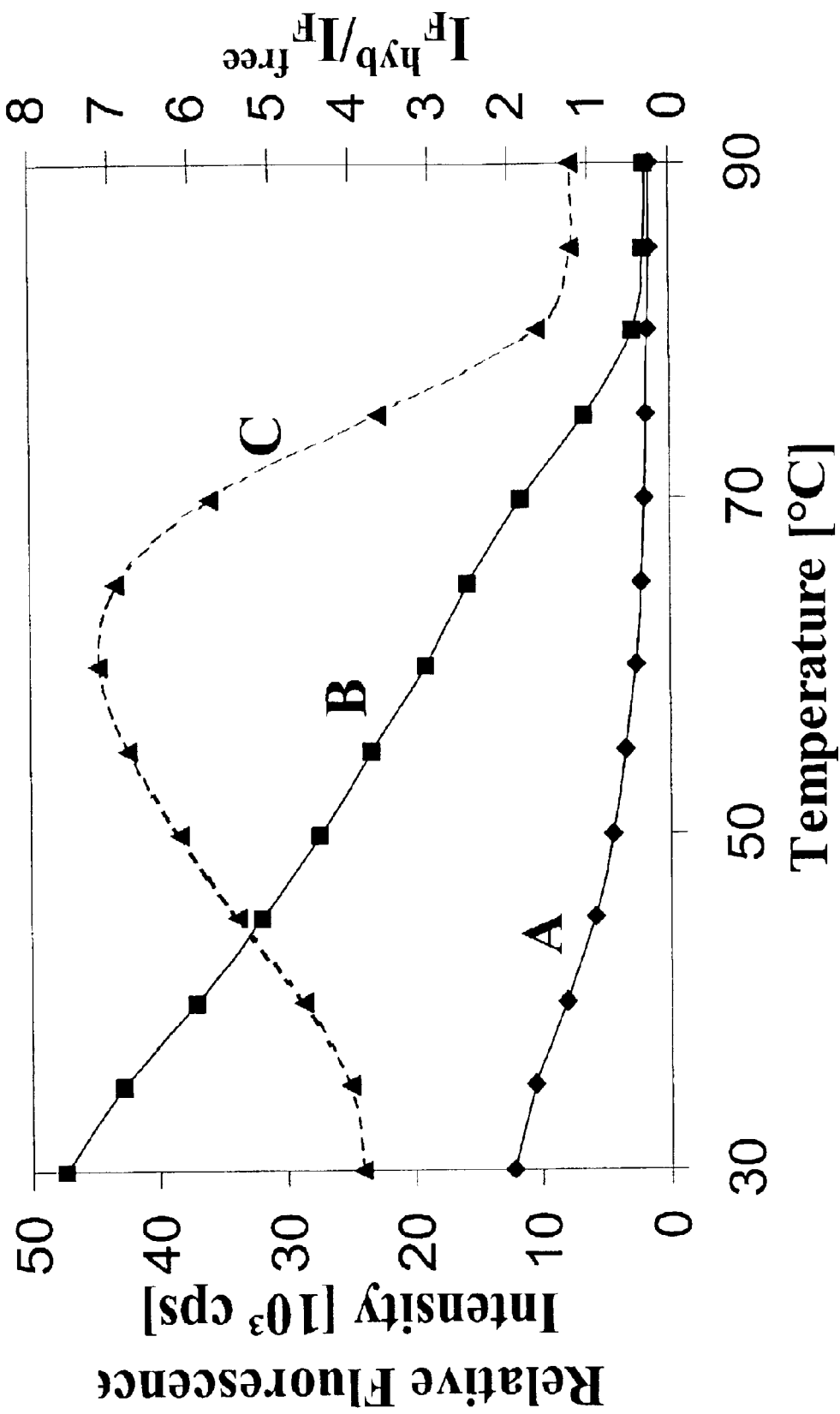

FIG. 15 displays the temperature dependence of the fluorescence intensity of the nucleic acid probe (17.11) in the absence and in the presence of a complementary sequence monitored at an emission wavelength of 528 nm upon excitation at 510 nm, as described in Example 11.

Figure 16:
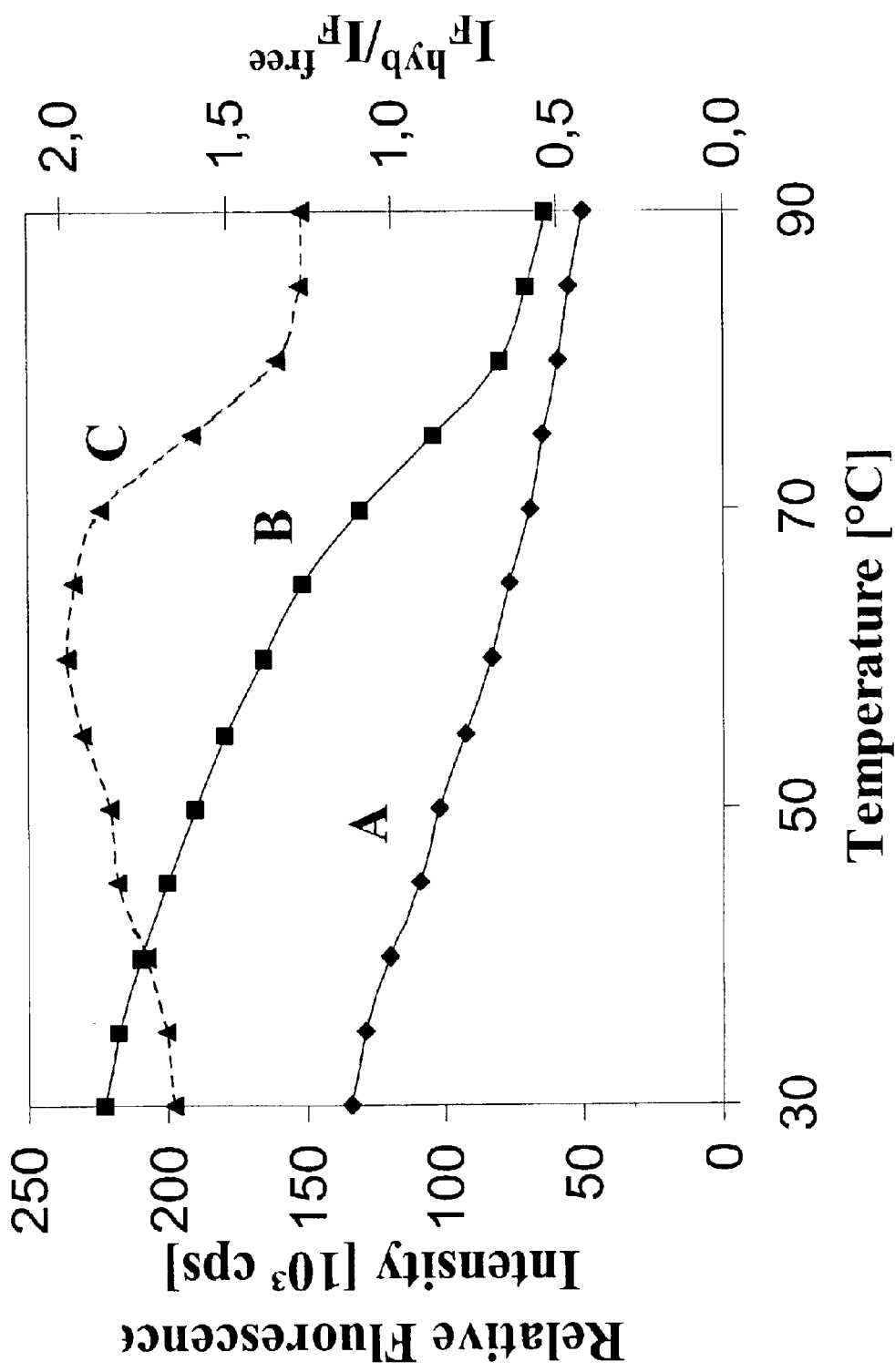

FIG. 16 displays the temperature dependence of the fluorescence intensity of the nucleic acid probe (17.20) in the absence and in the presence of a complementary sequence monitored at an emission wavelength of 625 nm upon excitation at 510 nm, as described in Example 11.

Figure 17:
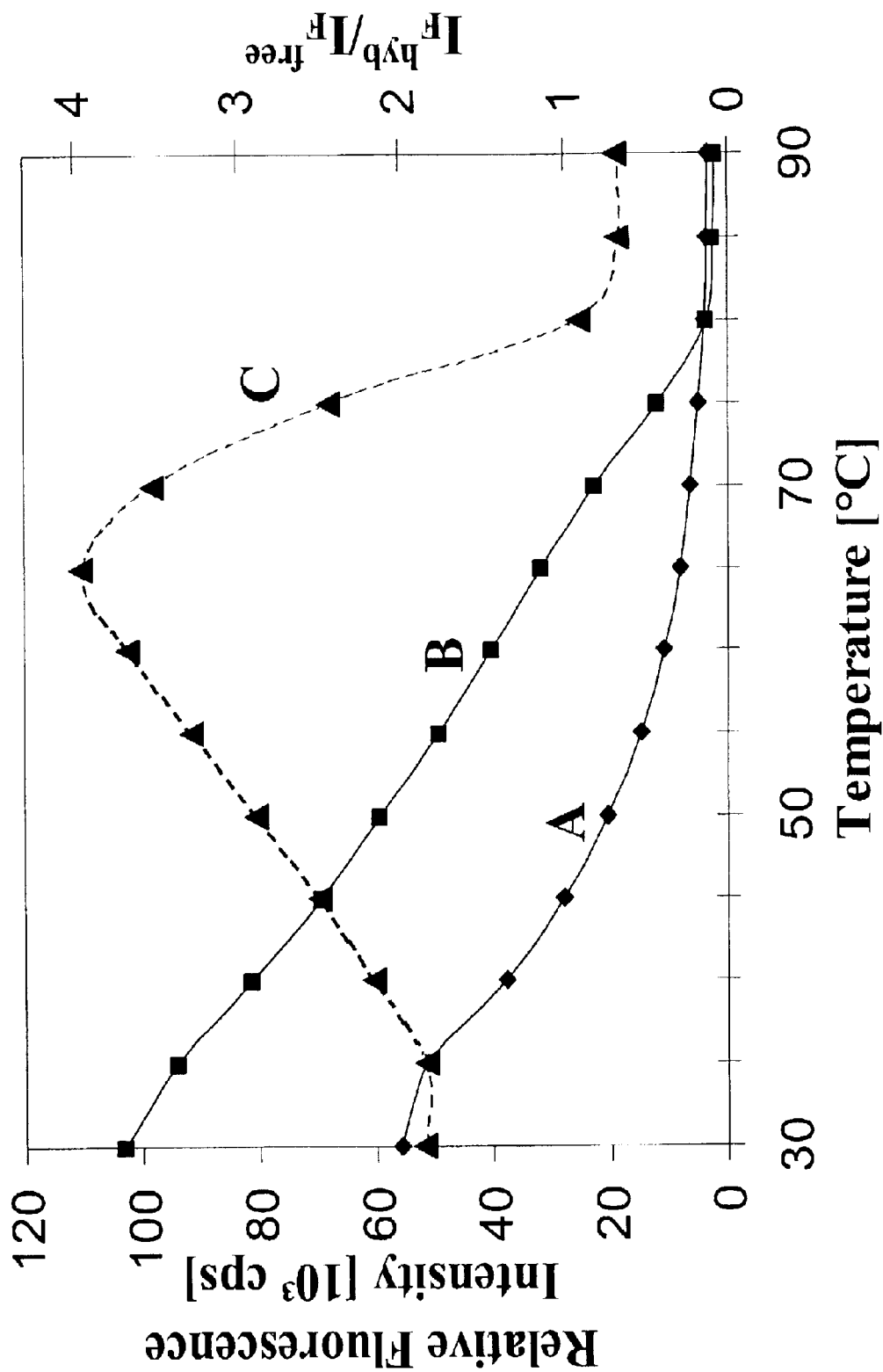

FIG. 17 displays the temperature dependence of the fluorescence intensity of the nucleic acid probe (17.21) in the absence and in the presence of a complementary sequence monitored at an emission wavelength of 528 nm upon excitation at 510 nm, as described in Example 11.

Figure 18:
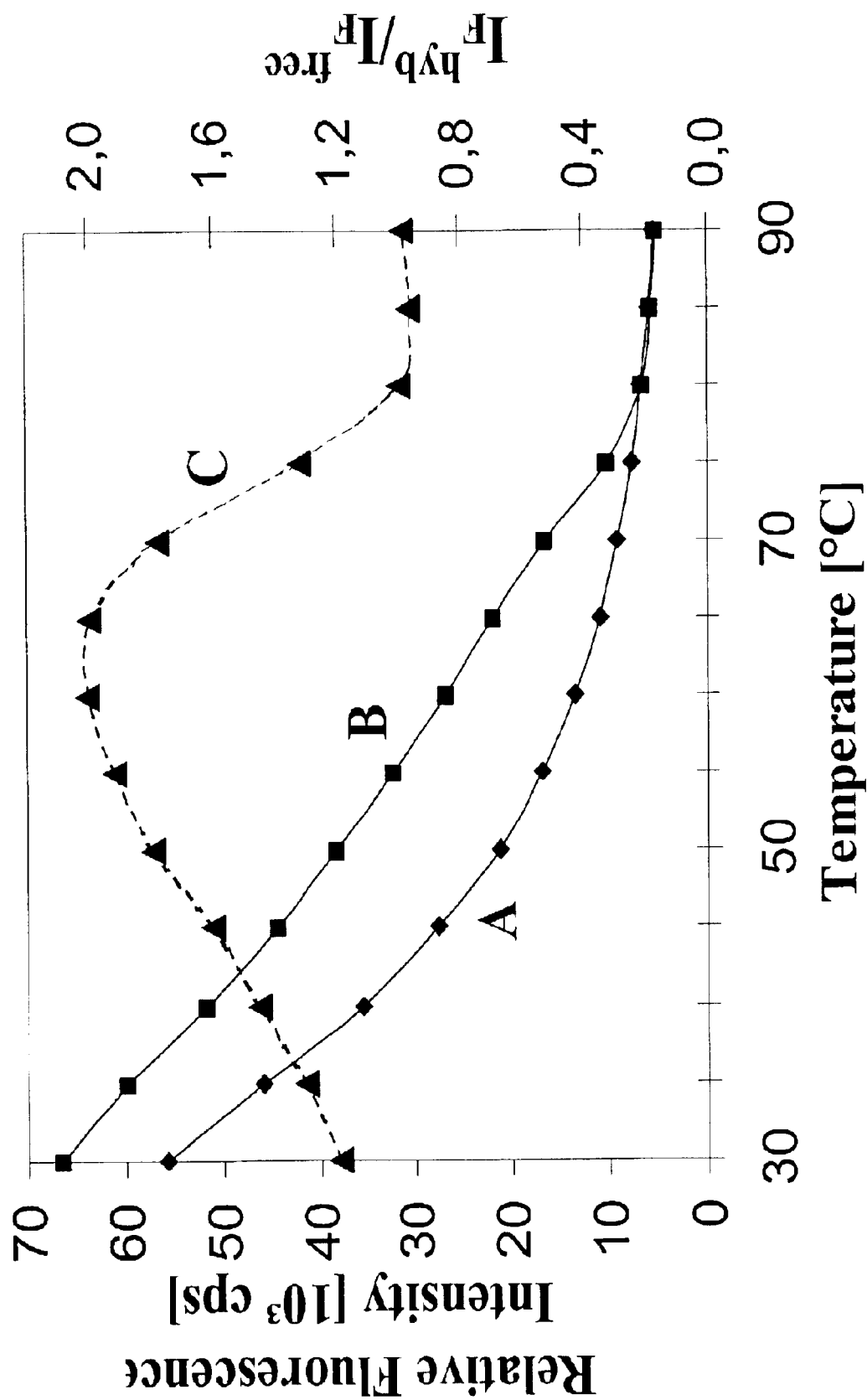

FIG. 18 displays the temperature dependence of the fluorescence intensity of the nucleic acid probe (17.21) in the absence and in the presence of a complementary sequence monitored at an emission wavelength of 528 nm upon excitation at 420 nm, as described in Example 11.

Figure 19:
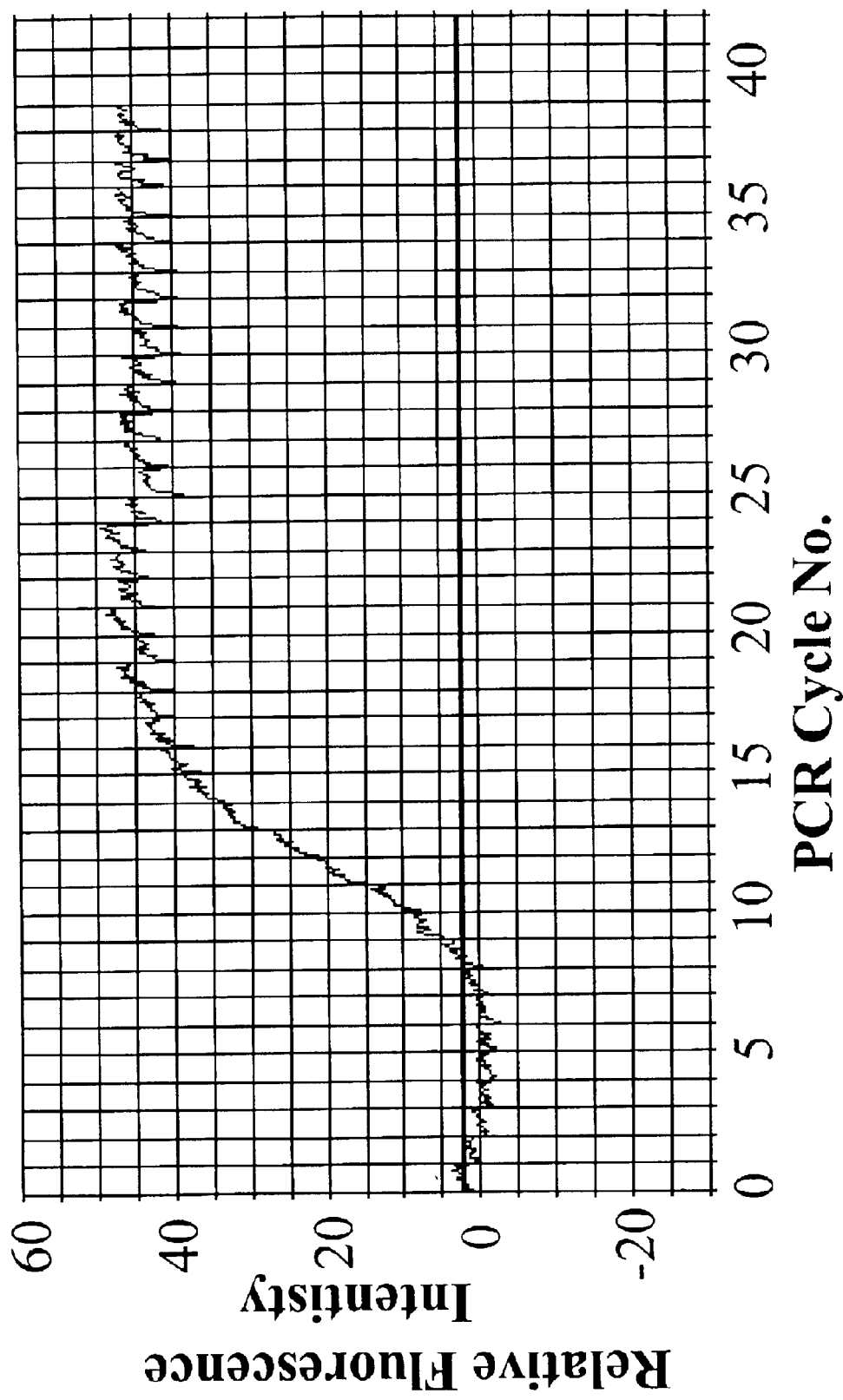

FIG. 19 displays the observed fluorescence in a real-time PCR experiment with the nucleic acid probe (17.21) and a target nucleic acid sequence related to the human adenine deaminase gene as a function of the PCR cycle number, as described in Example 14.

Figure 20:
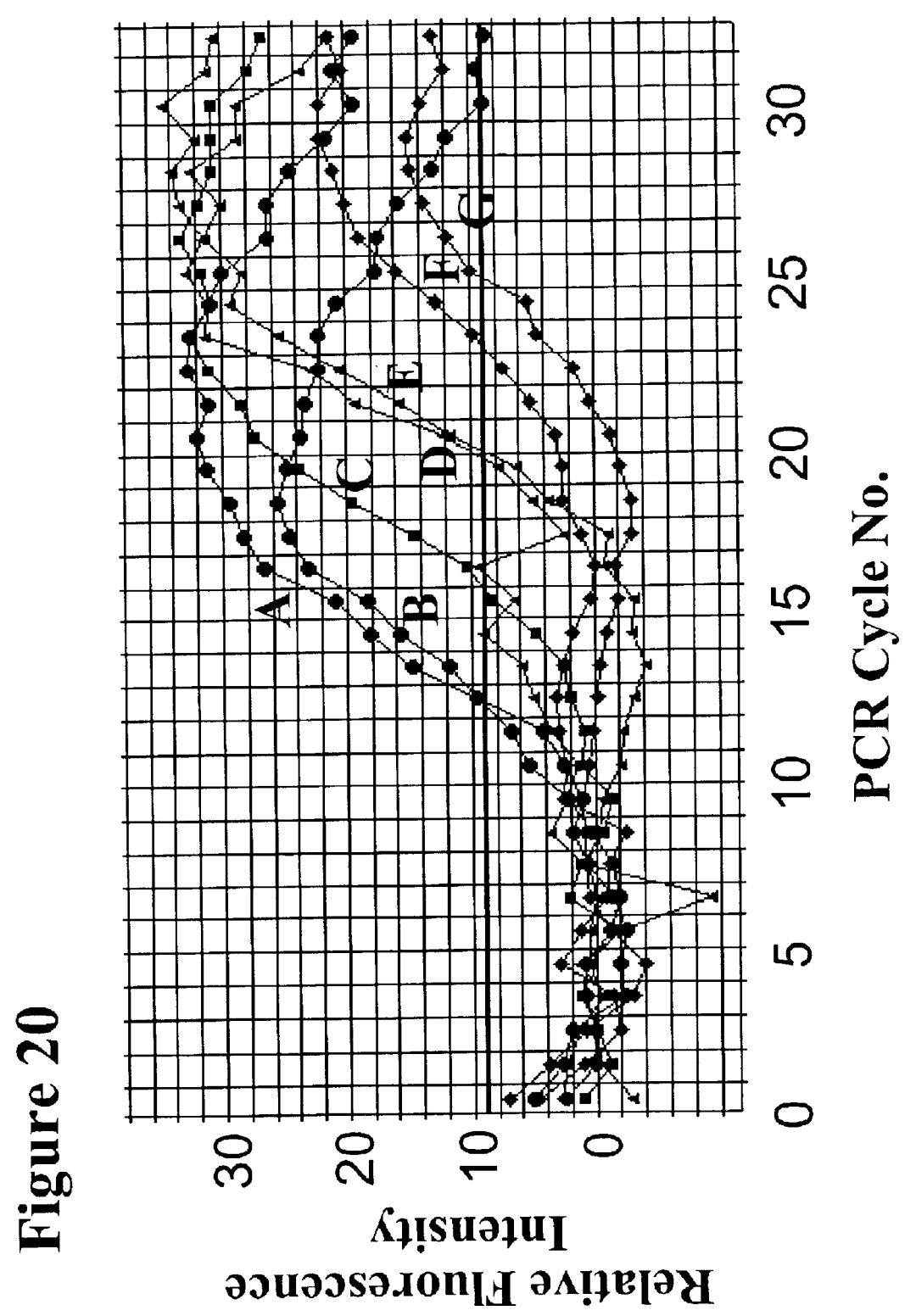

FIG. 20 displays the observed fluorescence in real-time PCR experiments with the nucleic acid probe (17.21) as a function of the PCR cycle number, wherein a serial dilution of the target nucleic acid is employed, as described in Example 15.

Figure 21:
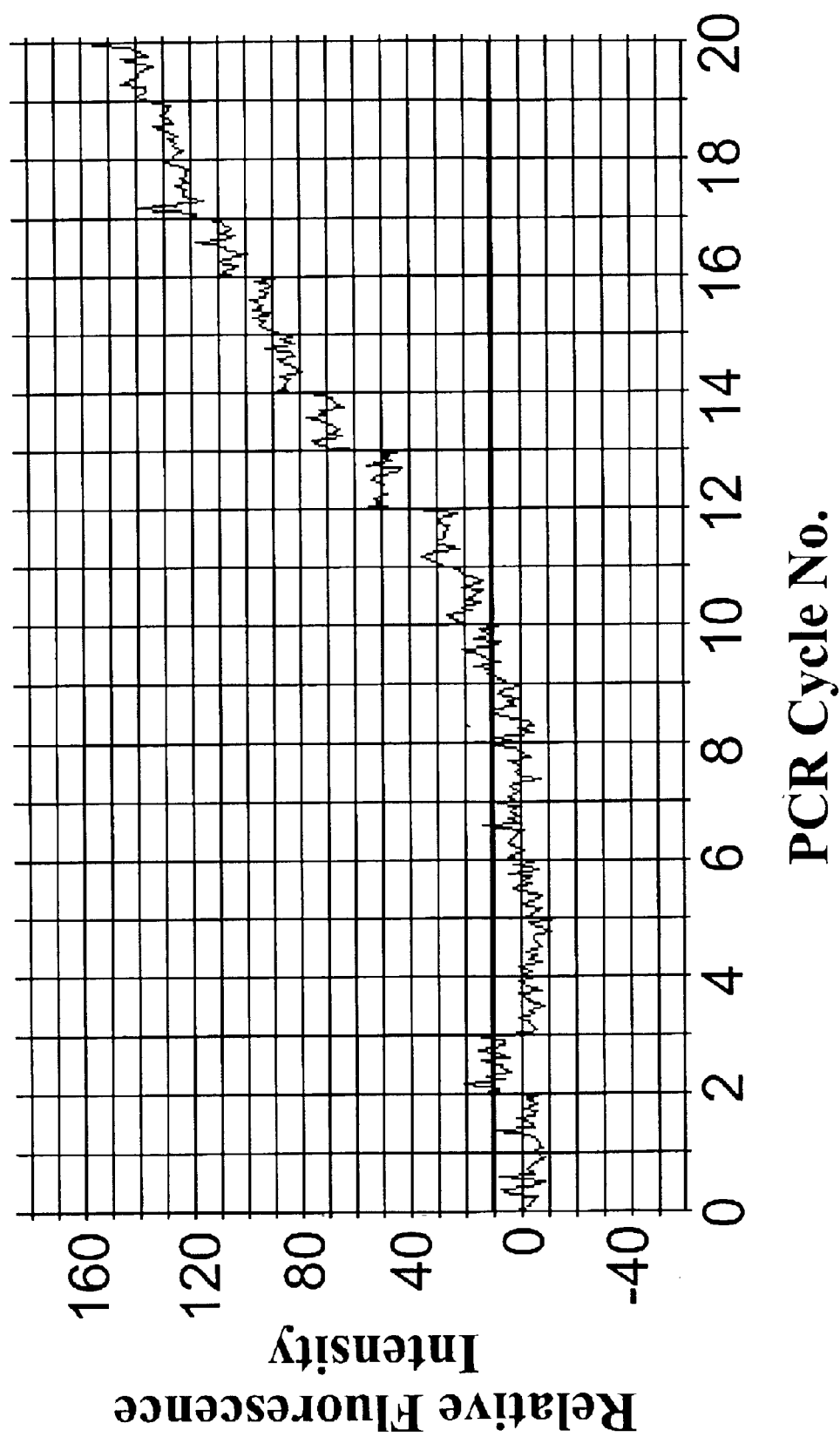

FIG. 21 displays the observed fluorescence in a real-time PCR experiment with the nucleic acid probe (17.21) and a target nucleic acid sequence related to the human prothrombin gene as a function of the PCR cycle number, as described in Example 14.

DETAILED DESCRIPTION OF THE INVENTION

The present invention includes novel methods for detecting nucleic acid analytes through their interactions with a nucleic acid probe. The nucleic acid probes of the invention are comprised of a nucleic acid that is derivatized with two or more non-identical covalently attached dyes, at least one of the dyes being a detector dye, which is fluorescent. The nucleic acid probes are further characterized in that the attached dyes are in close molecular proximity, as defined by being attached through linkers at either the same or at adjacent nucleotides of the nucleic acid probe. The methods provided by the invention are based on the specific interaction of one of the dyes of a nucleic acid probe with the analyte. The specific interaction of the dye with the analyte results in a change of fluorescence of the detector dye which can be measured to detect or quantify the analyte.

Various terms are used herein to refer to aspects of the present invention. To aid in the clarification of the description of the components of the invention, the following descriptions are provided.

It is to be noted that the term "a" or "an" entity refers to one or more of that entity; for example, a nucleic acid that carries a multitude of dyes refers to one or more nucleic acids that carry a multitude of dyes. As such, the terms "a" or "an," "one or more" and "at least one" are used interchangeably herein.

The term "analyte" refers to a nucleic acid molecule or a mixture of nucleic acid molecules, as defined below, that is to be detected or quantified using the method of this invention. The terms "target nucleic acid analyte" and "nucleic acid analyte" are used interchangeably with the term analyte in the context of this invention.

As used herein, "nucleic acid" means either DNA, RNA, single-stranded or double-stranded and any chemical modifications thereof, such as PNA and LNA. Nucleic acids can be of any size and are preferably oligonucleotides. Modifications include, but are not limited to, those that provide other chemical groups that incorporate additional charge, polarizability, hydrogen bonding, electrostatic interaction, and functionality to the individual nucleic acid bases or to the nucleic acid as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, unusual base-pairing combinations such as the isobases isocytidine and isoguanidine and the like. Modifications can also include 3' and 5' modifications such as capping. The nucleic acid can be derived from a completely chemical synthesis process, such as a solid phase mediated chemical synthesis, or from a biological origin, such as through isolation from almost any species that can provide DNA or RNA, or from processes that involve the manipulation of nucleic acids by molecular biology tools, such as DNA replication, PCR amplification, reverse transcription, or from a combination of those processes. Virtually any modification of the nucleic acid and nucleic acids of virtually any origin are contemplated by this invention.

"Covalently attached" in the context of this invention describes an attachment of one molecular moiety to another molecular moiety through covalent chemical bonds, i.e. chemical bonds that are established through the pairing of electrons from the atoms that are bonded together.

A "dye" in the context of this invention is any organic or inorganic molecule that absorbs electromagnetic radiation at a wavelength greater than or equal to 340 nm.

A "fluorescent dye" as defined herein is any dye that emits electromagnetic radiation of longer wavelength by a fluorescence mechanism upon irradiation by a source of electromagnetic radiation, including but not limited to a lamp, a photodiode or a laser.

A "linker" is defined herein as a molecular entity that covalently connects a dye to a nucleic acid. A linker can be of any chemical nature known to those skilled in the art. Typically, a linker contains functional groups that are attachment points that covalently connect the linker to the nucleic acid and the dye. Examples of functional groups that provide the attachment points include, but are not limited to, amino groups, thiol groups, carboxy groups, diene groups, dienophile groups, ester groups and phosphodiester groups, as well as, virtually any chemical functional groups that are known. A linker, aside from containing functional groups as attachment points for the nucleic acid and dyes, can consist of any chemical moiety that can carry at a minimum two functional groups to provide attachment points. Chemical moieties which are suitable as linker structures include, but are not limited to, linear, cyclic and branched structures and any combination thereof.

A "nucleic acid probe" as defined herein is a nucleic acid that carries a multitude of covalently attached dyes, with at least one of the dyes being fluorescent. Preferably, a nucleic acid probe contains two or three covalently attached dyes. Nucleic acid probes as defined herein are additionally characterized by a close molecular proximity of all attached dyes. A "close molecular proximity" in the context of the present invention means that the corresponding dyes are attached to the same nucleotide of the nucleic acid or to two adjacent nucleotides of the nucleic acid. The attachment of any dye to the nucleic acid consists of a linker as defined herein that is covalently attached to both the nucleic acid and the dye. The linker can connect one or more dyes to the nucleic acid.

A "detector dye" as defined herein is a fluorescent dye which is covalently attached to a nucleic acid probe as defined in this invention and which changes its fluorescent properties upon the interaction of the nucleic acid probe with an analyte.

An "intercalator" as defined herein is a dye which is covalently bound to a nucleic acid probe and which is capable of interacting with double stranded DNA by intercalation.

A "groove binder" as defined herein is a dye which is covalently bound to a nucleic acid probe and which is capable of interacting with double stranded DNA by binding to the minor groove or the major groove of the double stranded DNA.

A "quencher" as defined herein is a dye that reduces the emission of fluorescence of another dye. The reduction of fluorescence emission can be caused by a radiationless energy transfer through space (Fluorescence Resonance Energy Transfer (FRET)), see Yang et al. (1997) Methods Enzymol. 278:417–44, which is incorporated herein by reference in its entirety, or by the formation of ground state heterodimers, see Bernacchi et al. (2001) Nucleic Acids Res. 29:e62, which is incorporated herein by reference in its entirety, or by other mechanisms.

A "donor" as defined herein is a dye that is part of a FRET system in which the dye transfers energy to another dye by a radiationless process. Generally, in such a system the fluorescence of the dye decreases when it is part of a FRET system. FRET is described in detail in Yang et al. (1997) Methods Enzymol. 278:417–44.

An "acceptor" as defined herein is a dye that is part of a FRET system in which the dye accepts energy from another dye by a radiationless process. Generally, in such a system the fluorescence of the dye increases when excited at the wavelength of the corresponding donor of the FRET system when compared to the fluorescence of the dye when it is not part of a FRET system, see Yang et al. (1997) Methods Enzymol. 278:417–44.

An "excimer pair" as defined herein consists of a pair of identical dyes that form an excimer upon exposure to electromagnetic radiation. The dyes are covalently bound through a linker structure that ensures their close molecular proximity. The excimer formed by the excimer pair is fluorescent. An overview of excimers is provided in De Schryver et al. (1987) Acc. Chem. Res. 20:159–66 and Birks (1967) Nature 214:1187–90, each of which is incorporated herein by reference in its entirety.

An "exciplex pair" as defined herein consists of a pair of non-identical dyes that form an exciplex upon exposure to electromagnetic radiation. The dyes are covalently bound through a linker structure that ensures their close molecular proximity. The exciplex is fluorescent. Exciplexes are described by Birks (1967) Nature 214:1187–90.

A "pH sensitive dye" as defined herein is a dye that is covalently bound to a nucleic acid probe and which undergoes a change in its absorption properties upon a change of pH. The change of the absorption properties of the dye can be due to the protonation or the deprotonation of the dye and can encompass an enhancement of the dyes absorption or a decrease of the dyes absorption at a given wavelength.

A "homogeneous assay" as defined herein is a process to detect or quantify a nucleic acid analyte that requires no separate analyte manipulation or post-assay processing to record the result of the assay. Homogeneous assays are carried out in closed tubes, meaning that no further addition of reagents or supplementary chemicals is necessary to record the result once the assay is started. Homogeneous assays allow recordation of the result of the assay in real time, meaning that the result of the assay can be continuously recorded as the assay progresses in time.

The present invention includes the use of nucleic acid probes comprised of a number of covalently attached non-identical dyes in novel methods for the detection and quantitation of analytes. The nucleic acid probes are further characterized by a close molecular proximity of the dyes that are covalently attached to the nucleic acid.

In one embodiment, the present invention includes a method for the detection or quantification of a nucleic acid analyte comprising the steps of: (a) providing a nucleic acid probe, wherein said nucleic acid probe is comprised of a nucleic acid that is derivatized with two or more non-identical covalently attached dyes, wherein at least one dye is fluorescent, and wherein at least one dye has a high affinity to double stranded nucleic acids, wherein the dyes are attached at either the same or at adjacent nucleotides of the nucleic acid probe; (b) contacting said nucleic acid probe with a nucleic acid analyte so as to allow for the hybridization of the nucleic acid probe with the nucleic acid analyte; and (c) measuring the change in the fluorescence of the nucleic acid probe that occurs upon the hybridization of the nucleic acid probe with the nucleic acid analyte.

In preferred embodiments of the invention the nucleic acid probes, used in the method of this invention, are comprised of the following combinations of covalent dyes:

I) a fluorescent intercalator and a non-fluorescent quencher;

II) a fluorescent intercalator and a donor dye of a FRET system;

III) a fluorescent intercalator and an acceptor dye of a FRET system;

IV) an intercalator and two dyes forming an excimer pair;

V) an intercalator and two dyes forming an exciplex pair;

VI) a fluorescent groove binder and a non-fluorescent quencher;

VII) a fluorescent groove binder and a donor dye of a FRET system;

VIII) a fluorescent groove binder and an acceptor dye of a FRET system;

IX) a groove binder and two dyes forming an excimer pair; and

X) a groove binder and two dyes forming an exciplex pair.

In one embodiment of the present invention, the dye that has a high affinity to double stranded nucleic acids is an intercalator. In another embodiment, the dye that has a high affinity to double stranded nucleic acids is a groove binder.

In another embodiment, the present invention includes a method for the detection or quantification of a nucleic acid analyte comprising the steps of: (a) providing a nucleic acid probe, wherein said nucleic acid probe is comprised of a nucleic acid that is derivatized with two non-identical covalently attached dyes, of which at least one dye is fluorescent, and of which one dye is a pH-sensitive dye, wherein the dyes are attached at either the same or at adjacent nucleotides of the nucleic acid probe; (b) contacting said nucleic acid probe with a nucleic acid analyte so as to allow for the hybridization of the nucleic acid probe with the nucleic acid analyte; (c) removing the unhybridized nucleic acid probe from the mixture; and (d) measuring the fluorescence of the hybridized nucleic acid probe under one or more conditions where the pH of the medium is defined.

In a preferred embodiment, the pH-sensitive dye is selected from the group including, but not limited to a substituted trityl group, such as a derivative of the dimethoxytrityl group and the covalent attachment of the substituted trityl group to the nucleic acid probe is provided through a linkage of one of the aromatic rings of the substituted trityl group to one of the nucleotides of the nucleic acid probe. The method of claim 24 wherein the substituted trityl group is a derivative of the dimethoxytrityl group.

Included in the present invention is a method of preparing nucleic acid probes, said probes comprised of a nucleic acid that is derivatized with two or more non-identical covalently attached dyes comprising the steps of: (a) providing an oligonucleotide that is derivatized with a diene-moiety and an amino group; (b) reacting the oligonucleotide with a first dye that is derivatized with a dienophile-moiety; and (c) reacting the oligonucleotide with a second dye that is derivatized with an amine-reactive moiety. The present invention also includes the probes prepared according to the method of this invention, wherein said nucleic acid probes are comprised of a nucleic acid that is derivatized with two or more non-identical covalently attached dyes, wherein at least one dye is fluorescent, and wherein at least one dye has a high affinity to double stranded nucleic acids, wherein the dyes are attached at either the same or at adjacent nucleotides of the nucleic acid probe.

Also included in the present invention is a method of preparing an oligonucleotide that is derivatized with a diene moiety and an amino group, said method comprising the steps of: (a) synthesizing an oligonucleotide sequence using standard solid phase phosphoramidite synthesis, using nucleoside phosphoramidites as the reactants; (b) conducting a last phosphoramidite synthesis cycle wherein a phosphoramidite is applied in the coupling step of the synthesis cycle that carries a diene-moiety and a protected amino group; and (c) deprotecting the oligonucleotide. The present invention includes the oligonucleotides prepared by this method.

Conjugation Chemistry

The covalent attachment of dyes to nucleic acids can be achieved by a variety of methods known to those of skill in the art. The covalent attachment of dyes to nucleic acids is reviewed in Davies et al. (2000) Chem. Soc. Rev. 29:97–107, which is incorporated herein by reference in its entirety. Examples include, but are not limited to: incorporation of the dyes during the synthesis of nucleic acids, typically solid phase synthesis, post-synthetic labeling of either synthetic nucleic acids or nucleic acids derived through enzymatic reactions, e.g. the PCR reaction, and enzymatic methods of incorporation of dyes into nucleic acids, e.g. the use of dye conjugated deoxynucleotide triphosphates in primer elongation reactions such as a PCR reaction.

The incorporation of dyes into oligonucleotides using solid phase synthetic methods entails the conversion of the dyes into their phosphoramidite derivatives, which are then employed in the phosphoramidite solid phase synthetic method similar to nucleoside phosphoramidites. Using this method, the amidite derived from a particular dye is mixed with an activator such as 1H-tetrazole or 4,5-dicyanoimidazole, in a suitable solvent, and reacted with a hydroxy group of a support bound oligonucleotide to form a covalent phosphodiester bond between the oligonucleotide and the dye. The attachment of dyes using the phosphoramidite method is reviewed by Beaucage et al. (1993) Tetrahedron 49:1925–63 (1993), which is incorporated herein by reference in its entirety.

Post-synthetic labeling of synthetic nucleic acids or nucleic acids derived from enzymatic reactions involves the incorporation of functional groups into the nucleic acids, which serve as anchor points for the attachment of dyes. The dye is then derivatized with a chemical group or moiety that can be reacted with the functional group of the nucleic acid to promote the formation of a covalent bond between the nucleic acid and the dye. The functional group incorporated into the nucleic acid can be any group that is capable of reacting selectively with the group or moiety that is incorporated into the dye. Examples of functional groups which can be incorporated into nucleic acids and groups or moieties which can be incorporated into dyes, which can then selectively react include, but are not limited to, amino groups/active esters, e.g. hydroxysuccinimide esters, thiol groups/electrophilic groups and dienes/dienophiles, e.g. maleimides. Methods known to those skilled in the art to promote a covalent bond between a nucleic acid and a dye are reviewed by Grimm et al. (2000) Nucleosides & Nucleotides 19:1943–65, which is incorporated herein by reference in its entirety.

The incorporation of functional groups into synthetically derived nucleic acids can be achieved using a variety of methods. A standard method known to those skilled in the art is the use of linker phosphoramidites during solid phase synthesis. Linker molecules useful in the solid phase phosphoramidite method consist of an amidite moiety, a spacer and a functional group that is protected if the functional group interferes with the amidite synthesis. Examples include, but are not limited to, linkers to introduce amino-functions, e.g. (1), thiol-functions, e.g. (2), or diene functions, e.g. (3), below. There are a number of commercially available phosphoramidite linkers.

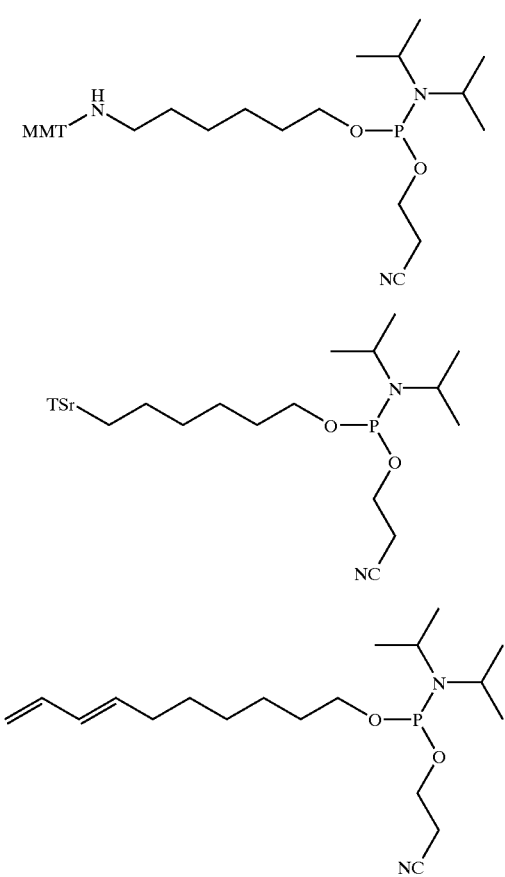

The incorporation of functional groups into nucleic acids derived from enzymatic reactions can be achieved by a variety of methods. The standard method involves the use of primers that contain a functional group at the 5'-end in PCR reactions. The use of such primers results in the generation of PCR reaction products (amplicons) that contain the functional group at the 5'-end of the strand of the amplicon that is derived from the primer with the functional group. An example is the use of 5'-amino derivatized primers, as described by Kohsaka et al. (1993) Nucleic Acids Res. 21:3469–3472, which is incorporated herein by reference in its entirety.

One method of enzymatically incorporating dyes into nucleic acids is the use of dye-conjugated nucleoside triphosphates in primer elongation reactions. This method is used extensively in modifications of the Sanger sequencing method for nucleic acids, as reviewed by Kashdan et al. in "Recombinant DNA Principles Methodologies," Greene and Rao (eds), Dekker 1998, NY, which is incorporated herein by reference. Other methods take advantage of the enzymes T4 polynucleotide kinase or deoxynucleotityl transferase, which incorporate dye-conjugated nucleosides through their triphosphates at the 5'-end or the 3'-end of the nucleic acid, respectively.

Covalent attachment of more than one dye to a nucleic acid can be achieved by a variety of methods, including the use of standard solid phase synthesis, post-synthetic labeling and enzymatic methods, as described above, and any combination thereof of these methods. The dyes can be attached through the use of more than one monofunctional linkers that allow the covalent attachment of one dye only, or through multifunctional linkers that allow the attachment of more than one dye through the same linker.

The nucleic acid probes disclosed herein are comprised of two or more non-identical dyes, covalently attached either to the same nucleotide of a nucleic acid or to adjacent nucleotides of a nucleic acid to provide a close molecular proximity of the dyes. The linkage of the dyes to the nucleic acid can be provided using a variety of methods as described in detail below.

Attachment with a Minimum of Two Different Linkers

According to this embodiment of the invention the linkers can be of the same or of a different chemical nature and can contain the same or different functional groups that provide the attachment points for the dyes. The linkers can be attached to almost any position of the nucleic acid including, but not limited to, the 3'-terminus of the nucleic acid, the 5'-terminus of the nucleic acid and/or an internal position on the nucleic acid. Attachment points of the linkers to the nucleic acid include, but are not limited to, the base of a nucleotide, the sugar of a nucleotide and/or the phosphate group of a nucleotide.

Multiple dye incorporation according to this method may involve protective group chemistry to address the sequential incorporation of the dyes and has been described for the synthesis of molecular beacons, see Tyagi et al. (1996) Nat. Biotechnol. 14:303–308. The synthesis of TAQMAN™ probes, and other probes that require the covalent attachment of two dyes into nucleic acids are described in Aubert et al. (2000) Nucleic Acids Res. 28:818–25, which is incorporated herein by reference in its entirety.

Examples of methods to synthesize nucleic acid probes with multiple non-identical dyes in close molecular proximity, which are attached to the probe with different linkers are outlined below and can easily be adopted by those skilled in the art.

1. Attachment of one dye using post synthetic labeling at the nucleoside base of the 5'-end of the nucleic acid and attachment of a second dye on the same nucleoside using phosphoramidite synthesis at the 5'-end. In one embodiment of this invention, a sequence modifier phosphoramidite, e.g. 5'-dimethoxytrityl-5-[-N-(trifluoracetylaminohexyl)-3-acrylimido]-2'-deoxyuridine-3'-phosphoramidite (commercially available from Glen Research, Sterling, Va., catalog number 10-1039, compound (4)), and a dye phosphoramidite, e.g. fluorescein-phosphoramidite (commercially available from Proligo LLC. Boulder, Colo., catalog number M010181, compound (5)), are consecutively added as the last coupling units in the solid phase synthesis of an oligonucleotide. Upon deprotection of the oligonucleotide with aqueous ammonia, the 5'-terminal nucleoside is covalently attached to two linkers. The first linker provides a primary amino group at the 5-position of the uridine base and the second linker consists of a phosphodiester group with a spacer and a conjugated dye. The primary amino group of the first linker can be employed in a reaction with an N-hydroxysuccinimide ester derivative or another amine-reactive derivative of another dye to provide a nucleic acid probe that contains two dyes attached through different linkers to the 5'-end nucleoside of the oligonucleotide.

of the monomethoxytrityl protective group from the amine with 80% acetic acid, by the reaction of the oligonucleotide with an amine reactive functional group on the second dye. The resulting nucleic acid probe contains two dyes attached through different linkers at the 5'-end nucleoside of the oligonucleotide.

3. Attachment of one dye at the 3'-end of an oligonucleotide through the use of a dye-modified CPG in the synthesis of the oligonucleotide and the attachment of a second dye through post-synthetic labeling at the nucleoside located at the 3'-end of the oligonucleotide. In this embodiment of the

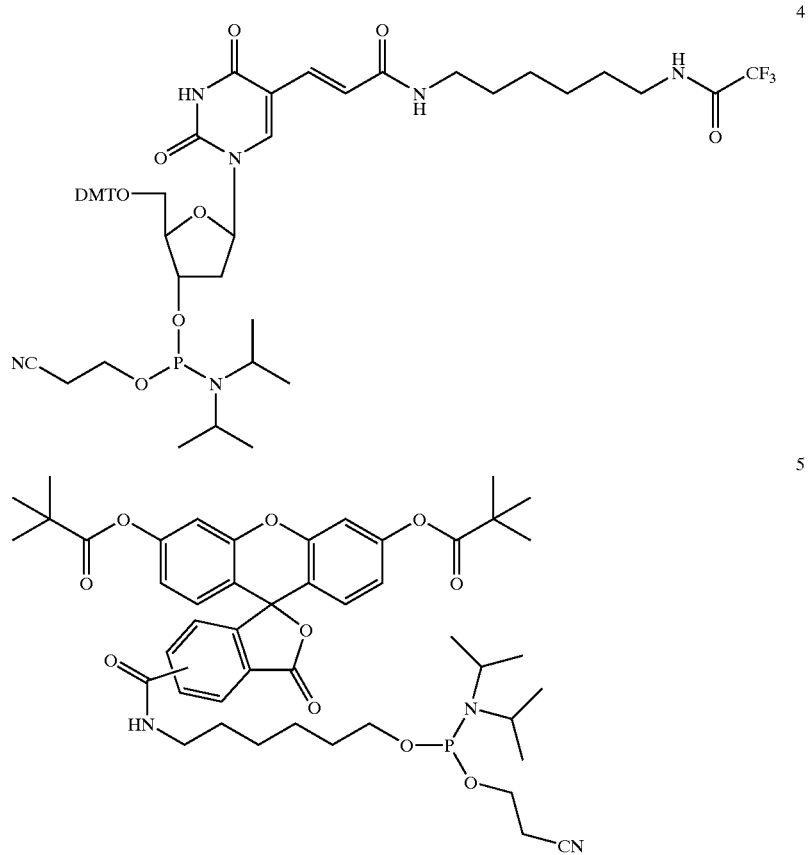

2. The attachment of one dye by the post synthetic labeling of the nucleoside base at the 5'-end of the nucleic acid and attachment of a second dye at the same nucleoside through a protected linker phosphoramidite at the 5'-end, which is further derivatized post-synthetically after deprotection. In another embodiment of this invention, a sequence modifier phosphoramidite, e.g. compound (4), and a terminus modifier phosphoramidite, e.g. compound (1) (commercially available from a number of suppliers), are added consecutively, as the last coupling units in the solid phase synthesis of an oligonucleotide. Upon deprotection of the oligonucleotide with aqueous ammonia the 5'-terminal nucleoside is covalently attached to two linkers. The first linker provides a free primary amino group at the 5-position of the uridine base and the second linker consists of a phosphodiester group with a spacer and a protected amino group. The primary amino group of the first linker can be employed in a reaction with an N-hydroxysuccinimide ester derivative or another amine-reactive derivative of a first dye. A second dye can then be attached selectively after removal invention, a 3'-dye CPG, e.g. 3'-fluorescein-CPG (commercially available from Glen Research, Sterling, Va., catalog number 20-2963, compound (6)) is used to derivatize the oligonucleotide with one of the dyes. A sequence modifier phosphoramidite, e.g. compound (4), is employed in the first coupling to the support. Upon deprotection of the oligonucleotide with aqueous ammonia the 3'-terminal nucleoside is covalently attached to two linkers. The first linker provides a free primary amino group at the 5-position of the uridine base and the second linker consists of a phosphodiester group with a spacer and a conjugated dye. The primary amino group of the first linker can be employed in a reaction with an N-hydroxysuccinimide ester derivative or another amine-reactive derivative of another dye to provide a nucleic acid probe that contains two dyes attached through different linkers at the 5'-end nucleoside of the oligonucleotide.

6

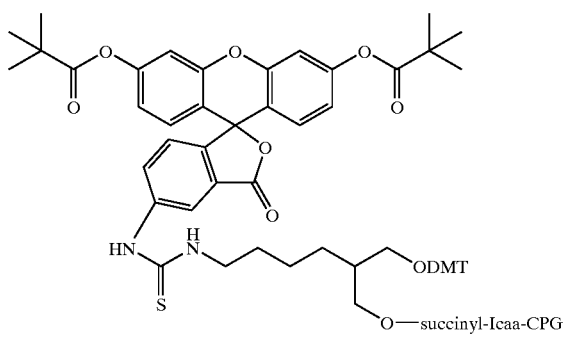

Methods for the synthesis of nucleic acid probes with multiple dyes in close molecular proximity that are attached with different linkers are not limited to the provided examples. There are numerous other functional groups, which will be known to those of skill in the art, that can be employed in the post-synthetic labeling described, various attachment points of the linkers involved and other sequence modifier phosphoramidites of varying chemical structure that can be employed in the synthesis of the probes. Examples of other sequence modifiers are described in Nelson et al. Nucleic Acids Res. 20:6253–6259; Grzybowski et al. (1993) Nucleic Acids Res. 21:1705–1712; Behrens et al. (1999) Nucleosides & Nucleotides 18: 291–305; Behrens et al. (1995) Bioorganic & Medicinal Chemistry Letters 5:1785–90 and Endo et al. (1994) Tetrahedron Letters 35:5879–5882, each of which is specifically incorporated herein by reference in its entirety.

Attachment with a Branched Linker that Connects Two or More Dyes to a Single Position A branched linker contains a minimum of two functional groups of the same or different chemical nature, which provide the attachment points for the dyes and another functional group, which provides the attachment point to the nucleic acid probe. Branched linkers have been synthesized and applied to oligonucleotides for the purpose of generating dendrimeric DNA structures that provide signal amplification in hybridization assays through networks of covalently connected labeled probes. For instance, the branching phosphoramidites (7) and (8) serve as suitable linkers for the generation of dendrimers (http://www.interactiva.de/knowledge/nucleicchem/modifiedoligos.htmL, information retrieved September 2001). Other examples of branched linkers are phosphoramidites (9) and (10), as described by Shchepinov et al. (1999) Nucleic Acids Res. 27:3035–3041 and Shchepinov et al. (1997) Nucleic Acids Res. 25:4447–4454 (1997), which were used to generate dendrimeric oligonucleotides of various structures. Each of these references is specifically incorporated herein by reference in its entirety. Polushin (2000) Nucleic Acids Res. 28:3125–3133, which is hereby incorporated by reference in its entirety, has described the synthesis and the application of the branched linker structures (11) and (12). In this embodiment of the invention, the branching linker and a nucleoside are incorporated in one phosphoramidite structure. Phosphoramidites 7–12 are useful for incorporating multiple reporter molecules into a synthetic oligonucleotide on a branched linker.

7

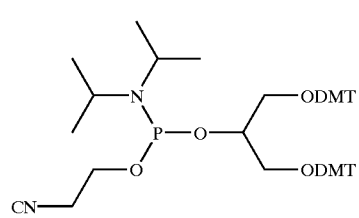

8

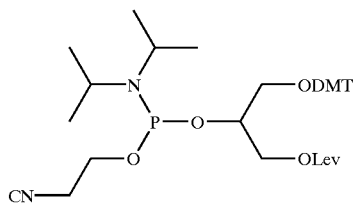

9

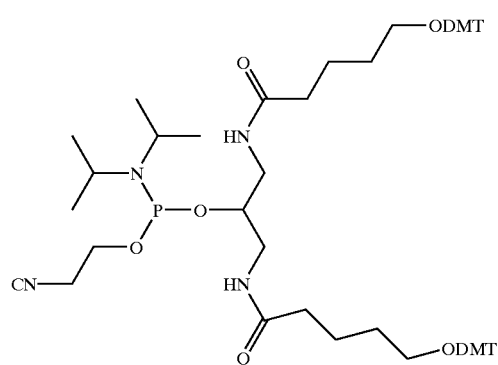

10

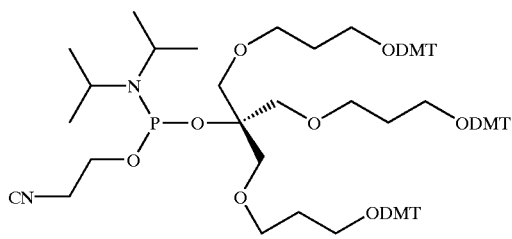

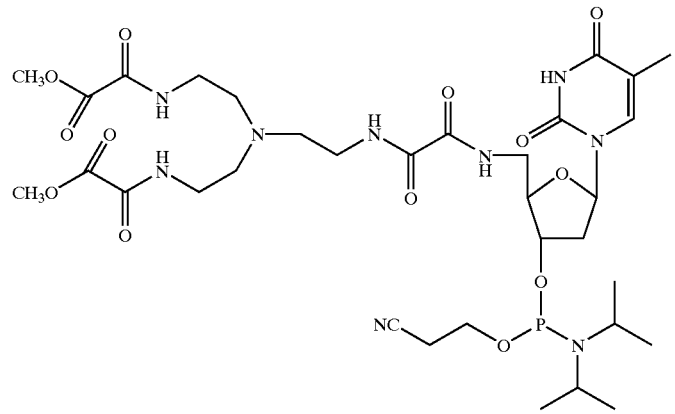

11

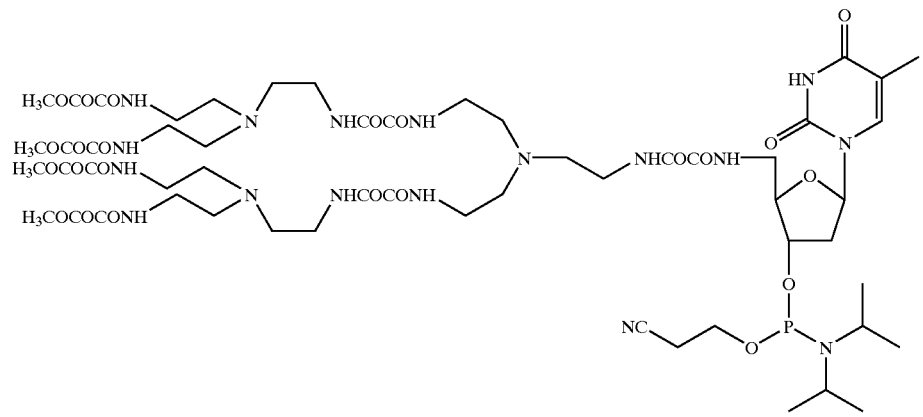

12

Included in the present invention is a method for the synthesis and use of the bifunctional branched linkers (13) and (14). Phosphoramidites (13) and (14) can be incorporated in the solid phase phosphoramidite synthesis of oligonucleotides as the last coupling unit to generate oligonucleotides with a branching linker at the 5'-terminus. Both linkers are non-symmetrical and provide a convenient way to covalently attach two non-identical dyes to the oligonucleotide.

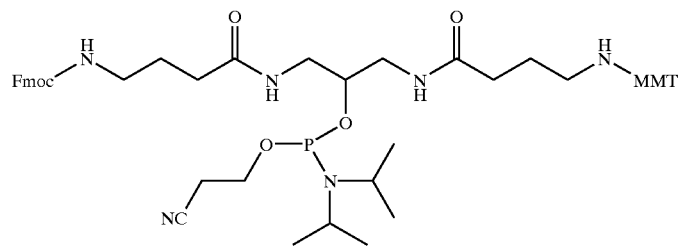

13

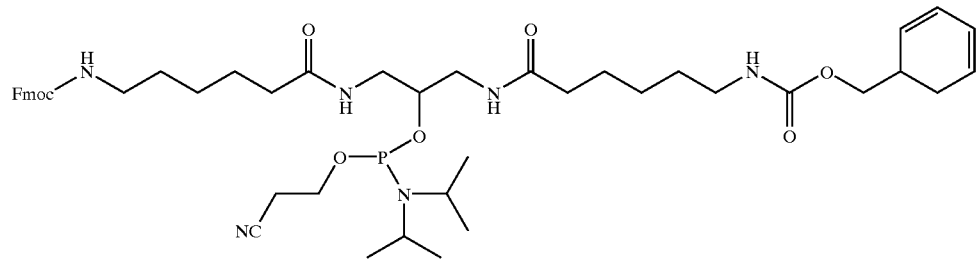

14

The synthesis of linker (13) is described in Example 1 (Scheme 1). With reference to Scheme 1, 4-aminobutyric acid was converted to either 4-Fmoc-aminobutyric acid (Fmoc=fluorenemethyloxycarbonyl) or 4-MMT-aminobutyric acid (MMT=monomethoxytrityl) by reaction with either Fmoc-chloride or MMT-chloride. Both derivatives were further converted to their p-nitrophenylesters by reation with p-nitrophenol and DCC (DCC= dicyclhexylcarbodiimide). Both esters were then successively coupled with 1,3-diamino-2-propanol in the presence of a tertiary base and the resulting product was phosphitylated at the secondary hydroxyl group to provide linker (13).

Linker (13) carries a base-labile Fmoc protecting group, which is removed during the deprotection of the oligonucleotide with aqueous ammonia. The resulting free primary amino group can be employed in a reaction with an N-hydroxysuccinimide ester derivative or another amine-reactive derivative of a dye to generate an oligonucleotide with one covalently attached dye and one protected primary amino group. Following the removal of the monomethoxytrityl group of the second amino group another amine-reactive dye can be reacted with the oligonucleotide to provide a nucleic acid probe that contains two non-identical dyes attached through a branched linker. Examples 3 and 5 describe the synthesis of an oligonucleotide sequence conjugated to bifunctional linker (13).

The synthesis of the linker (14) is described in Example 2 (Scheme 2). With reference to Scheme 2, 6-aminocaproic acid was converted to either its N-(cyclohexa-2,4-dienyl) methoxycarbonyl derivative or its N-Fmoc derivative by reaction with cyclohexa-2,4-dienylmethanol and CDI (CDI= carbonyldiimidazol) or Fmoc-chloride, respectively. Both derivatives were further converted to their pentaflourophenylesters by reaction with pentafluorophenol and DCC. Both esters were then coupled with 1,3-diamino-2-propanol in the presence of a tertiary base and the resulting product was phosphitylated at the secondary hydroxyl group to provide linker (14).

Linker (14) carries a base-labile Fmoc protective group, which is removed during the deprotection of the oligonucleotide with aqueous ammonia. The resulting free primary amino group can be employed in a reaction with an N-hydroxysuccinimide ester derivative or another amine-reactive derivative of a dye to generate an oligonucleotide with one covalently attached dye and one diene group. The diene can subsequently be employed in an aqueous Diels-Alder reaction with a dye that is derivatized with a dienophile, such as a maleimide, as described by Hill et al. (2001) J. Org. Chem. 66:5352–58, which is incorporated herein by reference in its entirety. The product of the Diels-Alder reaction is a nucleic acid probe that contains two non-identical dyes attached through a branched linker. Linker (14) provides the additional advantage that the attachment of both dyes can be performed simultaneously in a one-pot reaction. A one-pot reaction dramatically reduces the effort that is applied with the synthesis and purification in a stepwise sequential manner. Example 4 describes the synthesis of a dT10 oligonucleotide sequence conjugated to bifunctional linker (14).

Example 6 describes the coupling of the linker (14) to the 5'-termini of oligonucleotides using solid phase phosphoramidite synthesis with DCI (4,5-dicyanoimidazole) as the activator of the amidite. Repeated couplings, i.e. repeated delivery of the amidite and activator solution, proved to be advantageous with linker (14) and three successive coupling steps were routinely employed. Also included in Example 6 is the optional introduction of a hexaethyleneglycol (HEG) spacer in between the oligonucleotide sequence and the linker moiety. For this purpose a DMT-protected HEG amidite is coupled to the oligonucleotide sequence before linker (14) is introduced. It is well known that the nucleobases of an oligonucleotide, in particular guanine, may contribute to the quenching of attached fluorescent reporter dyes, as described by Seidel et al. (1996) J. Phys. Chem. 100:5541–5553, which is incorporated herein by reference in its entirety. A spacer moiety such as the HEG spacer or an oligo-thymidine unit, as also incorporated in some of the linker-modified oligonucleotides of this invention, may reduce this kind of interference. Such spacer moieties may further improve the efficiency of the final doubly labeled nucleic acid probe as they impart increased range and higher flexibility to the dyes, thereby facilitating their interaction with the target sequence upon hybridization.

Attachment of Dye Combinations that are Chemically Conjugated to the Nucleic Acid with a Single, Non-Branched Linker In one embodiment of the present invention, the linker is comprised of a combination of at minimum two dyes, which are covalently linked together. Examples of such dyes include, but are not limited to, terminator dyes, which are being used in sequencing. See for example Lee et al. (1997) Nucleic Acids Res. 25:2816–2822, which is incorporated herein by reference in its entirety, which describes the use of 4-aminomethylbenzoic acid as a bifunctional linker to connect substituted fluorescein and rhodamine dyes. The two dyes are attached to oligonucleotides through a single linker at the respective fluorescein dye (BigDye™ technology).

Nucleic Acid Probes

Intercalators and groove binders are classes of dyes that have an affinity to double stranded DNA. Upon interaction with the DNA, an intercalator is characterized by its insertion between adjacent base pairs of the DNA in an intercalative manner, stabilized by van der Waals dispersion interactions with the base pairs surrounding it. Examples of intercalators include, but are not limited to, proflavine, ethidium bromide, acridine-derivatives, polyaromatic hydrocarbons, e.g. pyrene-derivatives and perylene-derivatives. The nucleic acid probes of this invention include, but are not limited to, the examples of intercalators provided above, as well as all other dyes that interact with double stranded DNA in an intercalative manner.

Groove binders are characterized by their non-covalent binding to the outer side of a double helical structure. Examples of groove binders include Hoechst 33258, 2-phenylindole dyes, e.g. 4',6-diamidino-2-phenylindole, berenil and netropsin. The nucleic acid probes of this invention include, but are not limited to, the examples of groove binders provided above, as well as all other dyes that interact with double stranded DNA through non-covalent binding to the outer side of the double helical structure. Further examples of intercalators and groove binders, a discussion regarding their structural features and their mechanism of binding to DNA, as well as, the resulting implications for the structure of double stranded DNA are provided in Neidle, "DNA Structure and Recognition," Oxford University Press, which is incorporated herein by reference in its entirety.

The asymmetric cyanine dye thiazole orange (TO) is another example of a compound that has a strong affinity to double stranded nucleic acids. Further interesting attributes of TO are a low intrinsic fluorescence, a strong enhancement of fluorescence upon binding to nucleic acids, and a high fluorescence quantum yield if complexed to nucleic acids. The fluorescence enhancement that occurs upon binding to nucleic acids is probably due to the restriction of the rotation around the central bond of the dye in the bound state, as discussed by Nygren et al. (1998) Biopolymers 46:39–51, which is incorporated herein by reference in its entirety. The mechanism of binding of TO to nucleic acids has not been fully explored, but it is assumed that intercalation contributes to the observed strong affinity. However, groove binding cannot be ruled out as well. Solutions of the dye TO are well suited for staining nucleic acids in gels, as has been demonstrated for monomeric or dimeric TO. See e.g. Rye et al. (1992) Nucleic Acid Res. 20:2803–2812, which is incorporated herein by reference in its entirety. In addition, sequence-specific hybridization probes based on the non-natural nucleic acid backbone PNA (peptide nucleic acids) that are labeled with TO have been employed in homogenous assays. The PNA-TO conjugates indicate the presence of a target sequence by an enhanced fluorescence compared to the unhybridized state. PNA-TO conjugates are described by Kubista et al., U.S. Pat. No. 6,329,144 and by Svanvik et al. (2000) Anal. Biochem. 281:26–35, each of which is incorporated herein by reference in its entirety. Conjugates of TO with DNA oligonucleotides are less suitable as hybridization probes than the PNA based probes because of their high intrinsic fluorescence, which results from the binding of the positively charged dye to the negatively charged backbone of the natural phosphodiester oligonucleotide. PNA is employed in the hybridization probes of the prior art in order to overcome this drawback because PNA provides an uncharged backbone structure.

For the purpose of the present invention, a dye has a high affinity to double stranded nucleic acids if it binds to double stranded nucleic acids with an association constant of $10^3$ $M^{-1}$ or greater. In some instances, dyes with a high affinity to double stranded nucleic acids bind with association constants of the magnitude of $10^7$ to $10^9$ $M^{-1}$. As discussed for the dye thiazole orange, it may not be well established whether a dye with a high affinity to double stranded nucleic acids binds to the nucleic acids by intercalation or by groove binding. It is, however, not of prime importance in the context of the present invention to have a precise knowledge regarding the exact mechanism of binding of the dye to nucleic acids. For the present invention such dyes may be classified either as intercalators or groove binders although the exact mechanism of binding may be determined later to be different from such a classification.

The present invention is drawn to nucleic acid probes that are derivatized with two or more non-identical covalently attached dyes wherein one of the dyes has a high affinity to double stranded nucleic acids. Examples of dyes with a high affinity to double stranded nucleic acids that can be employed in the instant invention include, but are not limited to ethidium and thiazole orange, as well as, any other dye with a high affinity to double stranded nucleic acids.

The synthesis of ethidium dye derivative (15), which is suitable in post-synthetic labeling methods based on aqueous Diels-Alder chemistry, is described in Example 7 (Scheme 3). Ethidium bromide was converted to ethidium tetraphenylborate in order to increase the solubility of the ethidium dye in common organic solvents. The tetraphenylborate salt was reacted with 6-maleimidocaproic acid chloride and the resulting conjugate was reconverted to the bromide salt using an anion exchange resin. The ethidium derivative (15) is comprised of a maleimide group, which is reactive towards diene groups in an aqueous media and can be employed to conjugate ethidium to oligonucleotides that carry the diene containing bifunctional linker (14).

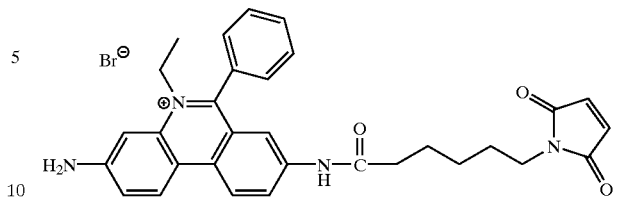

The synthesis of thiazole orange dye derivative (16), which is suitable in post-synthetic labeling methods with amino-functionalized oligonucleotides, is described in Example 8 (Scheme 4). The synthesis was performed in accordance with procedures described in U.S. Pat. No. 6,348,596 and PCT publication number WO 96/22383 A1, each of which is incorporated herein by reference in its entirety, with several modifications. Quaternary salts of benzothiazole and lepidin were synthesized as intermediates with methyl-p-toluenesulfonate and 6-bromohexanoic acid as alkylating agents. The alkylated heterocycles were condensed in the presence of triethylamine in dichloromethane at room temperature to give a hexanoic acid derivative of thiazole orange, which was converted to its N-hydroxysuccinimide ester (16) with dicyclohexylcarbodiimide. Thiazole orange derivative (16) contains an activated ester group that will react with free primary amines in aqueous solutions. Compound (16) is suitable to attach the dye thiazole orange to oligonucleotides that carry the bifunctional linker (14).

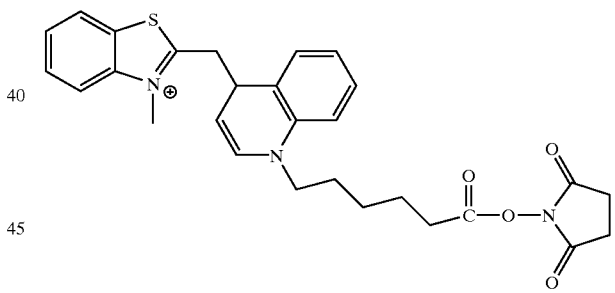

A preferred embodiment of the invention for synthesizing doubly labeled oligonucleotides is described in Example 9. Oligonucleotides that have been modified with the bifunctional linker (14) as described in Example 6 are simultaneously reacted with one dye that is derivatized with an amine-reactive group, such as an N-hydroxy-succinimide ester and a second dye that is derivatized with a dienophile, such as a maleimide. Both concurrent reactions are efficiently conducted at 37° C. over a period of 3 hours at neutral pH. A final purification by gel electrophoresis yields the doubly labeled oligonucleotide probes that are ready to be used for assaying nucleic acid analytes. The general formula representing the doubly labeled probes as synthesized according to Example 9 is depicted in formula (17) and a list of examples of probes with two covalently attached dyes that were prepared by this method is provided in Table 1.

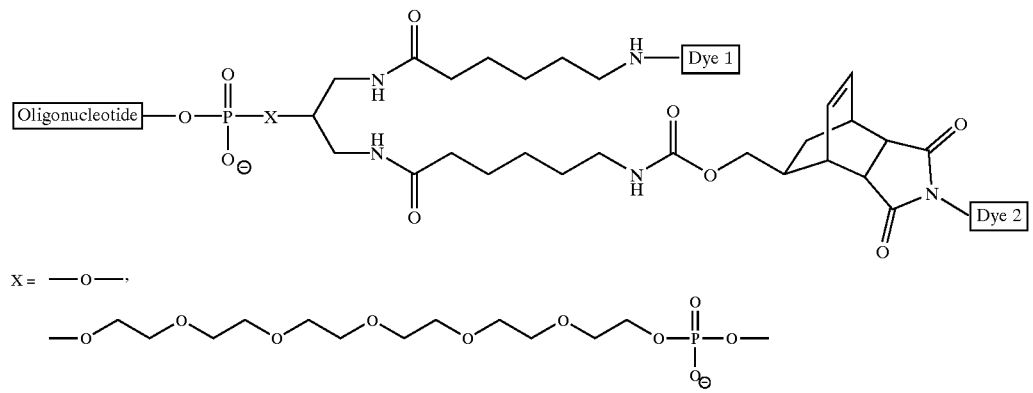

X = —O—, $$\text{—O} \smile \text{O} \smile \text{O} \smile \text{O} \smile \text{O} \smile \text{O-P-O—}$$

TABLE 1

Doubly labeled probes synthesized according to Example 9

| Probe No. | Sequence | Dye I[1] | Dye II[2] | 5'-Modification as introduced by | SEQ ID NO: |
|---|---|---|---|---|---|
| 17.1 | 5'-d(TTT-TTT-TTT-TTT-TTT-TTT-TT)-3' | QSY 7 | Ethidium | (14) | 1 |
| 17.2 | 5'-d(TTT-TTT-TTT-TTT-TTT-TTT-TT)-3' | 5(6)-FAM | Ethidium | (14) | 1 |
| 17.3 | 5'-d(CGC-TCA-TCT-TCA-AGT-CCA-CCC-T)-3' | QSY-7 | Ethidium | (14) | 2 |
| 17.4 | 5'-d(CGC-TCA-TCT-TCA-AGT-CCA-CCC-T)-3' | 5(6)-FAM | Ethidium | (14) | 2 |
| 17.5 | 5'-d(CGC-TCA-TCT-TCA-AGT-CCA-CCC-G)-3' | 5(6)-TAMRA Ethidium | (14) | | 3 |
| 17.6 | 5'-d(CGC-TCA-TCT-TCA-AGT-CCA-CCC-T)-3' | 5(6)-FAM | Ethidium | (14) | 2 |
| 17.7 | 5'-d(CGC-TCA-TCT-TCA-AGT-CCA-CCC-T)-3' | QSY-7 | Ethidium | (14) | 2 |
| 17.8 | 5'-d(CGC-TCA-TCT-TCA-AGT-CCA-CCC-G)-3' | 5(6)-TAMRA Ethidium | (14) | | 3 |
| 17.9 | 5'-d(TTT-TT-CGC-TCA-TCT-TCA-AGT-CCA-CCC-T)-3' | 5(6)-FAM | Ethidium | (14) | 4 |
| 17.10 | 5'-d(TTT-TT-CGC-TCA-TCT-TCA-AGT-CCA-CCC-G)-3' | 5(6)-FAM | Ethidium | (14) | 5 |
| 17.11 | 5'-d(TTT-TT-CGC-TCA-TCT-TCA-AGT-CCA-CCC-T)-3' | TO | QST-7 | (14) | 4 |
| 17.12 | 5'-d(TTT-TT-CGC-TCA-TCT-TCA-AGT-CCA-CCC-T)-3' | TO | 5-TAMRA | (14) | 4 |
| 17.13 | 5'-d(TTT-TT-CGC-TCA-TCT-TCA-AGT-CCA-CCC-G)-3' | TO | 5-TAMRA | (14) | 5 |
| 17.14 | 5'-d(TT-TT-CGC-TCA-TCT-TCA-AGT-CCA-CCC-T)-3' | TO | Texas Red | (14) | 4 |
| 17.15 | 5'-d(TTT-TT-CGC-TCA-TCT-TCA-AGT-CCA-CCC-T)-3' | TO | MDCC | (14) | 4 |
| 17.16 | 5'-d(TTT-TT-CGC-TCA-TCT-TCA-AGT-CCA-CCC-G)-3' | TO | MDCC | (14) | 5 |
| 17.17 | 5'-d(CGC-TCA-TCT-TCA-AGT-CCA-CCC-T)-3' | TO | 5-FAM | (14) | 2 |
| 17.18 | 5'-d(TTT-TT CGC-TCA-TCT-TCA-AGT-CCA-CCC-T)-3' | TO | 5-FAM | (14) | 4 |
| 17.19 | 5'-d(CGC-TCA-TCT-TCA-AGT-CCA-CCC-T)-3' | TO | 5-FAM | 1.HEG-amidite 2. (14) | 2 |
| 17.20 | 5'-d(CGC-TCA-TCT-TCA-AGT-CCA-CCC-T)-3' | TO | Texas Red | 1.HEG-amidite 2. (14) | 2 |

TABLE 1-continued

Doubly labeled probes synthesized according to Example 9

| Probe No. | Sequence | Dye I[1] | Dye II[2] | 5'-Modification as introduced by | SEQ ID NO: |
|---|---|---|---|---|---|
| 17.21 | 5'-d(CGC-TCA-TCT-TCA-AGT-CCA-CCC-T)-3' | TO | MDCC | 1.HEG-amidite 2. (14) | 2 |
| 17.22 | 5'-d(TTT-TT-CGC-TCA-TCT-TCA-AGT-CCA-CCC-T)-3' | 5(6)-FAM | Ethidium | (14) | 4 |
| 17.23 | 5'-d(TTT-TT-CGC-TCA-TCT-TCA-AGT-CCA-CCC-T)-3' | TO | 5-FAM | (14) | 4 |
| 17.24 | 5'-d(TTT-TT-CAC-TGG-GAG-CAT-TGA-GGC-TC)-3' | TO | MDCC | (14) | 6 |
| 17.25 | 5'-d(TTT-TT-CAC-TGG-GAG-CAT-TGA-GGC-TC)-3' | TO | 5-FAM | (14) | 6 |
| 17.26 | 5'-d(TTT-TT-CAC-TGG-GAG-CAT-TGA-GGC-TC)-3' | TO | 5-TAMRA | (14) | 6 |
| 17.27 | 5'-d(TTT-TT-CGC-TCA-TCT-TCA-AGT-CCA-CCC-T)-3' | TO | none | 1.HEG-amidite 2. (14) | 4 |
| 17.28 | 5'-d(ATT-CTC-AAC-TCT-GAC-TGT-GAG-CAA-CA)-3 | TO | MDCC | (14) | 7 |
| 17.29 | 5'-d(ATT-CTC-AAC-TCT-GAC-TGT-GAG-CAA-CA)-3 | TO | 5-FAM | (14) | 7 |
| 17.30 | 5'-d(ATT-CTC-AAC-TCT-GAC-TGT-GAG-CAA-cA)-3' | TO | 5-TAMRA | (14) | 7 |
| 17.31 | 5'-d(AAC-TCC-TCT-TCA-GTA-AAG-CCC-ATG-TCC-CGT)-3 | TO | MDCC | 1.HEG-amidite 2. (14) | 8 |
| 17.32 | 5-d(AAA-CTC-CTC-TTC-AGT-AAA-GCC-CAT-GTC-CCG-T)-3' | TO | MDCC | 1.HEG-amidite 2. (14) | 9 |
| 17.33 | 5'-d(TTC-AGT-AAA-GCC-CAT-GTC-CCG-TT)-3' | TO | MDCC | 1.HEG-amidite 2. (14) | 10 |

[1] attached via corresponding NHS-ester.
[2] attached via corresponding maleimide.

In one embodiment of the present invention, the nucleic acid probe is designed to carry both a covalently attached intercalator and at minimum one other dye. At least one of the attached dyes is fluorescent and its fluorescence properties depend on whether or not the intercalator is incorporated into double stranded DNA. Nucleic acid probes that are designed according to this embodiment are useful to detect and quantify nucleic acids. The design of the nucleic acid probes of this embodiment can be applied in the following variations.

The nucleic acid probe is comprised of a covalently attached intercalator and one other covalently attached dye (1.–3.). In this embodiment, either of the two dyes or both of the dyes can be fluorescent.

Figure 1:
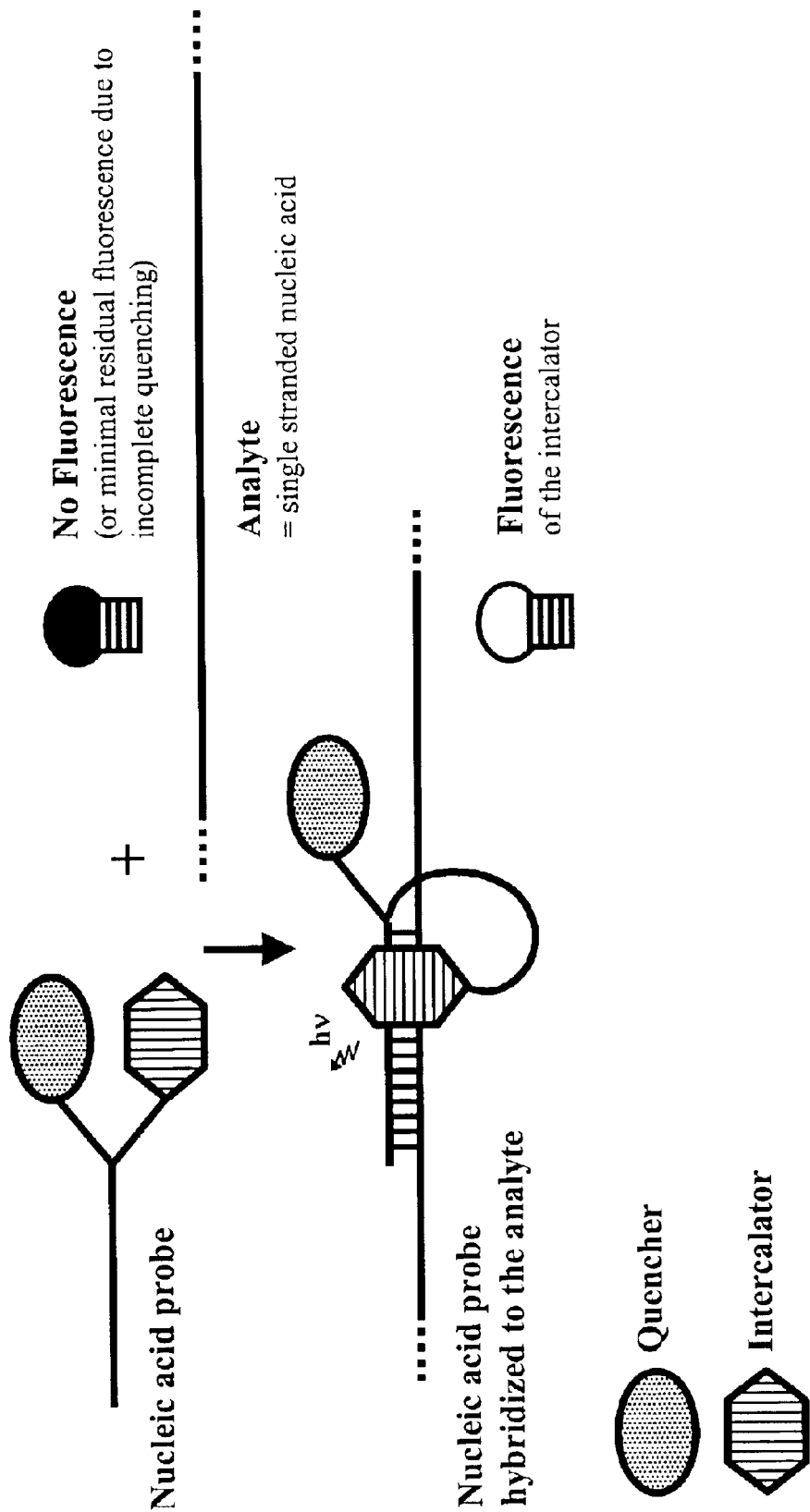
FIG. 1 is a schematic representation of a method for detecting and quantifying nucleic acid analytes employing specific nucleic acid probes, which carry an intercalator serving as detector dye and a non-fluorescent quencher (type I nucleic acid probes).

1. The intercalator is fluorescent and serves as the detector dye and the second dye is a non-fluorescent quencher. As a single stranded nucleic acid the nucleic acid probe displays either none or only minimal fluorescence that is caused by incomplete quenching of the fluorescence from the intercalator. Upon hybridization of the nucleic acid probe to a nucleic acid analyte of complementary sequence increased fluorescence is observed due to the interaction of the intercalator with the formed double stranded nucleic acid. The incorporation of the intercalator into the double stranded nucleic acid increases the distance between the intercalator and the quencher and therefore reduces the efficiency of the quenching which in turn enhances the fluorescence of the intercalator. It is expected that the observed fluorescence will be markedly different from the fluorescence of the unattached intercalator, it is well known that the fluorescence of a non-conjugated intercalator differs from the fluorescence of the same intercalator after incorporation into double stranded DNA. See Haugland in *Handbook of Fluorescent Probes and Research Chemicals*, Molecular Probes, Inc., Eugene, Oreg., which is incorporated herein by reference in its entirety. The differences in fluorescence between the non-conjugated intercalator and the intercalator after incorporation into double stranded DNA could encompass the emission wavelength, the fluorescence intensity and the fluorescence lifetime. The underlying principle of this method is illustrated in FIG. 1. Probes that have a structure according to the principle outlined in FIG. 1 are denoted as type I nucleic acid probes in the context of this invention.

The present invention includes a universal quencher moiety to attach a fluorescent intercalator to oligonucleotides, as well as, a non-fluorescent quencher moiety to attach a non-fluorescent intercalator to oligonucleotides with a single, non-branched linker. The universal quencher structure consists of a dabcyl moiety (dabcyl=p-dimethylamino-azobenzene) that can be covalently linked to a variety of intercalators via a spacer of varying length, as illustrated by structure (18). Notably, the linker that is attached at the 3-position of the dabcyl group, i.e. meta to the carboxyl group, can also be attached at the 2-position, i.e. ortho to the carboxyl group. The universal quencher can be covalently linked to oligonucleotides at the carboxyl group of the dabcyl substructure through a variety of methods. Examples include, but are not limited to, the attachment via a phosphoramidite derivative, as described e.g. with (19), or the attachment through post-synthetic derivatization techniques, e.g. through the N-hydroxysuccinimide ester derivative of (18), or through another amine-reactive derivative of (18), that is reacted with an amino functionalized oligonucleotide, and other post-synthetic conjugation methods.

cyl moiety of compound (18), is advantageous in that it can efficiently quench the fluorescence of a wide range of fluorochromes, including those most commonly used in nucleic acid sequencing and detection applications. Upon hybridization the donor displays enhanced fluorescence due to the less effective quenching caused by the interaction of the intercalator with the double stranded DNA.

In this embodiment the intercalator may or may not change its fluorescent properties upon hybridization of the nucleic acid probe to a complementary target sequence. Changes in the fluorescent properties of the intercalator upon hybridization may include a shift in the maxima of the

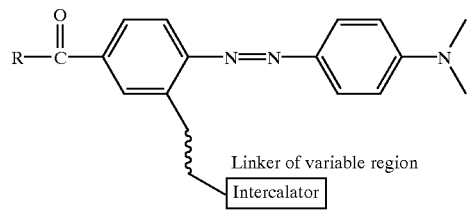

18

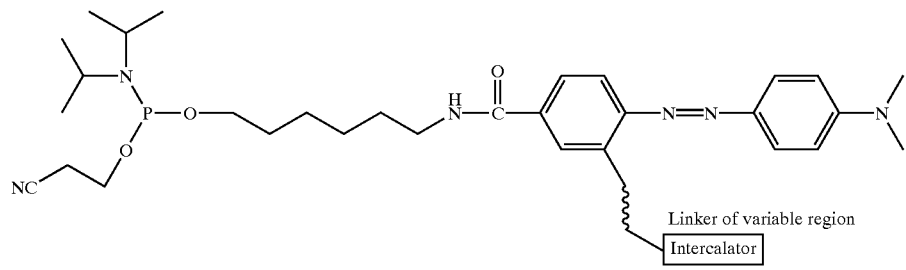

19

2. The intercalator is fluorescent and serves as the detector dye and the second dye is another fluorescent dye that serves as the donor dye of a FRET system composed of the intercalator and the second dye. In this embodiment, both dyes modify the fluorescent properties of each other through the FRET process. As a single stranded nucleic acid, the nucleic acid probe displays fluorescence upon excitation of either the donor or the intercalator, but excitation of the donor leads to a greatly decreased fluorescence of the donor compared to the fluorescence of the non-conjugated donor. Simultaneously, an increased fluorescence of the intercalator compared to the excitation of the non-conjugated intercalator is observed due to the energy transfer. After hybridization of the nucleic acid probe to a nucleic acid analyte of complementary sequence increased fluorescence is observed upon excitation of the donor due to the interaction of the intercalator with the formed double stranded nucleic acid. The incorporation of the intercalator into the double stranded nucleic acid increases the distance between the intercalator and the donor and therefore reduces the efficiency of the FRET process, which in turn enhances the fluorescence of the donor. In this system the fluorescence of the intercalator is simultaneously decreased when the donor is excited.

Figure 2:
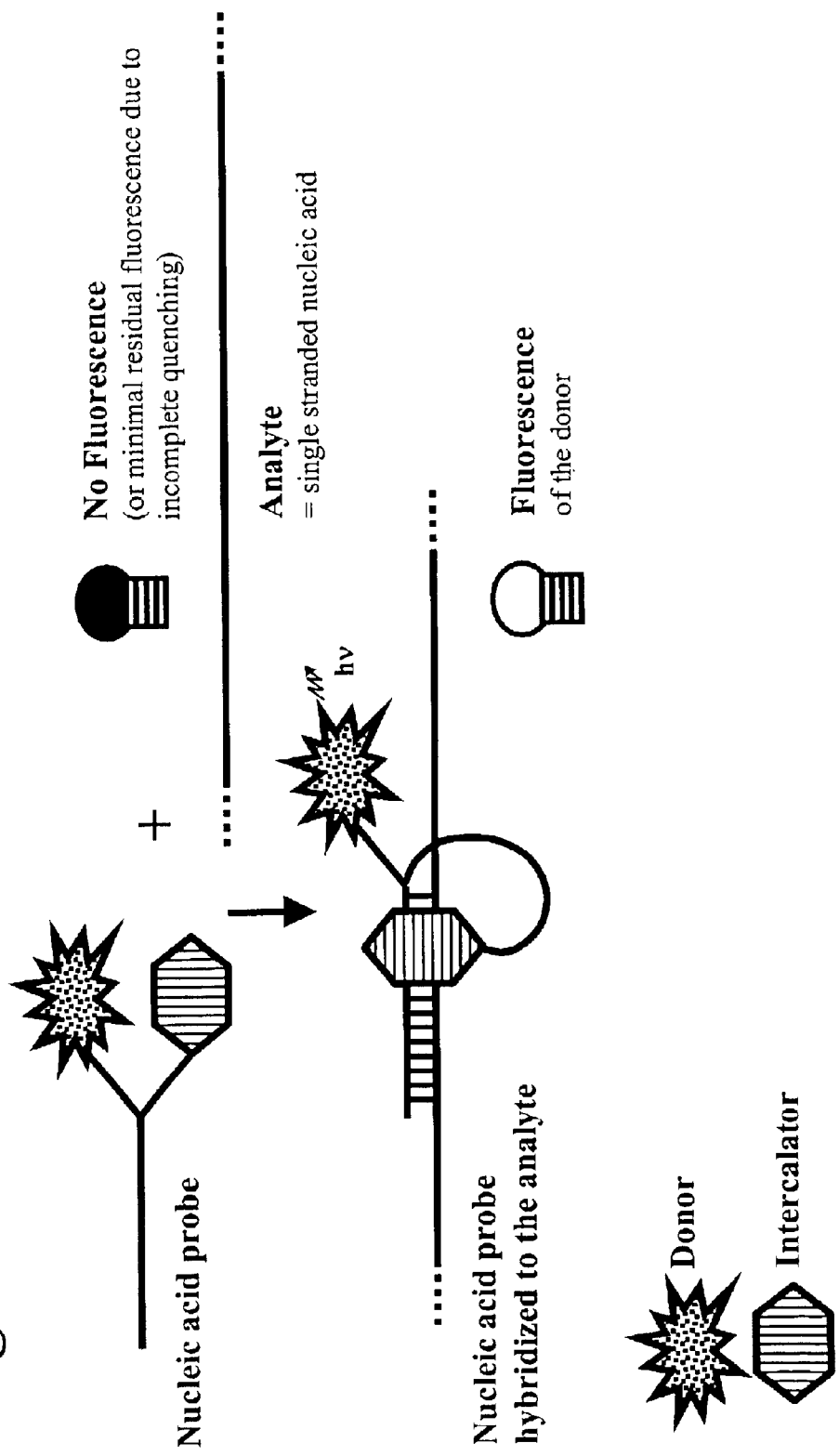
FIG. 2 is a schematic representation of a method for detecting and quantifying nucleic acid analytes employing specific nucleic acid probes, which are attached to a FRET system composed of a donor dye and a fluorescent intercalator serving as detector dye (type II nucleic acid probes).

The underlying principle of this method is illustrated in FIG. 2. Probes that have a structure according to the principle outlined in FIG. 2 are referred to herein as type II nucleic acid probes. In this method of detection, the universal quencher structure (18) can simultaneously serve as quencher and intercalator, with another fluorochrome donor dye attached to the nucleic acid probe in close molecular proximity. The universal quencher, exemplified by the dabfluorescence excitation and/or emission spectra or a decreased or increased fluorescence intensity. For example, the dye thiazole orange displays a remarkable increase in its fluorescence intensity upon its interaction with double stranded nucleic acids which is accompanied by a small shift in the maxima of the fluorescence excitation and emission spectra, as discussed by Rye et al. (1992) Nucleic Acid Res. 20:2803–2812. In this case the hybridization of a type II nucleic acid probe of the invention could potentially not only result in a higher fluorescence intensity of the donor dye upon excitation of the donor, but, in addition, also to a higher fluorescence intensity of the intercalator upon excitation of the donor, because the intercalator in the hybridized form of the probe can be more efficiently excited through a FRET mechanism upon excitation of the donor due to its stronger overall fluorescence.

3. The intercalator is fluorescent and serves as the detector dye and the second dye is another fluorescent dye that serves as the acceptor dye of a FRET system comprised of the intercalator and the second dye. In this embodiment, both dyes modify the fluorescent properties of each other through the FRET process. As a single stranded nucleic acid the nucleic acid probe displays fluorescence upon excitation of either the intercalator or the acceptor, but excitation of the intercalator leads to decreased fluorescence compared to the excitation of the non-conjugated intercalator and increased fluorescence of the acceptor compared to the excitation of the non-conjugated acceptor. After hybridization of the nucleic acid probe to a nucleic acid analyte of complementary sequence increased fluorescence is observed upon excitation of the intercalator due to the interaction of the intercalator with the formed double stranded nucleic acid.

Figure 3:
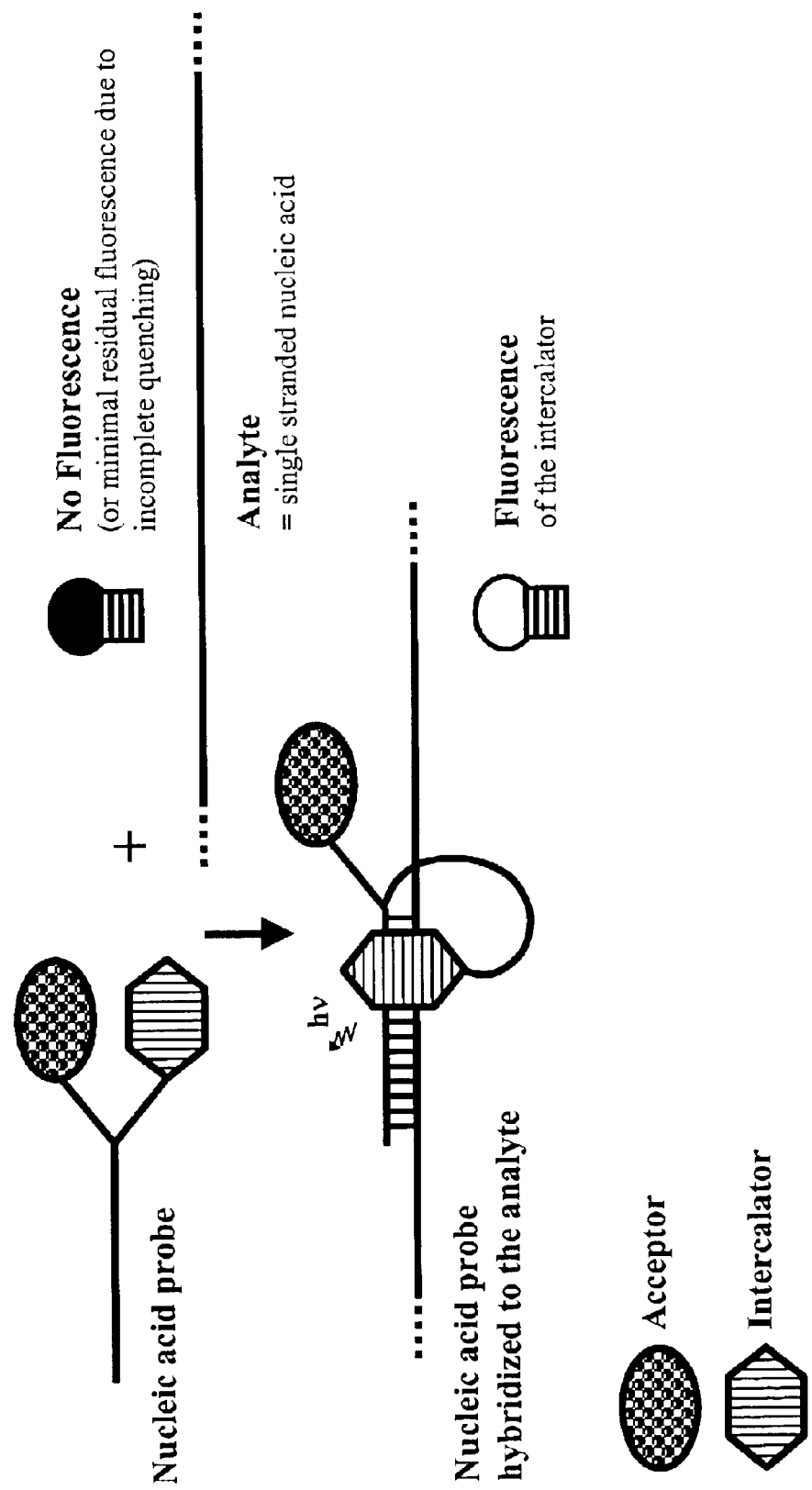
FIG. 3 is a schematic representation of a method for detecting and quantifying nucleic acid analytes employing specific nucleic acid probes, which are attached to a FRET system composed of an acceptor dye and a fluorescent intercalator serving as detector dye (type III nucleic acid probes).

The incorporation of the intercalator into the double stranded nucleic acid increases the distance between the intercalator and the acceptor and therefore reduces the efficiency of the FRET process, which in turn enhances the fluorescence of the intercalator. For many known intercalators fluorescence is further enhanced as a result of the intercalation process. (Haugland in "Handbook of Fluorescent Probes and Research Chemicals," Molecular Probes, Inc., Eugene, Oreg.). In this system, the fluorescence of the acceptor is simultaneously decreased when the intercalator is exited. The underlying principle of this method of detection is illustrated in FIG. 3. Probes that have a structure according to the principle outlined in FIG. 3 are referred to herein as type III nucleic acid probes.

In this embodiment the intercalator may or may not change its fluorescent properties upon hybridization of the nucleic acid probe to a complementary target sequence, including shifts in the maxima of the fluorescence excitation and emission spectra and a decrease or increase of the fluorescence intensity, as discussed for type II nucleic acid probes. In the case of an increased fluorescence intensity of the intercalator upon hybridization the hybridization of a type III nucleic acid probe of the invention could potentially not only result in a higher fluorescence intensity of the intercalator upon excitation of the intercalator, but, in addition, also to a higher fluorescence intensity of the acceptor dye upon excitation of the intercalator, because the acceptor dye in the hybridized form of the probe can be more efficiently excited through a FRET mechanism upon excitation of the intercalator due to the stronger overall fluorescence of the intercalator.

The nucleic acid probe is comprised of a covalently attached intercalator and two other covalently attached dyes (4.–5.). The dyes that are not intercalators are covalently linked through a spacer and form a dye pair that is fluorescent.

4. In this embodiment of the instant invention, the dye pair is an excimer pair that forms an excimer upon exposure to electromagnetic radiation. The excimer pair is used as the detector dye. As a single stranded nucleic acid the nucleic acid probe displays fluorescence that is caused by the excimer. Upon hybridization of the nucleic acid probe to a nucleic acid analyte of complementary sequence decreased fluorescence of the excimer is observed due to the interaction of the intercalator with the formed double stranded nucleic acid. The incorporation of the intercalator into the double stranded nucleic acid increases the distance between the dyes of the excimer pair and therefore reduces the efficiency of the formation of the excimer, which in turn reduces the fluorescence caused by the excimer pair. The fluorescence caused by the excimer pair can be advantageously monitored because excimer pairs are known to have comparatively large Stokes shifts, which leads to increased signal to noise ratios. Furthermore, the efficiency of the formation of an excimer is very sensitive to the molecular distance of the excimer partners, see De Schryver et al. (1987) Acc. Chem. Res. 20:159–66. The underlying principle of this embodiment is illustrated in FIG. 4. Probes that have a structure according to the principle outlined in FIG. 4 are denoted herein as type IV nucleic acid probes.

5. In this embodiment to the instant invention, the dye pair is an exciplex pair that forms an exciplex upon exposure to electromagnetic radiation. The exciplex pair is used as the detector dye. As a single stranded nucleic acid, the nucleic acid probe displays fluorescence that is caused by the exciplex. Upon hybridization of the nucleic acid probe to a nucleic acid analyte of complementary sequence decreased fluorescence is observed due to the interaction of the intercalator with the formed double stranded nucleic acid. The incorporation of the intercalator into the double stranded nucleic acid increases the distance between the dyes of the exciplex pair and therefore reduces the efficiency of the formation of the exciplex, which in turn reduces the fluorescence caused by the exciplex pair. The fluorescence caused by the exciplex pair can be advantageously monitored because exciplex pairs are known to have comparatively large stokes shifts, which leads to increased signal to noise ratios. Furthermore, the efficiency of the formation of an exciplex is very sensitive to the molecular distance of the exciplex partners, similar to the efficiency of the formation of an excimer, as discussed above. This embodiment of the instant invention is illustrated in FIG. 5. Probes that have a structure according to the principle outlined in FIG. 5 are denoted herein as type V nucleic acid probes.

In another embodiment, the nucleic acid probe is designed to carry both a covalently attached groove binder and at minimum one other dye. At least one of the attached dyes is fluorescent and its fluorescence properties depend on the interaction of the groove binder with double stranded DNA. Nucleic acid probes that are designed according to this embodiment are useful to detect and quantify nucleic acids. The design of the nucleic acid probes of this embodiment can be applied in the following variations.

The nucleic acid probe is comprised of a covalently attached groove binder and one other covalently attached dye (6.–8.). In this embodiment, either of the two dyes or both dyes can be fluorescent dyes.

6. In this embodiment, the groove binder is fluorescent and serves as the detector dye and the second dye is a non-fluorescent quencher. As a single stranded nucleic acid the nucleic acid probe displays either none or only minimal fluorescence that is caused by incomplete quenching of the fluorescence from the groove binder. Upon hybridization of the nucleic acid probe to a nucleic acid analyte of complementary sequence increased fluorescence is observed due to the interaction of the groove binder with the formed double stranded nucleic acid. The incorporation of the groove binder into the double stranded nucleic acid increases the distance between the groove binder and the quencher and therefore reduces the efficiency of the quenching, which in turn enhances the fluorescence of the groove binder. It is expected that the observed fluorescence will markedly different from the fluorescence of the unattached groove binder, because in many literature examples the fluorescence of a non-conjugated groove binder differs from the fluorescence of the same groove binder after incorporation into double stranded DNA. The differences in fluorescence between the non-conjugated groove binder and the groove binder after incorporation into double stranded DNA could encompass the emission wavelength, the fluorescence intensity and the fluorescence lifetime. In many examples enhanced fluorescence is observed upon the interaction of a groove binder with double stranded DNA. Haugland in "Handbook of Fluorescent Probes and Research Chemicals," Molecular Probes, Inc., Eugene, Oreg. The underlying principle of this embodiment of the invention is illustrated in FIG. 6. Probes that have a structure according to the principle outlined in FIG. 6 are referred to herein as type VI nucleic acid probes.

7. In this embodiment, the groove binder is fluorescent and serves as the detector dye and the second dye is also fluorescent and serves as the donor dye of a FRET system composed of the groove binder and the second dye. Both dyes modify the fluorescent properties of each other through the FRET process. As a single stranded nucleic acid the nucleic acid probe displays fluorescence upon excitation of either the donor or the groove binder, but excitation of the donor leads to a greatly decreased fluorescence of the donor compared to the fluorescence of the non-conjugated donor. Simultaneously, an increased fluorescence of the groove binder compared to the excitation of the non-conjugated groove binder is observed due to the energy transfer. After hybridization of the nucleic acid probe to a nucleic acid analyte of complementary sequence increased fluorescence is observed upon excitation of the donor due to the interaction of the groove binder with the formed double stranded nucleic acid. The incorporation of the groove binder into the double stranded nucleic acid increases the distance between the groove binder and the donor and therefore reduces the efficiency of the FRET process, which in turn enhances the fluorescence of the donor. In this system the fluorescence of the groove binder is simultaneously decreased when the donor is exited. The underlying principle of this embodiment of the invention is illustrated in FIG. 7. Probes that have a structure according to the principle outlined in FIG. 7 are denoted herein as type VII nucleic acid probes.

In this embodiment the groove binder may or may not change its fluorescent properties upon hybridization of the nucleic acid probe to a complementary target sequence, including shifts in the maxima of the fluorescence excitation and emission spectra and a decrease or increase of the fluorescence intensity. In the case of an increased fluorescence intensity of the groove binder upon hybridization the hybridization of a type VII nucleic acid probe of the invention could potentially not only result in a higher fluorescence intensity of the donor dye upon excitation of the donor dye, but, in addition, also to a higher fluorescence intensity of the groove binder upon excitation of the donor dye, because the groove binder in the hybridized form of the probe can be more efficiently excited through a FRET mechanism upon excitation of the donor dye due to the stronger overall fluorescence of the groove binder.

8. According to this embodiment, the groove binder is fluorescent and serves as the detector dye and the second dye is another fluorescent dye that serves as the acceptor dye of a FRET system composed of the groove binder and the second dye. Both dyes modify the fluorescent properties of each other through the FRET process. As a single stranded nucleic acid the nucleic acid probe displays fluorescence upon excitation of either the groove binder or the acceptor, but excitation of the groove binder leads to decreased fluorescence compared to the excitation of the non-conjugated groove binder and increased fluorescence of the acceptor compared to the excitation of the non-conjugated acceptor. After hybridization of the nucleic acid probe to a nucleic acid analyte of complementary sequence increased fluorescence is observed upon excitation of the groove binder due to the interaction of the groove binder with the formed double stranded nucleic acid. The incorporation of the groove binder into the double stranded nucleic acid increases the distance between the groove binder and the acceptor and therefore reduces the efficiency of the FRET process, which in turn enhances the fluorescence of the groove binder. For many known groove binders the fluorescence is further enhanced due to the intercalation process. An enhancement of the fluorescence due to intercalation in double stranded DNA was observed for many groove binders, see Haugland in "Handbook of Fluorescent Probes and Research Chemicals," Molecular Probes, Inc., Eugene, Oreg., for examples. In this system the fluorescence of the acceptor is simultaneously decreased when the groove binder is excited. The underlying principle of this embodiment is illustrated in FIG. 8. Probes that have a structure according to the principle outlined in FIG. 8 are denoted herein as type VIII nucleic acid probes.

In this embodiment the groove binder may or may not change its fluorescent properties upon hybridization of the nucleic acid probe to a complementary target sequence, including shifts in the maxima of the fluorescence excitation and emission spectra and a decrease or increase of the fluorescence intensity. In the case of an increased fluorescence intensity of the groove binder upon hybridization the hybridization of a type VIII nucleic acid probe of the invention could potentially not only result in a higher fluorescence intensity of the groove binder upon excitation of the groove binder, but, in addition, also to a higher fluorescence intensity of the acceptor dye upon excitation of the groove binder, because the acceptor dye in the hybridized form of the probe can be more efficiently excited through a FRET mechanism upon excitation of the groove binder due to the stronger overall fluorescence of the groove binder.

The nucleic acid probe carries a covalently attached groove binder and two additional covalently attached dyes (9.–10.). The dyes that are not groove binders are covalently linked through a spacer and form a dye pair that is fluorescent.

9. In this embodiment, the dye pair forms an excimer upon exposure to electromagnetic radiation. As a single stranded nucleic acid the nucleic acid probe displays fluorescence that is caused by the excimer. Upon hybridization of the nucleic acid probe to a nucleic acid analyte of complementary sequence decreased fluorescence of the excimer is observed due to the interaction of the groove binder with the formed double stranded nucleic acid. The incorporation of the groove binder into the double stranded nucleic acid increases the distance between the dyes of the excimer pair and therefore reduces the efficiency of the formation of the excimer, which in turn reduces the fluorescence caused by the excimer pair. The underlying principle of this embodiment is illustrated in FIG. 9. Probes that have a structure according to the principle outlined in FIG. 9 are denoted as type IX nucleic acid probes.

10. In this embodiment, the dye pair forms an exciplex upon exposure to electromagnetic radiation. As a single stranded nucleic acid the nucleic acid probe displays fluorescence that is caused by the exciplex. Upon hybridization of the nucleic acid probe to a nucleic acid analyte of complementary sequence decreased fluorescence is observed due to the interaction of the groove binder with the formed double stranded nucleic acid. The incorporation of the groove binder into the double stranded nucleic acid increases the distance between the dyes of the exciplex pair and therefore reduces the efficiency of the formation of the exciplex, which in turn reduces the fluorescence caused by the exciplex pair. The underlying principle of this embodiment is illustrated in FIG. 10. Probes that have a structure according to the principle outlined in FIG. 10 are referred to herein as type X nucleic acid probes.

The design of nucleic acid probes that carry both a first covalently attached dye that has a high affinity to double stranded nucleic acids and at minimum one other dye wherein at least one of the dyes is fluorescent and its fluorescence properties depend on the interaction of the first dye with a double stranded nucleic acid is illustrated in Examples 10 and 11, below.

In Example 10, the fluorescence of the nucleic acid probe (17.2) which carries the covalently attached dyes fluorescein and ethidium was measured as a function of temperature in the range 40° C. to 90° C. The experiments were performed at an excitation wavelength of 470 nm and the emission was recorded at 530 nm and 645 nm, both in the presence and absence of the complementary oligonucleotide d($A_{29}$G) under otherwise identical conditions of probe and buffer concentration. The observed fluorescence intensities are displayed in FIG. 14. The fluorescence intensity of the probe (17.2) in the absence of a complementary sequence is represented by curve A at the emission wavelength 530 nm and by curve A' at the emission wavelength 645 nm. The fluorescence intensity of probe (17.2) in the presence of the complementary oligonucleotide d($A_{29}$G) is represented by curve B at the emission wavelength 530 nm and by curve B' at the emission wavelength 645 nm. The fluorescence of the unhybridized probe decreases slightly with rising temperature in a semi-linear manner at both recorded wavelengths. The fluorescence of the hybridized probe differs considerably from the fluorescence of the unhybridized probe. In the temperature range of 40° C. to approximately 55° C., the fluorescence intensity of the hybridized probe at the emission wavelength 530 nm is roughly 33% higher than the fluorescence intensity of the unhybridized probe. At the emission wavelength 645 nm the fluorescence intensity of the hybridized probe is roughly double as high as the fluorescence intensity of the unhybridized probe. In the temperature range of approximately 55° C. to 65° C., the fluorescence intensity of the hybridized probe shows a strong dependence of the temperature and decreases to the intensity level of the unhybridized probe at both recorded emission wavelengths. The rapid drop in fluorescence intensity is presumably due to the dissociation of the probe from the complement in this temperature range and exhibits the typical characteristics of a melting curve of a double stranded nucleic acid, which is a clear indication of a specific interaction. The $T_m$ value of the probe/complement hybrid, as reflected by the inflection point, is approximately 57° C.

Probe (17.2) is an example of a type II nucleic acid probe of the invention comprising a FRET system established by two fluorescent dyes, the fluorescent intercalator ethidium, which serves as the detector dye and the fluorescent dye fluorescein, which serves as the donor dye of a FRET system. After hybridization of the nucleic acid probe an increased fluorescence of the donor dye fluorescein is observed at 530 nm upon its excitation at 470 nm due to the interaction of the intercalator with the formed double stranded nucleic acid. In addition, probe (17.2) also displays an increased fluorescence of the intercalator ethidium at 645 nm upon excitation of the donor fluorescein at 470 nm, which is potentially related to the increased overall fluorescence of ethidium upon intercalation. The latter feature of probe (17.2) is particularly useful as the excitation and emission wavelengths are separated by 175 nm. Such a big difference between the excitation and emission wavelengths provides the basis for a greatly reduced background in fluorescence measurements, because all other background fluorescence that is excited at 470 nm is highly unlikely to display fluorescence emission at 645 nm. A very large Stokes shift would be required for a background fluorescence dye to emit light at 645 nm upon excitation at 470 nm and therefore any fluorescence that is introduced by spurious contamination with fluorescent impurities is expected to be practically eliminated in measurements with probe (17.2) and similar probes.

In Example 11, the fluorescence of the nucleic acid probes (17.11), (17.20) and (17.21) were measured as a function of temperature in the range of 30° C. to 90° C. The experiments were performed with probe specific excitation and emission wavelengths in the presence as well as in the absence of the complementary oligonucleotide d(AGGGTGGACTTGAAGATGAGCGAAAAA) (SEQ ID NO:11) under otherwise identical conditions of probe and buffer concentration. The recorded fluorescepee intensities in the presence and in the absence of the complementary sequence ($I_F^{hyb}$ and $I_F^{free}$) and their ratios ($I_F^{hyb}/I_F^{free}$) are displayed in FIGS. 15 to 18 as a function of temperature.

Probe (17.11) carries the covalently attached dyes QSY-7 and thiazole orange. The fluorescence intensities of the probe in the absence and in the presence of the complementary sequence at an excitation wavelength of 510 nm and an emission wavelength of 528 nm, and the ratio of both intensities, is displayed in FIG. 15 by the curves A, B and C, respectively. The excitation and emission wavelength match the maxima in the excitation and emission spectra of thiazole orange in this experiment. Both the fluorescence of the unhybridized probe and the fluorescence of the hybridized probe decrease continuously with rising temperature. A distinct decrease of the fluorescence intensity of probes that were singly labeled with the dye thiazol orange with increasing temperature was already observed by Svanvik et al. (2000) Anal. Biochem. 281:26–35, which is incorporated herein by reference in its entirety, and may be attributed to the properties of the dye thiazole orange, as discussed by Nygren et al. (1998) Biopolymers 46: 39–51. The temperature-dependent fluorescence did not mirror a melting curve for probe (17.11) in the presence of the complementary sequence, but since the fluorescence intensity of the hybridized probe became identical to the fluorescence intensity of the unhybridized probe at about 80° C., complete dissociation at 80° C. can be assumed. The fluorescence of the hybridized probe is considerably higher than the fluorescence of the unhybridized probe in the temperature range 30° C. to approximately 75° C. At 30° C. the hybridized probe is approximately 4-fold more fluorescent than the unhybridized probe and a maximum of fluorescence enhancement of approximately 7-fold enhancement upon hybridization is observed in the temperature range of 55° C. to 65° C.

Probe (17.11) is an example of a type I nucleic acid probe of the invention comprising a fluorescent intercalator and a non-fluorescent quencher. The fluorescent intercalator thiazole orange serves as the detector dye and QSY7 serves as the quencher. Upon hybridization of the nucleic acid probe to a complementary sequence increased fluorescence is observed due to the interaction of the intercalator with the formed double stranded nucleic acid. In the unhybridized state the fluorescence of the intercalator is effectively quenched through the presence of the non-fluorescent quencher. In the hybridized state the fluorescence of the intercalator thiazole orange is less effectively quenched.

Probe (17.20) carries the covalently attached dyes thiazole orange and Texas Red. The fluorescence intensities of the probe in the absence and in the presence of the complementary sequence at an excitation wavelength of 510 nm and an emission wavelength of 625 nm, and the ratio of both intensities, is displayed in FIG. 16 by the curves A, B and C, respectively. The excitation wavelength of 510 nm reflects the maximum in the excitation spectrum of thiazole orange and the emission wavelength of 625 nm reflects the maximum in the emission spectrum of Texas Red in this experiment. The fluorescence intensity of the hybridized probe is higher than the fluorescence intensity of the unhybridized probe at all temperatures and both fluorescence intensities decrease continuously with rising temperature. The fluorescence enhancement that is obtained upon hybridization is approximately 1.5-fold at 30° C. and the maximum enhancement is approximately 2-fold in the temperature range 58° C. to 68° C.

Probe (17.20) is an example of a type III nucleic acid probe of the invention comprising a FRET system established by two fluorescent dyes, the fluorescent intercalator thiazole orange that serves as the detector dye and the second dye being the fluorescent dye Texas Red that serves as the acceptor dye of a FRET system. After hybridization of the nucleic acid probe an increased fluorescence of the acceptor dye Texas Red is observed at 625 nm upon the excitation of the intercalator thiazole orange at 510 nm due to the interaction of the intercalator with the formed double stranded nucleic acid. Most likely the increase in the fluorescence intensity of Texas Red is due to the stronger fluorescence of thiazole orange in the hybridized state for this probe. Probe (17.20) is assumed to be a very useful probe due to its very high fluorescence intensity and the large separation of the excitation and the emission wavelength that differ by 115 nm, which provides the basis for a greatly reduced background in fluorescence measurements.

Probe (17.21) carries the covalently attached dyes thiazole orange and MDCC (7-diethylamino-3-((((2-maleimidyl)ethyl)amino)carbonyl)coumarin). The fluorescence intensities of the probe in the absence and in the presence of the complementary sequence and the ratio of both intensities, is displayed in FIG. 17 and FIG. 18 by the curves A, B and C, respectively. In FIG. 17, an excitation wavelength of 510 nm and an emission wavelength of 525 nm were employed, reflecting the maxima in the excitation and emission spectra of thiazole orange in this particular experiment. In FIG. 18, an excitation wavelength of 420 nm and an emission wavelength of 525 nm were employed, the excitation wavelength reflecting the maximum in the excitation spectrum of MDCC and the emission wavelength reflecting the maximum in the emission spectrum of thiazole orange this particular experiment. With both excitation wavelengths the fluorescence intensity of the hybridized probe is higher than the fluorescence intensity of the unhybridized probe over the whole temperature range of 30° C. to approximately 75° C. and in both cases the fluorescence intensities of the hybridized probe and the unhybridized probe decrease continuously with rising temperature. With an excitation at 420 nm the fluorescence enhancement that is obtained upon hybridization is approximately 1.2-fold at 30° C. and the maximum enhancement is approximately 2-fold in the temperature range 55° C. to 67° C. With an excitation at 510 nm the fluorescence enhancement that is obtained upon hybridization is approximately 2-fold at 30° C. and the maximum enhancement is approximately 4-fold.

Probe (17.21) is an example of a type II nucleic acid probe of the invention comprising a FRET system established by two fluorescent dyes, the fluorescent intercalator thiazole orange serves as the detector dye and the fluorescent dye MDCC serves as the donor dye of a FRET system. After hybridization of the nucleic acid probe an increased fluorescence is observed at 528 nm upon excitation of the probe at 420 nm or 510 nm due to the interaction of the intercalator with the formed double stranded nucleic acid. Most likely the increase of the fluorescence of thiazole orange upon intercalation allows for a higher energy transfer in this probe.

In yet another embodiment of the present invention, the nucleic acid probe is designed to carry both a covalently attached pH sensitive dye and at a minimum one other covalently attached dye. At least one of the dyes is fluorescent and the fluorescence intensity is modulated by the pH of the medium employed in the assay. The pH sensitive dye and the fluorescent dye form a FRET system. Under certain conditions of pH the probe is fluorescent, whereas upon a change of the pH, the pH sensitive dye becomes an effective quencher and the fluorescence of the probe is no longer measurable or drops down to a low intrinsic background level. Probes that carry both a covalently attached pH sensitive dye and at minimum one other covalently attached dye are denoted as type XI nucleic acid probes.

pH-sensitive dyes are characterized by a change in their absorption characteristics upon a change of the pH of the medium. Typical examples of pH-sensitive dyes are the common pH-indicators. Examples of such pH-indicators include, but are not limited to, methylorange which changes color from red to yellow-orange upon a change of the pH from <3 to >4.5, bromothymolblue which changes color from yellow to blue upon a change of the pH from <6to >7.5, thymolblue which changes color from yellow to blue upon a change of the pH from <8 to >9.5, and phenolphthalein which changes color from colorless to violet upon a change of the pH from <8 to >10. All of these dyes and other pH-sensitive dyes can potentially be applied in the probes of the present invention if they are covalently attached to the probe together with a second fluorescent dye.

pH-sensitive nucleic acid probes can be obtained by incorporation of a modified trityl group as one of the dyes of the probe. For instance, a DMT (dimethoxytrityl) group can be employed together with a fluorescent dye, as exemplified in structures (20) and (21) below. In an acidic medium the DMT group is converted to the cationic species (20), which has a considerable absorption at approximately 500 nm. Under these conditions, the nucleic acid probe displays minimal or no fluorescence because the DMT group acts as an efficient quencher of the fluorescent dye. Under neutral or basic conditions the DMT group is reconverted to its OH-form (structure (21)), which has essentially no absorption at 500 nm. In this form the nucleic acid probe is highly fluorescent, because the fluorescence of the second dye is no longer quenched. Modified trityl groups were described as pH sensitive fluorescence labels by Shchepinov et al. (2000) Tetrahedron Lett. 41:4943–4948, which is incorporated herein by reference in its entirety. This reference discloses modified trityl groups as pH-sensitive fluorescent dyes, but does not incorporate them into oligonucleotides, although applications with oligonucleotides are proposed. The probes disclosed herein, however, are more versatile, in that almost any pH-sensitive chromophore or dye can be employed as the pH-sensitive element of the probe, regardless of whether the chromophore or dye has an intrinsic fluorescence or not. This allows the introduction of desirable properties such as photostability, a very high brightness and a high quantum yield into the probe by the selection of the fluorescent dye, which is not limited by the requirement of being fluorescent. Probes that carry both a covalently attached trityl group and a fluorescent dye are illustrated in FIG. 11.

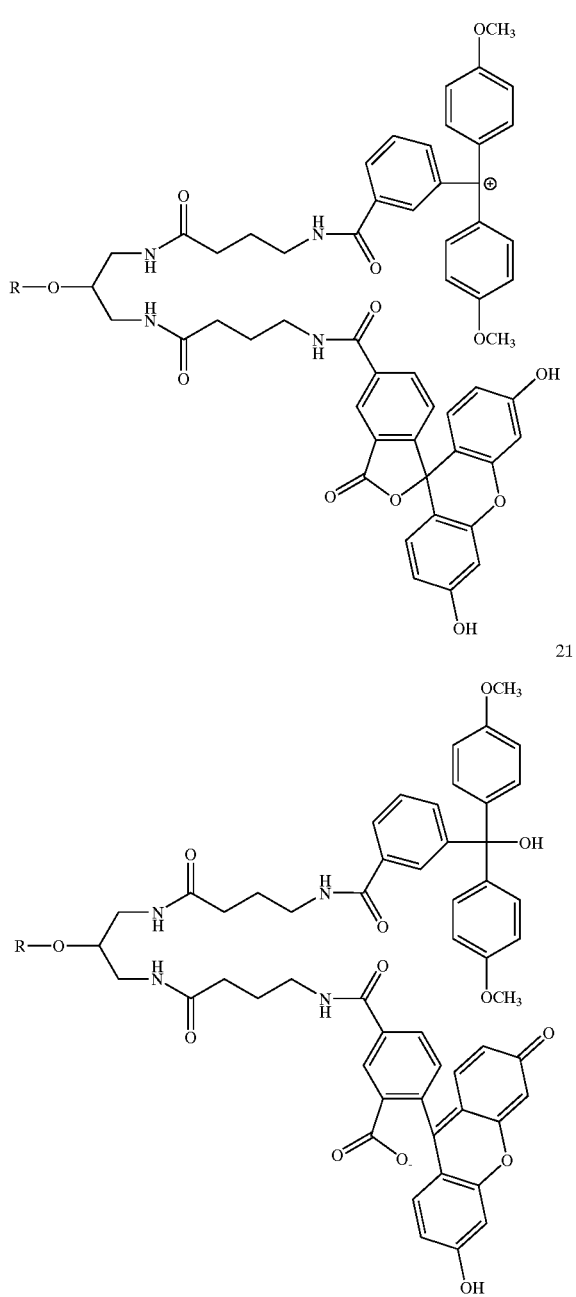

Applications in Homogeneous Assays

In one embodiment of the present invention, a nucleic acid probe as described above, is used in homogeneous assays to detect or quantify nucleic acid targets. In such assays, a fluorescent signal is generated upon the presence of a complementary nucleic acid sequence in the analyte. The fluorescent signal is monitored and quantified with fluorescence detectors, such as fluorescence spectrophotometers, commercial systems that allow the monitoring of fluorescence in PCR reactions, e.g. instruments produced by Perkin-Elmer Applied Biosystems, Foster City, Calif., or LIGHTCYCLER™ instruments of Roche Diagnostics, Indianapolis, Ind., or, in some instances, by the human eye. With type I, II, III, VI, VII or VIII nucleic acid probes a fluorescent signal is generated or increased in the presence of a complementary sequence in the target nucleic acid analyte. With type IV, V, IX or X nucleic acid probes a fluorescent signal is decreased in the presence of a complementary sequence in the target nucleic acid analyte, see FIGS. 1–10 for an illustration.

In one embodiment, a homogeneous assay is conducted without the addition of reagents, such as buffers and other non-reactive ingredients. Other non-reactive ingredients including, but are not limited to, EDTA, magnesium salts, sodium chloride, potassium chloride, inorganic phosphates, BSA (bovine serum albumin), gelatin, DMF, DMSO, urea, chaotropic salts or other non-reactive ingredients known to those skilled in the art which are commonly employed in nucleic acid based diagnostic assays can also be used with this method. In this embodiment of the invention, the nucleic acid probe hybridizes with a complementary nucleic acid sequence, if present in the target, to form a stretch of double stranded DNA. In turn one of the dyes, which is covalently attached to the nucleic probe, interacts with the stretch of double stranded DNA, resulting in the generation of a fluorescent signal. With appropriate target standards and concentration versus signal standard curves the method can easily be used to quantitate the target. In addition to single stranded target nucleic acids, double stranded target nucleic acids can also be detected by the nucleic acid probe following denaturation. Targets that can be specifically detected and/or quantified with this method include, but are not limited to, plasmid DNA, cloning inserts in plasmid DNA, RNA transcripts, ribosomal RNA, PCR amplicons, restriction fragments, synthetic oligonucleotides, as well as any other nucleic acids and oligonucleotides.

In another particular embodiment of the invention a homogeneous assay is conducted simultaneously with a PCR reaction. With this type of assay all components that are necessary to conduct a PCR reaction on the target nucleic acid analyte are added simultaneously with the nucleic acid probe and the target. The components of the PCR reaction include primers, a thermostable DNA polymerase, an aqueous buffer, magnesium chloride and deoxynucleotide triphosphates, and may also include other non-reactive ingredients, including, but not limited to, salts, BSA, gelatin, DMSO, chaotropic salts, as discussed above. As the PCR reaction progresses increasing amounts of double stranded PCR amplicons are formed which are denatured within the course of a PCR cycle. In these assays, the specific nucleic acid probe contains a stretch of nucleic acid sequence that is complementary to a stretch of nucleic acid sequence on the formed amplicon. Upon hybridization of the nucleic acid probe to its complementary stretch of nucleic acid sequence on the single stranded amplicon a fluorescent signal is generated in the annealing step of the PCR cycle that is proportional to the amount of amplicon formed. In the course of the elongation of the primer on the single stranded amplicon the nucleic acid probe is displaced from the amplicon, either through the 5'-3'-exonucleolytic activity of the polymerase, which removes the nucleic acid stepwise one nucleotide after the other from the 5'-end of the probe, or through thermal denaturation in the elongation step of the PCR reaction.

The principle of homogeneous assays conducted simultaneously with a PCR reaction is illustrated with type I nucleic acid probes in FIG. 12. With reference to FIG. 12, after combining the nucleic acid probe with two standard sequence specific DNA primers and the double stranded DNA to be amplified in the appropriate reaction medium, denaturation and annealing, a fluorescent signal is generated because the nucleic acid probe anneals to the denatured DNA, resulting in increased fluorescence. After the primer elongation step the DNA is in doubled stranded form and fluorescence is not observed or minimized (to the residual low fluorescence of the nucleic probe). In the next cycle of the PCR reaction the fluorescent signal is increased at the annealing step, because the number of single stranded amplicons has doubled in the reaction. This scheme continues with increasing cycle number displaying increased fluorescence that is proportional to the amount of amplicon formed.

In another variation of this embodiment of the invention, the nucleic acid probe acts as one of the primers of the PCR reaction. In this variation the specific nucleic acid probe is incorporated in the PCR amplicon upon the progression of the reaction. Upon annealing of the nucleic acid probe that acts as the primer to the single stranded amplicon a fluorescent signal is generated, which can be recorded in the annealing step of the PCR reaction and which is proportional to the amount of amplicon formed. This method is more versatile than the method described above because only one additional primer is required. An additional advantage of this variation of the method is that the amplicon product of the assay carries the covalently attached dyes that were part of the nucleic acid probe in one strand and can be further employed as nucleic probes themselves, e.g. in microarray applications, as described below.

This variation of the method of this invention is illustrated in FIG. 13. With reference to FIG. 13, after combining the nucleic acid probe with one standard sequence specific DNA primer and the double stranded DNA to be amplified in the appropriate reaction medium, denaturation and annealing, a fluorescent signal is generated when the nucleic acid probe acts as one of the primers of the PCR reaction because it anneals to the denatured DNA, which results in increased fluorescence. After the primer elongation step the DNA is in doubled stranded form, but contains the nucleic acid probe incorporated in the sequence and a fluorescent signal is still observable. In the next cycle of the PCR reaction the fluorescent signal is increased at the annealing step, because the number of single stranded amplicons has doubled in the reaction. This scheme continues with increasing cycle number displaying increased fluorescence that is proportional to the amount of amplicon formed.

The described method allows the monitoring of a PCR reaction in real time, which has several benefits compared to a conventional end point analysis, e.g. the analysis of PCR reactions through gel electrophoresis. Firstly, the method allows the direct observation of the reaction, which provides a quality control of the PCR. Since the success of any PCR reaction, especially on complex targets like the human genome, is dependent on the exact nature of the target structure and not automatically guaranteed, a quality control early in the process is highly desirable. PCR reactions that fail to produce an amplicon could be discarded without further analysis, which provides great savings regarding the amount of post-PCR handling and materials usage to the investigator. Secondly, many PCR reactions not only provide specific amplicons, but also non-specific products from incorrect annealing of the primers to the target. Typically, the non-specific products require a higher cycle number than the specific product to become abundant in the reaction. Monitoring the reaction in real time allows the investigator to stop the reaction at a cycle number that provides enough specific amplicon and does not provide impeding quantities of non-specific amplicons which eliminates the need to perform a careful optimization of a PCR to obtain specific amplicons. This is particularly valuable in high-throughput labs as the amount of necessary optimization work can easily exceed the amount of work involved with the final generation of the amplicon product.

The doubly labeled probes prepared with the diene/amino linker (14) are suitable for PCR applications. They are perfectly stable under the conditions of PCR temperature cycling and can be employed as primers of the PCR. Example 12 demonstrates the stability of the nucleic acid probe (17.13) which carries the covalently attached dyes TAMRA and thiazole orange. The probe is dissolved in a PCR buffer and subjected to 40 temperature cycles in a PCR machine. The probe is analyzed by HPLC and compared to a reference sample. Virtually no difference in the overall purity and in the impurity profile was found between the probe that was subjected to the temperature cycling conditions and the reference sample. This result demonstrates that the covalent linkage between the nucleic acid probe and the attached dyes as introduced with linker (14) is stable under the conditions of PCR. It also demonstrates the stability of the attached dyes TAMRA and thiazole orange under such conditions.

Example 13 describes several PCR reactions employing the nucleic acid probes of the invention as primers in the PCR reaction. Specific PCR products of the expected length were obtained with a variety of probes that were employed as one of the primers of the PCR. Different combinations of dyes were included and PCR products that correspond to 3 different human genes were obtained. The synthesis of the PCR products was verified by agarose gel electrophoresis. Example 13 demonstrates that the nucleic acid probes of the invention can be employed as primers in a PCR reaction and that the presence of such probes in a PCR does not inhibit the preparation of specific amplification products.

Example 14 describes the application of the probes of the present invention in several PCR reactions that were monitored in real time through the measurement of the fluorescence of the probes. Pre-amplified DNA was used as a target nucleic acid in this example. In one of the reactions the nucleic acid probe (17.21), which carries the covalently attached dyes MDCC and thiazole orange, was employed in the detection of a nucleic acid sequence that corresponds to a part of the human adenine deaminase (ADA) gene. The probe was excited at 490 nm and the monitoring of the PCR reaction was performed at 530 nm. The observed fluorescence is displayed as a function of the PCR cycle number in FIG. 19. After some cycles in which a low overall fluorescence was monitored, a sharp rise of the fluorescence within 4–5 cycles was observed indicating the formation of the PCR product. In another example, the nucleic acid probe (17.24) was employed in the detection of a nucleic acid sequence that corresponds to a part of the human prothrombin gene. The probe was excited at 490 nm and the monitoring of the PCR reaction was performed at 530 nm. A similar result as obtained with nucleic acid probe (17.21) was obtained and the observed fluorescence is displayed as a function of the PCR cycle number in FIG. 21. In yet another example, nucleic acid probe (17.14), which carries the covalently attached dyes thiazole orange and Texas Red was employed in the detection of the same ADA nucleic acid sequence that was targeted with probe (17.21). The probe was excited at 490 nm and the monitoring of the PCR reaction was performed at 625 nm in this case. A similar result as obtained with nucleic acid probes (17.21) and (17.24) was obtained, indicating the formation of the PCR product by a rise of the observed fluorescence after some initial cycles with low observable fluorescence. The formation of specific PCR products of the expected size was verified by agarose gel electrophoresis for each of the described examples. Example 14 demonstrates the capacity of the nucleic acid probes of the invention for the detection of nucleic acid targets in homogeneous assays and in the detection of PCR products in real-time.

In all homogeneous assays that are conducted simultaneously with a PCR reaction, the fluorescent signal can be used to determine the amount of target nucleic acid analyte present prior to the start of the PCR reaction. The method is based on the monitoring of the fluorescence signal in all annealing steps of the subsequent cycles of the PCR reaction. In the initial cycles of the PCR a very low fluorescence intensity is observed because the quantity of the amplicon formed does not support a measurable fluorescence output from the assay. After the initial cycles, as the amount of formed amplicon increases, the fluorescence intensity increases to a measurable level and reaches a plateau in later cycles when the PCR enters into a non-logarithmic phase. Through a plot of the fluorescence intensity versus the cycle number, the specific cycle at which a measurable fluorescence signal is obtained from the PCR reaction can be deduced and used to back-calculate the quantity of the target before the start of the PCR. The number of the specific cycles that is determined by this method is named CT (cycle threshold). The method is described in detail in Heid et al. (1996) Genome Methods 6:986–94, with reference to hydrolysis probes. It can be used effectively to quantify target nucleic acid analytes with a very large dynamic range, at least a >100,000-fold range.

Example 15 describes the application of the nucleic acid probes of the present invention in the quantification of a target sequence. Probe (17.21) was employed in a series of PCR reactions that were conducted in the presence of different amounts of the target nucleic acid sequence. A serial dilution of a pre-amplified target sequence was used for this purpose. The target sequence relates to a part of the human adenine deaminase (ADA) gene. The probe was excited at 490 nm and the monitoring of the PCR reaction was performed at 530 nm. The observed fluorescence is displayed as a function of the PCR cycle number in FIG. 20. Curves A and B in the figure relate to the amplification of approximately 0.1% of a pre-formed PCR product. After some cycles in which a low overall fluorescence the observed fluorescence rises sharply indicating the formation of the PCR product. The application of a threshold for the fluorescence in the first cycles leads to a cycle number where the observed fluorescence rises above the threshold CT. CT-values of 12.3 and 12.1 were observed for curves A and B. Curve C in the figure relates to the amplification of approximately 0.01% of a pre-formed PCR product. A CT-value of 15.5 was observed for curve C. Curves D and E in FIG. 20 relate to the amplification of approximately 0.001% of a pre-formed PCR product. CT-values of 19.7 and 19.9 were observed for curves D and E. The curves F and G in FIG. 20 relate to the amplification of approximately 0.0001% of a pre-formed PCR product. CT-values of 22.9 and 25.2 were observed for curves F and G. The observed cycle threshold values CT correlate well with the geometrical progression of the PCR reaction. Assuming that the same amount of hybridized probe is necessary to generate a fluorescence signal that matches the threshold in each of the experiments a 10-fold amplification is required to compensate for a 10-fold reduced number of target copies in the reaction. A 10-fold amplification corresponds to 3.3 cycles of the PCR at 100% amplification efficiency, which matches the observed average difference between the CT-values for 10-fold diluted targets, i.e. an average difference of 3.2 between the CT-values of curves A/B and C, an average difference of 4.3 between the CT-values of curves C and D/E, and an average difference of 4.25 between the CT-values of curves D/E and F/G. The slightly higher values that were observed can be explained by a PCR efficiency that is slightly below 100%. The formation of specific PCR products of the expected size was verified by agarose gel electrophoresis for each of the described experiments. Example 15 demonstrates the utility of the nucleic acid probes of the invention for the quantification of nucleic acid targets in homogeneous assays and in real-time PCR based assays.

The methods described above can be applied to conventional PCR reactions with a DNA target nucleic acid analyte as well as to many variations thereof, including, but not limited to, RT-PCR (reverse transcription PCR) with RNA nucleic acid analytes, site specific mutagenesis using PCR, inverse PCR reactions and other variations. The methods are useful to detect and quantify genetic variations in the target nucleic acid analyte using established PCR techniques, see McPherson et al. eds., in "PCR A Practical Approach," Oxford University Press, and Innis et al. eds., in "PCR Applications, Protocols for Functional Genomics," each of which is incorporated herein by reference in its entirety. In particular, an allele specific PCR reaction can be performed to detect single nucleotide polymorphisms as described in Newton et al. (1989) Nucleic Acids Res. 17:2503–2516, and Sommer et al. (1989) Mayo Clin. Proc. 64:1361–1372, each of which is incorporated herein by reference.

In another particular embodiment of the invention, a homogeneous assay is conducted simultaneously with an in vitro transcription assay. In this type of assay, a plasmid or another source of DNA sequence that carries a promoter sequence provides the formation of single stranded RNA transcripts. The assay typically contains the nucleic acid probe and the source of DNA, a RNA polymerase, e.g. T7 RNA polymerase, an aqueous buffer, ribonucleotide triphosphates and other non-reactive ingredients. The other non-reactive ingredients include, but are not limited to, dithiothreitol, dithioerythrol, magnesium chloride, salts, RNAse inhibitors and other ingredients. In the course of the assay multiple RNA transcripts are formed from a single DNA source template. The transcript contains a stretch of nucleic acid sequence, which is complementary to a stretch of nucleic acid sequence on the probe. Upon hybridization of the nucleic acid probe to the transcript a fluorescent signal is generated, which is proportional to the amount of transcript formed. This embodiment of the invention is illustrated schematically in FIG. 13. A homogeneous transcription assay with an oligonucleotide probe that contains the covalently attached intercalator oxazol yellow has been described by Ishiguro et al. (1996) Nucleic Acids Res. 24:4992–97 (1996), which is incorporated herein by reference. However, in the approach described by Ishiguro et al., the described fluorescence signal was of rather low intensity and needed to be measured against a fluorescence background of a comparable intensity.

Homogeneous assays in accordance with this invention can be multiplexed, i.e. more than one target nucleic acid analyte can be detected in one assay. In a multiplex assay, more than one specific nucleic acid probe, which differ in the nature of their covalently attached dyes, is added to the mixture to be assayed. The dyes are chosen to produce distinguishable fluorescent signals from each specific nucleic acid probe. The signals of the different dye combinations of the nucleic acid probes are recorded simultaneously to detect and/or quantify the corresponding target nucleic acids at the same time. Multiplexing greatly reduces the cost of analysis and can tremendously increase throughput in high volume settings.

Applications in Nucleic Acid Microarrays

In another embodiment of the present invention, a nucleic acid probe as described herein is employed in assays that are conducted on nucleic acid microarrays to detect or quantify nucleic acid targets. In such assays, a fluorescent signal is generated on a nucleic acid microarray upon the presence of a complementary nucleic acid sequence in the analyte. Nucleic acid microarrays, also called nucleic acid chips, consist of ordered arrays of nucleic acids that are covalently attached to a solid surface, see Schena, ed., in "DNA Microarrays A Practical Approach," Oxford University Press, and Marshall et al. (1998) Nat. Biotechnol. 16:27–31, each of which is incorporated herein by reference, for a comprehensive description of nucleic acid microarrays. The fluorescent signal that is generated in the assay can be monitored and quantified with fluorescence detectors, including fluorescence imagers, e.g. commercial instruments supplied by Hitachi Corp., San Bruno, Calif. or confocal laser microscopes (confocal fluorescence scanners), e.g. commercial instruments from General Scanning, Inc., Watertown, Mass. With type I, II, III, VI, VII or VIII nucleic acid probes a fluorescent signal is generated or increased upon the presence of a complementary sequence in the target nucleic acid analyte. With type IV, V, IX or X nucleic acid probes a fluorescent signal is decreased upon the presence of a complementary sequence in the target nucleic acid analyte.

In assays that are conducted on nucleic acid microarrays the target nucleic acid analyte may be a mixture of nucleic acid sequences, consisting of up to hundreds of nucleic acid sequences, and in some instances of up to tens of thousands of nucleic acid sequences. This instance particularly applies to expression analysis, where many or all mRNA sequences that are present in a biological system, e.g. a certain cell type from a cell culture, are analyzed, see Hunt et al., eds., in "Functional Genomics A Practical Approach," Oxford University Press, for a comprehensive description of expression analysis, which is incorporated herein by reference. Typically, the mRNA sequences are amplified by reverse transcription PCR with universal primers prior to their use as analytes in the assay. In this setting all nucleic acid sequences present in the analyte are simultaneously applied to the microarray for analysis, thus allowing the interaction of all nucleic acid sequences of the analyte with all nucleic acids that are present on the array. In other instances, the target nucleic acid analyte contains a limited number of up to a hundred nucleic acid sequences and in some instances only one nucleic acid sequence. In this case the limited number of sequences typically contain more than one stretch of specific nucleotide sequence to be analyzed, e.g. more than one single nucleotide polymorphism. The nucleic acid sequences of this setting may be amplified by PCR with the aid of specific primers prior to their analysis on the microarray.

Generally, in analysis on microarrays the fluorescent signals generated are converted to sequence specific results through the known relation of the location of a spot on the array and the nucleotide sequence attached to it.

In a particular embodiment of the invention mRNA molecules from a biological source are detected and/or quantified. Typically, the mRNA molecules are converted to cDNA molecules and/or further amplified by PCR to provide the target nucleic acid analyte to be applied in the assay on the microarray. In many instances, such assays are conducted with mRNA samples obtained from a biological system under different environmental conditions, such as exposures to varying concentration of a drug candidate or mixtures of drug candidates, which can provide data on the efficacy, the safety profile, the mechanism of action and other properties of the drug candidates that are required in drug development. In a particular variation such samples are differentially labeled during the reverse transcription and/or the PCR process to allow their simultaneous application in the microarray based assay and therefore a direct comparison of the quantity of specific mRNA obtained under the different environmental conditions applied to the biological system. This technique is known as "differential display," see Hunt et al., eds., in "Functional Genomics A Practical Approach," for a comprehensive description of this method. Differential display is a technique useful to compare the state of a biological system before and after exposure to artificial conditions, especially exposure to drugs and drug candidates to evaluate pharmacogenomic properties, or the exposure to pathogens and their toxins. This technique can be extended to a large variety of other assays that compare biological systems, including, but not limited to the comparison of cells from different tissues of an organism, e.g. different tissues from a human body and the comparison of similar organisms, e.g. bacterial strains, and other assays.

In the context of the present invention, the labeling of the cDNA molecules of the analyte is performed with a nucleic acid probe that acts as one of the unspecific primers in a reversed transcription PCR reaction prior to the analysis. The product of such a PCR reaction is a mixture of cDNA amplicons, each of which contains the dyes of the probe and therefore represents a nucleic acid probe by itself. The resulting mixture of amplicons is then exposed under hybridization conditions to a microarray with an ordered pattern of known oligonucleotide sequences that contain stretches of complimentary nucleotide sequence to some or all of the probes. Upon hybridization on the array a fluorescent signal is generated at those spots of the array that contain stretches of nucleotide sequence which are complementary to nucleotide sequences in the probes indicating the presence of such sequences in the mRNA that was used to generate the probes. In the differential display technique two sets of labeled amplicons, generated as described above, with differentially labeled nucleic acid probes as primers of the reverse transcription PCR reaction are used simultaneously on the microarray. Each set of amplicons is labeled with a set of dyes unique to the corresponding nucleic acid probe in this setting. The hybridization of the mixture of analytes results in specific fluorescence signals on the array that allow the comparison of the mRNA populations of the original samples.

In another embodiment of the invention, the nucleic acid probes to detect or quantify nucleic acid targets in assays that are conducted on nucleic acid microarrays are derived from genomic DNA in order to analyze for the presence or absence of polymorphisms in the genomic DNA. The polymorphisms can be deletions, insertions, or base substitutions or other polymorphisms of the genomic DNA. Typically the polymorphisms are single nucleotide polymorphisms (SNPs), i.e. single base substitutions in the genomic DNA.

In one case, the genomic DNA is amplified in one or more PCR reactions with nucleic acid probes, as defined herein, that act as specific primers of the PCR. The resulting amplicons of such PCR reactions contain the primers in their sequence and thus the dyes, which were incorporated into the nucleic acid probe. The amplicons themselves are therefore nucleic acid probes, as defined in this invention. The amplicons contain one or more polymorphic sites of interest.

The microarray that is used in the assay contains ordered nucleic acid sequences that are complementary and/or partly complementary to the polymorphic sites in such a manner that the polymorphic sites can be identified in the assay. Typically, the microarray contains sequences, which differ in one nucleotide corresponding to the polymorphic site and allow the discrimination of the possible variations at the polymorphic site upon hybridization of the amplicons. A sequence that is fully complementary will generate a fluorescent signal, whereas a sequence with a corresponding possible variation of the polymorphism, in many cases a single nucleotide variation, will not hybridize as efficiently as the fully complementary sequence under the conditions of the assay, and therefore will generate a weaker fluorescent signal or no fluorescent signal at all. The employed array typically contains more than one or all possible variations of nucleotide sequence corresponding to the polymorphic site of interest, e.g. both variations of a SNP, and therefore allows the detection and/or quantitation of more than one or all variations of the polymorphic site, e.g. both variations of a SNP. Therefore, in SNP detection typically both homozygote and heterozygote variations of the SNP can be detected.

This method can be employed with specific primers, which are nucleic acid probes that carry the same set of covalently attached dyes, or with specific primers, that are nucleic acid probes which carry differentially labeled sets of covalently attached dyes. With respect to the latter variation polymorphisms from different genes may be individually labeled. The PCR reactions that employ the nucleic acid probes as primers may be performed individually, or as multiplexed PCR reactions.

In yet another variation, the genomic DNA is amplified in one or more PCR reactions with unmodified specific primers, which are not labeled. The resulting amplicons contain the polymorphisms of interest and are employed in an assay with a microarray that contains ordered spatially arranged nucleic acid probes in accordance with this invention. The nucleic acid probes contain stretches of nucleotide sequences that are complementary and/or partly complementary to the polymorphic sites in such a manner that the polymorphic sites can be identified in the assay. In this variation the assay is conducted similarly to the assay described above for unlabeled nucleotide sequences on the array and labeled PCR amplicons and all the variations thereof as described above.

The use of the nucleic acid probes of this invention in assays that are conducted on nucleic acid microarrays to detect or quantify nucleic acid targets offers several advantages compared to other methods that are based on microarrays. The advantages are based on the very low fluorescent background of the nucleic acid probes defined herein. In particular, type I, II, III, VI, VII and VIII nucleic acid probes have a very low intrinsic fluorescence and are in some instances essentially non-fluorescent.

In a conventional assay that is based on microarrays with fluorescent methods, the array needs to be stringently washed in order to remove non-hybridized fluorescent nucleotide sequences that interfere with the detection of the fluorescent signal and increase the signal to noise ratio in the assay. In these assays a delicate balance must be achieved with respect to the stringency of the washing. A stringency that is too high removes correctly hybridized sequences, which decreases positive signals in the assay, and a stringency that is too low increases false positive signals leading to unreliable and erroneous results. Often, unspecific absorption of fluorescent nucleic acids on the surface of microarrays is a major problem in these assays as the background fluorescence generated from such absorption processes can't be removed effectively. This is particularly true for surfaces modified with chemical agents that provide aminated surfaces. An aminated surface provides a positively charged matrix that attracts all negatively charged nucleic acid species in a sample in a non-specific manner.

The nucleic acid probes described herein require less stringent washes because the probes generate positive signals if and only if they are correctly hybridized on the array. Under optimized conditions the nucleic acid probes can be applied even without washes, because the probes themselves are non-fluorescent and do not produce a background. This feature greatly diminishes the cost of microarray based assays, increases the signal to noise ratio of the assay and therefore its reliability and allows the analysis of smaller and/or more dilute nucleic acid target samples.

Applications of pH Sensitive Probes

In another embodiment of the instant invention, type XI nucleic acid probes derivatized with a pH sensitive dye are used to provide a switchable fluorescence signal in an assay. Upon hybridization with a complementary nucleic acid analyte a fluorescence signal is generated that is switchable, meaning it can be turned on and off by an adjustment of the pH of the mixture. This is particularly useful on microarrays, especially in competitive assays, e.g. in differential display techniques. In this variation, two 2 differentially labeled nucleic acid probes with pH sensitive quenchers can be employed as primers in reverse transcription assays to generate differentially labeled populations of cDNAs from e.g. two different biological samples obtained under different environmental conditions from the same organism or cell culture. One of the probes can carry a quencher that becomes effective under higher pH conditions, e.g. pH 7–10 (basic quencher), and the other probe can carry a pH sensitive quencher that becomes effective under lower pH conditions, e.g. at pH 4–7 (acidic quencher). Upon hybridization on a microarray in a differential display technique, as described above, the fluorescent signals on the microarray can be switched in response to the pH of the hybridization buffer. At acidic pH, e.g. at pH 5, the fluorescence from the probe that carries the acidic quencher can be measured and the fluorescence from the probe that carries the basic quencher is non-detectable. At basic pH, e.g. pH 9, this situation is reversed, as the fluorescence from the probe that carries the acidic quencher is non-detectable and the fluorescence from the probe that carries the basic quencher is measurable. At neutral pH, both probes provide signals. The switching of the signals allows a clear distinction of the signals that result from both types of probes on the array and avoids all problems that are associated with crosstalk from two different dyes or dye combinations that are commonly employed in differential display techniques.

In another embodiment type XI nucleic acid probes with pH sensitive dyes are used as pH sensitive fluorescence sensors to detect variations in pH within a sample. Samples include, but are not limited to, environmental samples, cellular or other bodily fluids, biological membranes and other samples. In this embodiment the nucleic acid part of the nucleic acid probe provides water solubility to the dye combination that is covalently attached with the dyes. This allows the use of dye combinations that can't be applied as regular pH indicators due to solubility problems in water. The method can also be used with nucleic acid conjugates, e.g. protein, peptide or lipid conjugates. The conjugation transfers additional specificity to the probes, e.g. a specificity for membranes from lipophilic conjugation, or a specificity for antigens from the conjugation of an antibody.

The following examples are provided for illustrative purposes only and are not intended to limit the scope of the invention.

EXAMPLES

Example 1

Synthesis of Bifunctional Linker (13): 1-(N4-(9-fluorenylmethoxycarbonyl) aminobutyryl)-amino-3-(N4-(4-methoxytrityl)-aminobutyryl)-aminopropan-2-ol cyanoethoxy-diisopropylaminophosphoramidite The synthesis of bifunctional linker 13 is outlined in Scheme 1.

laid with ethyl acetate (~2.5 L), mixed and the two phases were allowed to separate. The organic phase was washed with water (3×500 mL), dried over $Na_2SO_4$ and evaporated to dryness.

The residue obtained was dissolved in boiling ethanol (150 mL) and allowed to crystallize at room temperature. The precipitate was filtrated and washed with ethanol (2×20 mL). Again the precipitate was dissolved in boiling ethanol (100 mL), allowed to crystallize at room temperature, filtrated and washed with ethanol (2×10 mL). The residue was dried in vacuo yielding 20.4 g (62.5%) of the product.

N4-(9-fluorenylmethoxycarbonyl)-aminobutyryl-p-nitrophenyl ester. N4-(9-fluorenylmethoxycarbonyl) aminobutyric acid (18.6 g, 57 mmol), 4-nitrophenol (8.7 g,

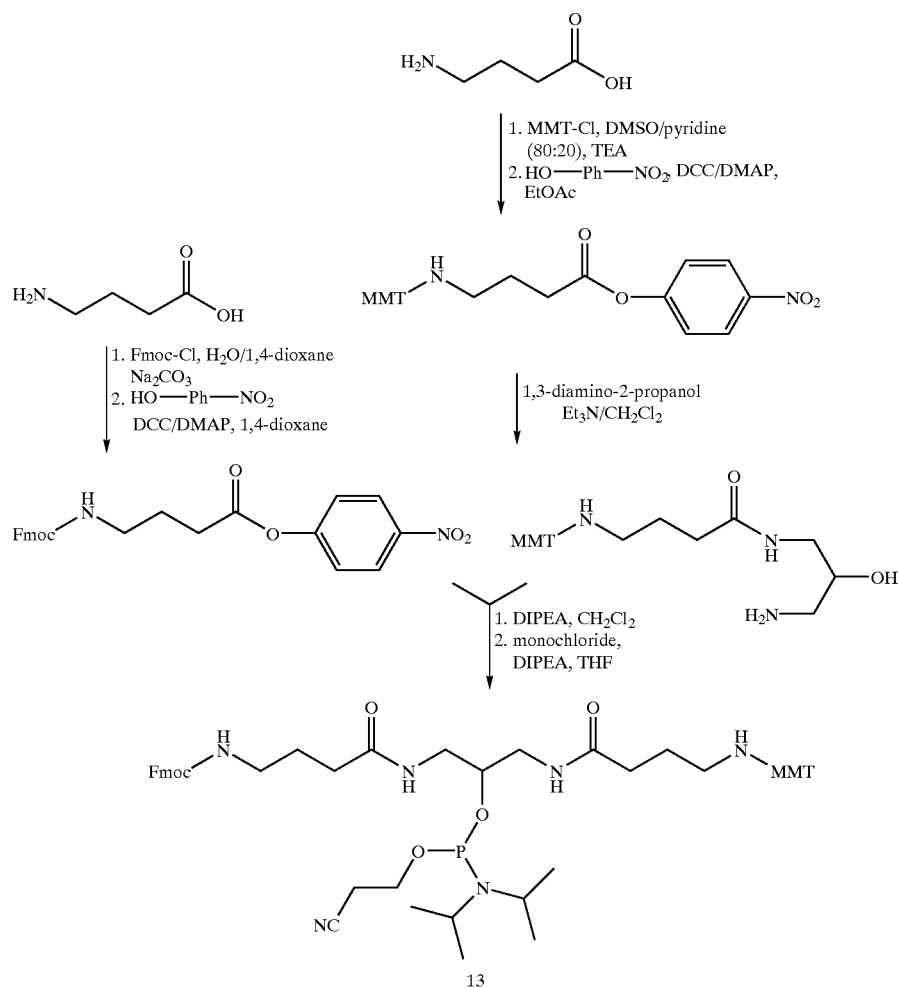

Scheme 1

13

N4-(9-fluorenylmethoxycarbonyl)aminobutyric acid. 4-Aminobutyric acid (12.4 g, 120 mmol) was dissolved in a solution of $Na_2CO_3$ (50.9 g, 480 mmol) in water (450 mL). To this mixture a solution of 9-fluorenylmethyl chloroformate (Fmoc-chloride, 25.8 g, 100 mmol) in 1,4-dioxane (60 mL) was added under vigorous stirring at ambient temperature. The initially formed precipitate disappeared during the reaction (approx. 3 hours). After the Fmoc-chloride was completely consumed (TLC: $CH_2Cl_2$/EtOH, 90:10; $R_f$ (product) 0.67), the mixture was carefully adjusted to pH 2 by adding concentrated HCl. The slurry obtained was over- 63 mmol) and 4-dimethylaminopyridine (0.7 g, 6 mmol) were -dissolved in 1,4-dioxane (550 mL) and cooled to 10° C. To this solution dicyclohexylcarbodiimide (DCC, 11.9 g, 58 mmol) taken up in 1,4-dioxane (50 mL) was added in one portion. After stirring over night at room temperature the reaction mixture was quenched (TLC: EtOAc/hexane, 50:50; $R_f$(product) 0.63) by adding acetic acid (2 mL). After 1 hour the solution was filtered to remove precipitated urea. The obtained filter cake was washed with ethyl acetate (2×250 mL) and the combined organic phases were evaporated to dryness and taken up in ethyl acetate (500 mL). The organic phase was washed with aqueous NaHCO$_3$ (5%, 3×200 mL), saturated NaCl (3×200 mL), dried over Na$_2$SO$_4$ and evaporated to dryness. A stirred solution of the obtained residue in ethyl acetate (200 mL) was subjected to a slow addition of hexanes (800 mL). The resulting suspension was allowed to crystallize overnight, filtered, washed with hexanes (2×50 mL) and dried in vacuo.

To remove polar contaminants the residue was dissolved in boiling ethanol (200 mL) and allowed to crystallize overnight at room temperature. The crystals were filtered, washed with cold ethanol (2×20 mL) and dried in vacuo. The crude product (2.2 g, 48%) was subjected to prep. HPLC (CH$_2$Cl$_2$/ethyl acetate, 100:0 to 97:3), yielding 10.3 g (41.0%) of product that was 99.5% pure by HPLC. $^1$H NMR (200 MHz, CDCl$_3$): δ 8.29–7.24 (m, 12H), 4.94 (bs, 1H), 4.45 (d, 2H), 4.24 (t, 1H), 3.50–3.28 (m, 2H), 2.67 (t, 2H), 2.11–1.90 (m, 2H).

N4-(4-methoxytrityl)aminobutyric acid. 4-Aminobutyric acid (10.3 g, 100 mmol) was suspended in a DMSO/pyridine mixture (100 mL, 80:20 v/v). 4-Methoxytrityl chloride (34.0 g, 110 mmol) was added in portions (8.0 g, 8.0 g, 7.0 g, 7.0 g and 4.0 g) to the stirred suspension in 15 minute intervals at ambient temperature and the reaction mixture was stirred overnight at room temperature. After all of the 4-aminobutyric acid was consumed (TLC: CH$_2$Cl$_2$/EtOH, 90:10; R$_f$ (product) 0.52), the mixture was diluted with CH$_2$Cl$_2$ (500 mL). The organic phase was washed with saturated NaCl (1×500 mL, 1×300 mL), dried over Na$_2$SO$_4$ and evaporated to dryness. The crude material (40.3 g) was purified by prep. HPLC (CH$_2$Cl$_2$/ethanol+0.2% triethylamine, 100:0 to 97:3) to yield 25.2 g (67%) of 97.3% pure product (HPLC). $^1$H NMR (200 MHz, CDCl$_3$): δ 7.51–6.75 (m, 14H), 3.77 (s, 3H), 2.38 (t, 2H), 2.24 (t, 1H), 1.73–1.94 (m, 2H).

N4-(4-methoxytrityl)-aminobutyryl-p-nitrophenyl ester. To a solution of N4-(4-methoxytrityl)aminobutyric acid (25.2 g, 67 mmol) in ethyl acetate (250 mL) was added a mixture of 4-nitrophenol (10.4 g, 75 mmol) and DCC (13.9 g, 67 mmol) in ethyl acetate (200 mL). After the addition of 4-dimethylamino-pyridine (820 mg, 7 mmol), the reaction mixture was stirred overnight at room temperature. Upon consumption of all of the N4-(4-methoxytrityl)aminobutyric acid (TLC: EtOAc/hexane, 33:66; R$_f$ (product) 0.65), the reaction was quenched by adding water (1 mL). After 1 hour the mixture was filtered to remove the precipitated urea. The obtained filter cake was washed with ethyl acetate (300 mL) and the combined organic phases were extracted with aqueous K$_2$CO$_3$ (5%, 2×200 mL), aq. NaHCO$_3$ (5%, 2×200 mL), water (200 mL), dried over Na$_2$SO$_4$ and evaporated to dryness. The crude material was purified by prep. HPLC (CH$_2$CL$_2$) to yield 20.7 g (62%) of 92.6% pure (HPLC) product.

1-Amino-N3-(N4-(4-methoxytrityl)-aminobutyryl)-aminopropan-2-ol. A solution of N4-(4-methoxytrityl)-aminobutyryl-p-nitrophenyl ester (20.4 g, 41 mmol) in CH$_2$Cl$_2$ (150 mL) was added to a solution of 1,3-diaminopropan-2-ol (7.4 g, 82 mmol) and triethylamine (5.7 mL, 41 mmol) in CH$_2$Cl$_2$ (200 mL) over a period of 2 hours at ambient temperature. The reaction mixture was stirred overnight at room temperature. Upon complete consumption of the nitrophenyl ester (TLC: CH$_2$Cl$_2$/EtOH, 80:20; R$_f$ (product) 0.06), the suspension was washed with aqueous K$_2$CO$_3$ (5%, 2×250 mL), aq. NaHCO$_3$ (5%, 2×250 mL), water (250 mL) over Na$_2$SO$_4$ and evaporated to dryness. The crude material (15.6 g) was purified by prep. HPLC (1. CH$_2$Cl$_2$/ethanol, 100:0 to 80:20; 2. methanol), which yielded 9.0 g (49%) of 97.3% pure (HPLC) product. $^1$H NMR (200 MHz, CDCl$_3$): δ 7.60–6.75 (m, 14H), 6.15 (t, 1H), 3.75 (s, 3H), 3.64–3.38 (m, 2H), 3.29–3.05 (m, 1H), 2.80 (dd, 1H), 2.56 (dd, 1H), 2.37–2.11 (m, 4H), 1.97–1.72 (m, 3H). $^{13}$C NMR (50 MHz, CDCl$_3$): δ 173.8, 157.8, 146.3, 138.2, 129.7, 128.4, 127.7, 126.1, 113.0, 70.9, 70.3, 55.2, 44.6, 43.1, 34.6, 26.7.

1-(N4-(9-fluorenylmethoxyarbonyl)aminobutyryl)-amino-3-(N4-(4-methoxytrityl)-aminobutyryl)-aminopropan-2-ol. A solution of 1-amino-N3-(N4-(4-methoxytrityl)-aminobutyryl)-aminopropan-2-ol (9.0 g, 20.1 mmol) and ethyldiisopropylamine (3.5 mL, 20.1 mmol) in CH$_2$Cl$_2$ (100 mL) was added to a solution of N4-(9-fluorenylmethoxycarbonyl)-aminobutyryl-p-nitrophenyl ester (9.0 g, 20.1 mmol) in CH$_2$Cl$_2$ (100 mL) over a period of 20 minutes at ambient temperature. The reaction mixture was stirred overnight at room temperature (TLC: CH$_2$Cl$_2$/EtOH, 90:10; R$_f$ (product) 0.54). The solution was extracted with aqueous K$_2$CO$_3$ (5%, 2×200 mL), aq. NaHCO$_3$ (5%, 2×200 mL), water (200 mL), dried over Na$_2$SO$_4$ and evaporated to dryness. Upon adding ethyl acetate (100 mL) to the residue, the mixture was heated to reflux until a clear solution was obtained. Hexane (50 mL) was added over a period of 1 minute to the stirred mixture. The suspension was allowed to crystallize for 4 hours at room temperature, filtered, washed with hexane/ethyl acetate (100 mL, 33:66) and dried in vacuo. The crystals obtained were purified via prep. HPLC to yield 9.3 g (61%) of the desired product, which was 99.0% pure by HPLC. $^{13}$C NMR (50 MHz, CDCl$_3$): δ 174.6, 174.1, 157.7, 156.9, 146.2, 143.8, 141.3, 138.1, 129.7, 128.4, 127.7, 127.0, 126.1, 125.0, 120.0, 113.0, 70.2, 70.1, 66.5, 55.2, 47.2, 43.0, 40.0, 34.5, 33.2, 26.6, 26.0.

1-(N4-(9-fluorenylmethoxycarbonyl)aminobutyryl)-amino-3-(N4-(4-methoxytrityl)-aminobutyryl)-aminopropan-2-ol cyanoethoxydiisopropylamino-phosphoramidite. 1-(N4-(9-fluorenylmethoxycarbonyl)aminobutyryl)-amino-3-(N4-(4-methoxytrityl)-aminobutyryl)-aminopropan-2-ol (8.0 g, 10.6 mmol) was co-evaporated twice with dry THF (100 mL, each) and dried in vacuo. The residue was dissolved in THF (100 mL), cooled to 5° C. on an ice bath and diisopropylethylamine (2.8 mL, 15.9 mmol) was added. Chloro-2-cyanoethoxy-diisopropylaminophosphane (2.89 g, 12.2 mmol) was added to the solution in one portion. The ice bath was removed and the reaction mixture was stirred for 1.25 hours at ambient temperature (TLC: THF/EtOAc, 25:75; R$_f$ (product) 0.58). The solution was diluted with ethyl acetate (400 mL), washed with aqueous NaHCO$_3$ (5%, 3×250 mL), dried over Na$_2$SO$_4$ and evaporated to dryness. The crude material was purified by prep. HPLC (ethyl acetate/hexane 70:30 to 80:20) yielding 3.9 g (38%) of a white foam, which was subjected to additional precipitation steps due to an insufficient purity as measured by $^{31}$P-NMR (~75%). The stirred solution of the residue in ethyl acetate (15 mL) was triturated with hexanes (100 mL) and the resulting suspension was allowed to separate for 30 minutes and the upper phase was decanted. This process was repeated and the resulting oil was dried in vacuo to give 3.4 g (32%) of a white foam, the purity of which was 97.5% by HPLC, and 96.8% by $^{31}$P-NMR. $^1$H NMR (200 MHz, CDCl$_3$): δ 7.98–6.78 (m, 22H), 6.77–6.45 (m, 1H), 5.42–5.21 (m, 4.55–4.33 (m, 2H), 4.07–3.49 (m, 9H), 3.40–3.05 (m, 3H), 3.02–2.80 (m, 1H), 2.75–2.53 (m, 2H), 2.42–2.12 (m, 6H), 2.06–1.63 (m, 5H), 1.55–1.08 (m, 12H). $^{31}$P NMR (81 MHz, CDCl3): δ 148.64, 148.71.

Example 2

Synthesis of the Bifunctional Linker (14): 1-(N6-(9-fluorenylmethoxycarbonyl)aminocaproyl)-amino-3-(N6-(cyclohexa-2,4-dienylmethoxycarbonyl)aminocaproyl)-aminopropan-2-ol cyanoethoxydiisopropylaminophosphoramidite The synthesis of bifunctional linker 14 is outlined in Scheme 2.

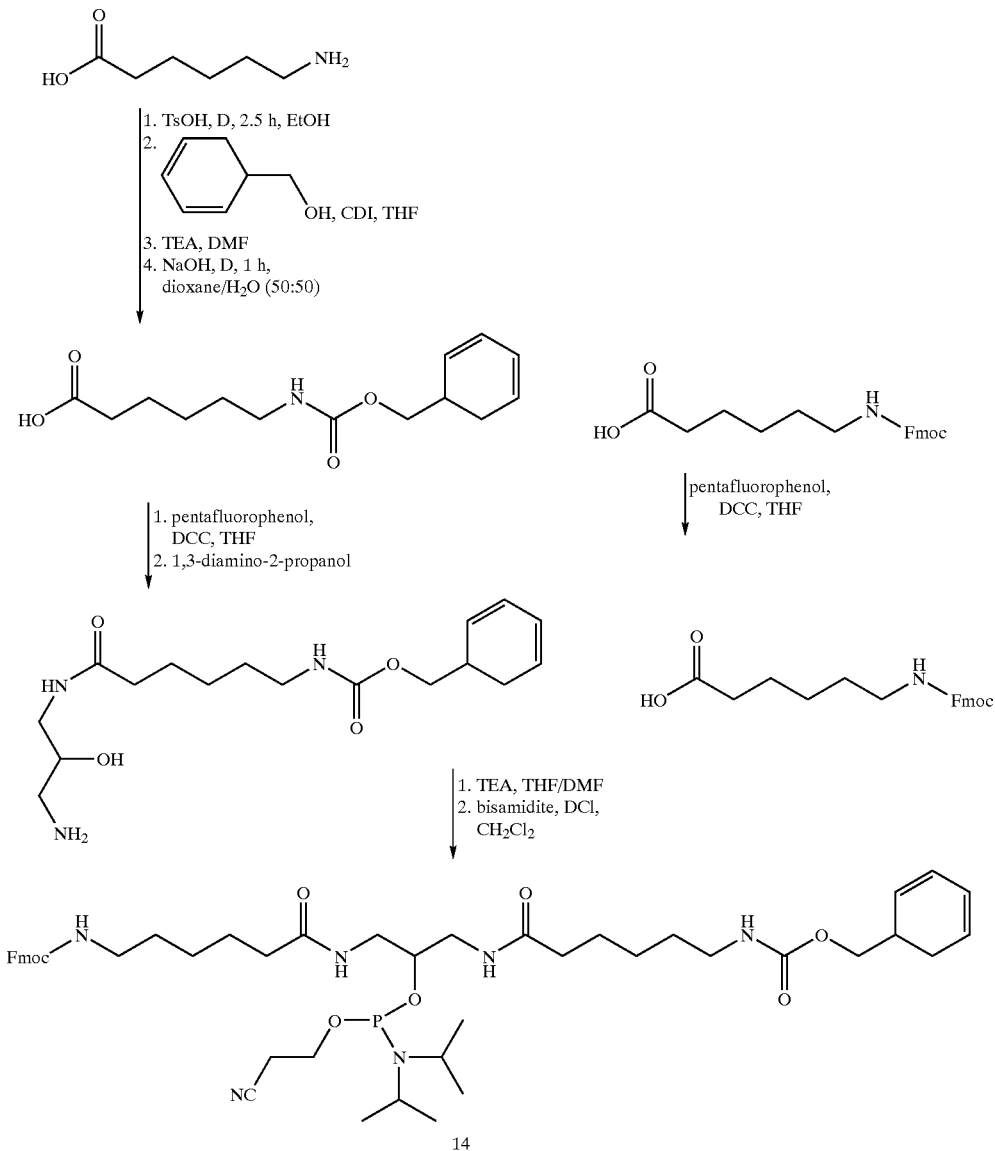

Ethyl-ε-aminocaproate hydrotosylate. A mixture of ε-aminocaproic acid (70.0 g, 533.8 mmol), toluenesulfonic acid (111.7 g, 1.1 eq.) and ethanol (1.6 L) was heated to reflux for 20 hours. Thereafter, TLC ($CH_2Cl_2$/EtOH/TEA, 85:10:5) revealed complete conversion. The reaction mixture was concentrated until solids started to precipitate. The precipitation was driven to completion by adding diethyl ether (1.5 L). The white solid was filtered, washed with diethyl ether, and dried in vacuo affording 174.0 g (98.3%) of a white powder. $^1$H NMR: (200 MHz, $CDCl_3$): δ 7.47 (d, 2H, J=8.2 Hz), 7.10 (d, 2H, J=8.2 Hz), 4.02 (q, J=7.0 Hz), 2.79–2.65 (m, 2H), 2.28 (s, 3H), 2.25 (t, 2H, J=7.0 Hz), 1.16 (t, 3H, J=7.0 Hz), 1.49 (dt, 4H, J=7.6, 7.0 Hz), 1.29–1.22 (m, 2H). $^{13}$C NMR: 173.4, 145.6, 138.8, 128.9, 126.1, 60.4, 39.4, 33.9, 27.3, 25.9, 24.6, 21.5, 14.8.

Ethyl-N6-(cyclohexa-2,4-dienylmethoxycarbonyl)-aminocaproate. Hydroxymethylcyclohexa-2,4-diene (49.0 g, 444.8 mmol), dissolved in THF (100 mL), was added under inert conditions to a stirred solution of carbonyldiimidazole (CDI, 72.1 g, 444.8 mmol) in THF (500 mL) at a rate of 20 mL/min. The mixture was allowed to stir for 2 hours. An aliquot was removed, dried and dissolved in $CDCl_3$ to confirm the completion of the reaction by $^1$H NMR analysis. The solvent was removed by evaporation and the residue was combined with ethyl-ε-aminocaproate hydrotosylate (162.2 g, 489.3 mmol) in DMF (400 mL). After flushing with argon, triethylamine (75.0 mL, 1.2 eq.) was added and the mixture was allowed to stir overnight at ambient temperature. The reaction was quenched with water (500 mL) and the aqueous phase was extracted with ethyl acetate (3×250 mL). The organic fractions were combined and washed with saturated bicarbonate and brine. The organic phase was dried with $MgSO_4$, filtered and the solvent removed in vacuo. The resulting oil was purified via flash chromatography (EtOAc/hexanes 2:8) to yield 53.3 g (35.6%) of a colorless wax.

$^1$H NMR (200 MHz, $CDCl_3$): δ 5.92–5.82 (m, 2H), 5.75–5.70 (m, 1H), 5.64–5.59 (m, 1H), 4.09 (q, 2H, J=7.3 Hz), 4.02–3.90 (m, 2H), 3.19–3.11 (m, 2H), 2.27 (t, 2H, J=7.6 Hz), 2.20–2.00 (m, 2H), 1.66–1.55 (m, 2H), 1.55–1.43 (m, 2H), 1.40–1.29 (m, 2H),1.22 (t, 3H, J=7.0 Hz). $^{13}$C NMR ($CDCl_3$): δ 173.7, 156.8, 126.7, 125.6, 124.1, 66.4, 60.4, 41.0, 34.4, 33.2, 29.9, 26.4, 25.4, 24.8, 14.4.

N6-(Cyclohexa-2,4-dienylmethoxycarbonyl)-aminocaproic acid. A mixture of ethyl-N6-(cyclohexa-2,4-dienylmethoxycarbonyl)-aminocaproate (60.0 g, 203.1 mmol), 1 N NaOH (600 mL, 3 eq.) and dioxane (600 mL) was heated to reflux and allowed to stir for 60 minutes. The mixture was then concentrated to half the original volume and 4 N HCl (200 mL) was added with vigorous stirring. The solids were filtered off, washed with water and co-evaporated with acetonitrile (3×500 mL) to afford 51.2 g (191.4 mmol, 94.2%) of a white powder. $^1$H NMR (200 MHz, $CDCl_3$): δ 10.50 (bs, 1H), 5.94–5.83 (m, 2H), 5.76–5.70 (m, 2H), 5.65–5.60 (m, 1H), 4.82 (s, 1H), 4.05–3.97 (m, 2H), 3.15 (q, 2H, J=6.5 Hz), 2.33 (t, 2H, J=7.3 Hz), 2.25–1.99 (m, 2H), 1.68–1.58 (m, 2H), 1.55–1.45 (m, 2H), 1.41–1.32 (m, 2H). $^{13}$C NMR (CDCl3): δ 178.9, 158.5, 127.2, 126.5, 125.5, 124.1, 67.2, 41.0, 34.1, 33.0, 26.3, 25.3, 24.5.

Pentafluorophenyl-N6-(cyclohexa-2,4-dienylmethoxycarbonyl)-aminocaproate. Dicyclohexylcarbodiimide (DCC, 44.6 g, 1.15 eq.) was added to a stirred solution of N6-(cyclohexa-2,4-dienylmethoxycarbonyl)-aminocaproic acid (50.1 g, 187.3 mmol) in $CH_2Cl_2$ (400 mL). Pentafluorophenol (45.4 g, 1.32 eq.), dissolved in $CH_2Cl_2$ (100 mL) was added under inert conditions. After stirring overnight TLC (EtOAc/Hex/AcOH, 35:60:5) showed complete conversion. The reaction mixture was filtered and the filtrate was used crude in the next reaction. NMR of a purified sample: $^1$H NMR (200 MHz, $CDCl_3$): δ 5.96–5.82 (m, 2H), 5.80–5.70 (m, 1H), 5.65–5.60 (m, 1H), 4.71 (s, 1H), 4.01 (d, 2H), 3.20 (q, 2H, J=6.5 Hz), 2.65 (t, 2H, J=7.0 Hz), 2.37–2.01 (m, 2H), 1.75 (q, 2H, J=7.3 Hz), 1.64–1.61 (m, 4H).

1-Amino-N3-(N6-(cyclohexa-2,4-dienylmethoxycarbonyl)-aminocaproyl)-aminopropan-2-ol. A mixture of 1,3-diamino-2-hydroxypropane (67.6 g, 750 mmol) and $CH_2Cl_2$ (1 L) was stirred until the diamine was dissolved completely (2 hours). A solution of crude pentafluorophenyl-N6-(cyclohexa-2,4-dienylmethoxycarbonyl)-aminocaproate (187.3 mmol) was added at a rate of approximately 10 mL/min. The reaction mixture was stirred overnight at ambient temperature, filtered and the filtrate was concentrated to give an oil. The oil was purified via flash chromatography (10 L of EtOH/$CH_2Cl_2$, 1:4, followed by 10 L of EtOH/AcOH, 19:1) to afford 44.6 g (60% over 2 steps) of a tan powder (isolated as the acetate salt). $^1$H NMR (200 MHz, $CDCl_3$): δ 7.87 (s, 1H), 7.14 (s, 1H), 5.96–5.84 (m, 2H), 5.80–5.70 (m, 1H), 5.63 (dd, 1H, J=9.4, 3.5 Hz), 4.19 (bs, 3H), 3.85 (d, 2H, J=5.9 Hz), 3.46 (s, 1H), 3.03 (dt, 2H, J=4.1, 5.9 Hz), 2.92 (q, 2H, J=6.5 Hz), 2.60–2.37 (m, 6H), 2.04 (t, 2H, J=7.3 Hz), 1.48–1.30 (m, 4H), 1.77 (s, 3H), 1.19 (q, 2H, J=6.5 Hz). $^{13}$C NMR ($d_6$-DMSO): δ 174.9, 173.3, 156.8, 127.5, 126.1, 125.7, 124.4, 67.8, 65.6, 43.6, 43.2, 35.9, 33.2, 29.9, 26.6, 25.7, 25.3, 23.9.

Pentafluorophenyl-N6-(9-fluorenylmethoxycarbonyl)-aminocaproate. Pentafluorophenol (32.6 g, 1.25 eq.), dissolved in THF (150 mL), was added to a stirred solution of N6-Fmoc-aminocaproic acid (50.0 g, 141.5 mmol) and DCC (36.5 g, 1.25 eq.) in THF (400 mL) under inert conditions. The reaction was allowed to stir overnight at ambient temperature. The solids were filtered off and washed with THF. The filtrate was concentrated to approximately 300 mL and used crude in the next reaction.

1-(N6-(9-Fluorenylmethoxycarbonyl)aminocaproyl)-amino-3-(N6-(cyclohexa-2,4-dienylmethoxycarbonyl)aminocaproyl)-aminopropan-2-ol. 1-Amino-N3-(N6-(cyclohexa-2,4-dienylmethoxycarbonyl)-aminocaproyl)-aminopropan-2-ol (43.6 g, 109.2 mmol) was mixed with THF (200 mL) and DMF (100 mL) and the flask was flushed with argon. Triethylamine (30.4 mL, 2.0 eq.) and crude pentafluorophenyl-N6-(9-fluorenylmethoxycarbonyl)-aminocaproate (141.5 mmol) were added to the stirred mixture. After 3 hours TLC (10% EtOH in $CH_2Cl_2$) established the formation of the desired product ($R_f$ 0.4) and the absence of starting material (TLC with 5% AcOH/EtOH). The reaction was quenched by pouring the mixture into 0.2 M $NaH_2PO_4$ (1 L) followed by storage at 4° C. overnight. The mixture was extracted with EtOAc (3×500 mL) and the combined organic phases were washed with saturated $NaHCO_3$ (2×500 mL) and brine (500 mL). The organic phase was dried with $MgSO_4$, filtered and concentrated. Flash chromatography (EtOH/$CH_2Cl_2$, 20:80) of the crude material gave 34.10 g (46.3%) of a white solid. $^1$H NMR (200 MHz, $CDCl_3$): δ 7.72 (d, 2H, J=7.6 Hz), 7.56 (d, 2H, J=7.6 Hz), 7.37 (t, 2H, J=7.6 Hz), 7.27 (t, 2H, J=7.6Hz), 7.10–6.89 (m, 2H), 5.97–5.81 (m, 2H), 5.77–5.67 (m, 1H), 5.61 (dd, 1H), 5.27–5.21 (m, 1H), 5.07–5.00 (m, 1H), 4.35 (d, 2H, J=7.0 Hz), 4.19 (t, 1H), 3.96 (d, 2H, J=6.5 Hz), 3.69–3.75 (m, 2H), 3.40–3.28 (m, 2H), 3.25–3.05 (m, 6H), 2.65–2.50 (m, 1H), 2.23–2.03 (m, 6H), 1.60 (q, 2H, J=7.3 Hz), 1.47 (q, 2H, J=7.3 Hz), 1.35–1.25 (m, 2H). $^{13}$C NMR ($CDCl_3$): δ 175.0, 156.8, 144.2, 141.5, 127.9, 127.2, 126.6, 125.7, 125.6, 125.3, 124.2, 120.2, 70.0, 66.7, 66.4, 58.5, 47.5, 42.6, 41.0, 36.4, 33.1, 29.8, 26.4, 25.4, 18.6.

1-(N6-(9-Fluorenylmethoxycarbonyl)aminocaproyl)-amino-3-(N6-(cyclohexa-2,4-dienylmethoxycarbonyl) aminocaproyl)-aminopropan-2-ol cyanoethoxydiisopropylaminophosphoramidite. A solution of dicyanoimidazole (DCI, 75 mg, 0.06 eq.) in $CH_3CN$ (10 mL) was added to a mixture of 1-(N6-(9-fluorenylmethoxycarbonyl)aminocaproyl)-amino-3-(N6-(cyclohexa-2,4-dienylmethoxycarbonyl)aminocaproyl)-aminopropan-2-ol (7.35 g, 10.89 mmol) and bis(diisopropylamino)-2-cyanoethoxyphosphan ("bis-amidite", 3.44 g, 1.05 eq.) in $CH_2Cl_2$ (200 mL) under inert conditions. The reaction mixture was stirred overnight at ambient temperature, diluted to 500 mL with $CH_2Cl_2$ and washed with saturated bicarbonate and brine. The aqueous fractions were combined and back-extracted with $CH_2Cl_2$. The organic phases were combined, dried with $MgSO_4$, filtered and concentrated to give an oil. The crude product was purified via flash chromatography (THF/hexane, 60:40) to give 5.65 g (60%) of a highly viscous clear oil. $^1$H NMR ($d_6$-DMSO): δ 7.86 (d, 2H, J=7.6 Hz), 7.74 (t, 1H, J=5.9 Hz), 7.66 (d, 3H, J=7.0 Hz), 7.35 (m, 5H), 7.11 (t, 1H, J=5.3 Hz), 5.90 (m, 2H), 5.76 (m, 1H), 5.64 (dd, 1H, J=3.5 Hz, 9.4 Hz), 4.27 (d, 2H, J=6.4 Hz), 4.20 (d, 1H, J=6.4 Hz), 3.86 (d, 2H, J=5.8 Hz), 3.80 (m, 3H), 3.78 (m, 3H), 3.33 (d, 1H, J=7.0 Hz), 3.19 (bs, 3H), 2.92 (t, 4H, J=6.4 Hz), 2.75 (t, 2H, J=5.9 Hz), 2.24–2.15 (m, 1H), 2.07–2.03 (m, 5H), 1.78–1.70 (m, 1H), 1.48–1.35 (m, 7H), 1.22–1.06 (m, 15H). $^{31}$P NMR (d$_6$-DMSO): δ 148.5 (s). MS (FAB+) calcd. for $C_{47}H_{67}N_6O_8P$ (MH+) 876.05, found 875.

Example 3

Synthesis of a dT10 Oligonucleotide Sequence Conjugated to Bifunctional Linker (13)

A dT10 oligonucleotide sequence was assembled on an Applied Biosystems model 391 synthesizer on a 1 μmol scale on a CPG 500 dT-support. The synthesis protocol supplied by the instrument manufacturer was followed with the exception that a 0.25 M solution of 4,5-dicyanoimidazole (DCI) was used as the activator solution. The amidite (13) was used in an additional synthesis cycle on the support as a 0.1 M solution without further modifications of the cycle. The resulting oligonucleotide was obtained in the trityl-on mode and subjected to treatment with concentrated aqueous ammonia for 24 hours at room temperature, which cleaved the oligonucleotide from the support and removed the N-Fmoc protective group of the linker in one step. The crude product was 91.9% pure as analyzed by anion-exchange chromatography and found to contain 1.2% dT10 indicating a coupling efficiency greater than 98%. The product was positively identified in the crude mixture by a co-injection technique using a dT10-standard in the HPLC analysis. The oligonucleotide was treated with 80% aqueous acetic acid for 1 hour at 55° C. to remove the N-MMT protective group of the linker resulting in a crude product which was 93.0% pure by anion exchange HPLC and contained 1.1% dT10.

Example 4

Synthesis of a dT10 Oligonucleotide Sequence Conjugated to Bifunctional Linker (14)

A dT10 oligonucleotide sequence was assembled on an Applied Biosystems model 391 synthesizer on a 1 μmol scale on a CPG 500 dT-support. The synthesis protocol supplied by the instrument manufacturer was followed with the exception that a 0.25 M solution of 4,5-dicyanoimidazole (DCI) was used as the activator solution. The amidite (14) was used in an additional synthesis cycle on the support as a 0.1 M solution without further modifications of the cycle. The resulting oligonucleotide was subjected to treatment with concentrated aqueous ammonia at room temperature, which cleaved the oligonucleotide from the support and removed the N-Fmoc protecting group of the linker in one step. The crude material from this synthesis contained 47.9% product, 16.5% dT10 and 17.7% of product that was still protected with the N-Fmoc group after 3 hours of deprotection time, as analyzed by anion-exchange chromatography. The product was positively identified in the crude mixture by a co-injection technique using a dT10-standard in the HPLC analysis.

Example 5

Synthesis of the Oligonucleotide Sequence d(CCACTATCCTTCGCAAGACCCTTCC) (SEQ ID NO: 12) Conjugated to the Bifunctional Linker (13)

The oligonucleotide sequence d(CCACTATCCTTCGCAAGACCCTTCC) (SEQ ID NO:12) was assembled on an Applied Biosystems model 391 synthesizer on a 1 μmol scale. The synthesis protocol supplied by the instrument manufacturer was followed. The amidite (13) was used in an additional synthesis cycle on the support as a 0.1 M solution without further modifications of the cycle. The resulting oligonucleotide was obtained in the trityl-off mode and manually subjected to further treatment with detritylating solution and acetonitrile in order to ensure the complete removal of the N-MMT protecting group. The material was subjected to treatment with concentrated aqueous ammonia solution for 24 hours at room temperature. The resulting solution was evaporated, re-dissolved in 100 μL of water and precipitated with 200 μL of cold (−200° C.) ethanol and 20 μL of 4 M ammonium chloride solution. The mixture was chilled at −20° C. for 15 minutes and the pellet was recovered by centrifugation at 15,000 rpm for 15 minutes. The supernatant was removed and the pellet was washed with 70% aqueous ethanol. The presence of the target molecule in the pellet was confirmed by mass spectroscopy (m/z calculated 7779.7; found 7780.3).

Example 6

Procedure for the Synthesis of an Oligonucleotide Sequence Conjugated to the Bifunctional Linker (14) Potentially via a HEG Spacer The desired oligonucleotide sequence was assembled on an EXPEDITE™ 8909 (Applied Biosystems Inc.) synthesizer at 1 μmol scale on a CPG 500-support. Standard protected deoxynucleoside phosphoramidites were employed (amidites derived from DMT-dT, DMT-dA(bz), DMT-dG(ib) and DMT-dC(bz)). The synthesis protocol supplied by the instrument manufacturer was followed with the exception that a 0.25 M solution of 4,5-dicyanoimidazole (DCI) was used as the activator solution. In the case in which the conjugation of the bifunctional linker via the HEG spacer was intended, a 0.063 M solution of the DMT-protected HEG phosphoramidite (Cruachem Ltd., Glaskow, UK) was applied in an additional unmodified synthesis cycle on the support. The amidite (14) was then coupled to the HEG modified oligonucleotide sequence on the support in the last synthesis cycle by applying a 0.1 M solution of(14) and a 0.25 M solution of 4,5-dicyanoimidazole (DCI). The coupling routine of the synthesis cycle was repeated three times in this coupling step. Despite the mollification of the coupling routine, a standard synthesis cycle was employed as recommended by the manufacturer of the instrument. The CPG support with the resulting linker conjugated oligonucleotide was treated with concentrated aqueous ammonia at room temperature for 60 minutes to cleave the oligonucleotide from the support. The CPG was filtered off and the filtrate was incubated at 55° C. over night to deprotect the nucleobases and to remove the N-Fmoc protecting group of the linker in one step. The solution of the oligonucleotide was concentrated to dryness in a vacuum centrifuge. The residue was dissolved in a mixture of 200 μL water and 44 μL of a 3 M solution of sodium acetate, pH 5.5. 2 mL of isopropanol was added and the mixture was chilled at −20° C. for 1 hour. The resulting suspension was centrifuged for 10 minutes and the supernatant of the pellet was discarded. The pellet was washed once with 70% ethanol and dried under vacuum.

Example 7

Synthesis of the Ethidium Derivative (15): 8-(6-maleimidocaproyl)-ethidium bromide The synthesis of the maleimide-ethidium conjugate (15) is outlined in Scheme 3.

Scheme 3

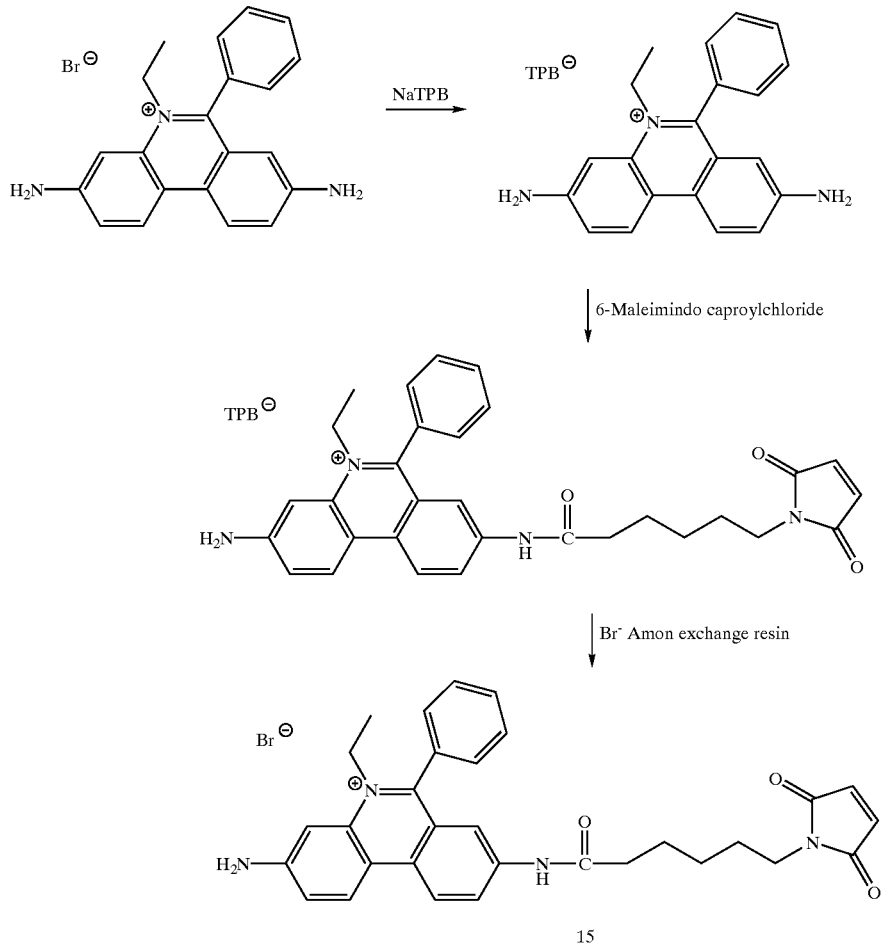

Ethidium tetraphenylborate. Ethidium bromide (1.05 g, 2.66 mmol) was dissolved in 400 mL of water. A solution of sodium tetraphenylborate (2.74 g, 8 mmol) in 200 mL water was added with stirring at room temperature, producing a bright red solid. The solid was filtered off, washed with water and dissolved in $CH_2Cl_2$. The resulting solution was filtered and evaporated to dryness. The residue was coevaporated with acetonitrile to yield 1.49 g (88%) of a purple solid.

8-(6-maleimidocaproyl)-ethidium tetraphenylborate. 6-Maleimidocaproic acid (211 mg, 1.0 mmol) was dissolved in 10 mL $CH_2Cl_2$. Oxalyl chloride (0.50 mL, 5 equiv.) was added under inert gas followed by one drop of DMF. The reaction mixture was stirred for one hour at room temperature. The solvent was evaporated under vacuum and the residue was co-evaporated once with 10 mL $CH_2Cl_2$ under vacuum. The resulting 6-maleimidocaproic acid chloride was dissolved in 2 mL $CH_2Cl_2$.

Ethidium tetraphenylborate (660 mL, 1.0 mmol) was dissolved in 10 mL $CH_2Cl_2$. Triethylamine (2 equiv.) and the previously prepared solution of 6-maleimidocaproic acid chloride were added under inert gas. The reaction mixture was protected from light and stirred overnight at room temperature. The reaction mixture was diluted with 50 mL $CH_2Cl_2$ and extracted with aqueous $NaH_2PO_4$ (pH 5.5, 0.2 M, 3×50 mL). The organic phase was dried with $MgSO_4$, filtered, and evaporated to dryness to give a red-orange solid.

8-(6-maleimidocaproyl)-ethidium bromide. 8-(6-maleimidocaproyl)-ethidium tetraphenylborate from the previous step was dissolved in dioxane/N,N-dimethylformamide (DMF) 5:1, v/v (10 mL) and then added to 10 mL water. N,N-dimethylformamide was added in 1 mL portions until a homogeneous solution was obtained. Polymer-supported bromide (bromide on Amberlyst A-26, 3 mmol bromide/g, 5 g) was added and the resulting suspension was shaken at room temperature overnight. The solids were filtered off and the filtrate was evaporated to dryness under vacuum. The residue was coevaporated with acetonitrile to give an orange-red solid. The crude material was purified by prep. HPLC with 10% ethanol in $CH_2Cl_2$. A bis-derivatized ethidium compound eluted first followed by the desired product, an orange solid, yield 149 mg (26% over 2 steps). $^1H$ NMR (300 MHz, $d_6$-DMSO): δ 10.27 (s, 1H), 8.79 (t, 2H), 8.25 (d, 1H), 7.68–7.79 (m, 5H), 7.38–7.43 (m, 2H), 6.98 (s, 2H), 6.61 (s, 1H), 4.48 (d, 2H), 3.30–3.48 (m, H), 2.25 (t, 2H), 1.38–1.58 (m, 6H), 1.20 (q, 2H). MS (FAB+) m/z=507.

Example 8

Preparation of NHS-Ester Functionalized Thiazole Orange Derivative (16): 6-(4-[3-methyl-2,3-dihydro (benzo-1,3-thiazole)-2-methyliden]-1-quinolinium)-hexanoic acid N-hydroxysuccinimide ester The synthesis of the thiazole orange derivative (16) is outlined in Scheme 4.

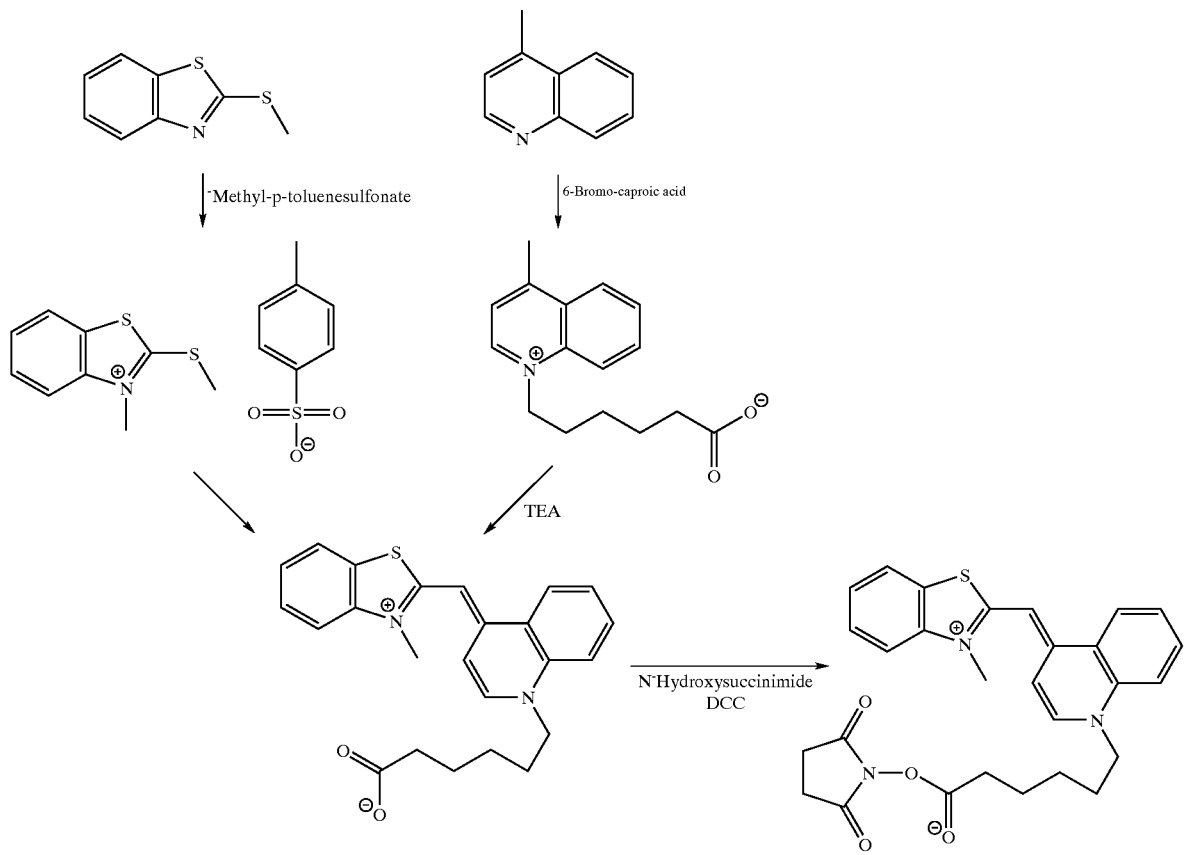

Scheme 4

3-Methyl-2-(methylthio)benzothiazolium tosylate. A mixture of 2-methylthio-benzothiazole (18.4 g, 0.1 mol) and methyl-p-toluenesulfonate (76 mL, 0.5 mol) was heated to a temperature between 120° C. to 145° C. for 1 hour. After cooling to room temperature diethyl ether (200 mL) was added. The resulting solid was triturated with diethyl ether and isolated by filtration to give the crude product (42.7 g, quantitative). $^1$H-NMR (300 MHz, CDCl$_3$): δ 8.12 (d, 1H), 7.92 (d, 1H), 7.62 (d, 3H), 7.3 (t, 1H), 7.02 (d, 2H), 4.05 (s, 3H); 3.0 (s, 3H), 2.23 (3, 3H).

6-(4-Methyl-1-quinolinium)-hexanoic acid. Lepidine (14.3 mL, 15.5 g, 0.108 mol) was mixed with 6-bromohexanoic acid (31 g, 0.159 mmol, 1.5 eqiv.) and heated at 130° C. for 6 hours. The mixture was allowed to cool to room temperature and acetone (100 mL) was added. The resulting solid was triturated with acetone to provide the crude product (30.9 g, quantitative). $^1$H-NMR (300 MHz, d$_6$-DMSO): δ 9.44 (d, 1H), 8.60 (d, 1H), 8.55 (dd, 1H), 8.28 (d, 1H), 8.0 (m, 2H), 5.0 (t, 2H), 3.0 (s, 3H), 2.2 (t, 2H), 1.95 (m, 2H), 1.55 (m, 2H), 1.4 (m, 2H).).

6-(4-[3-Methyl-2,3-dihydro-(benzo-1,3-thiazole)-2-methylidene]-1-quinolinium)-hexanoic acid. 6- (4-Methyl-1-quinolinium)-hexanoic acid (10.5 g, 40.8 mmol) and 3-methyl-2-(methylthio)benzothiazolium tosylate (15 g, 40.8 mmol) were mixed together in dichloromethane (100 mL). Triethylamine (15 mL, 102 mmol, 2.5 eqiv.) was added and the slightly turbid solution was stirred at room temperature over night. The reaction was quenched by the addition of potassium iodide (23 mL of an aqueous solution (30%, v/v)). The product was precipitated with hydrochloric acid (80 mL of an aqueous solution (3%, v/v)). After stirring for 2 hours the red solid was isolated by filtration and washed with tetrahydrofuran to yield a crude product (11.8 g, 71.6%), which was not further purified. $^1$H-NMR (300 MHz, CD$_3$OD): δ 8.68 (d, 1H), 8.43 (d, 1H), 8.08 (dd, 1H), 7.98 (m, 1H), 7.9 (dd, 1H), 7.76 (m, 1H), 7.68 (d, 1H), 7.62 (m, 1H), 7.5 (d, 1H), 7.42 (m, 1H), 6.94 (s, 1H), 4.6 (t, 2H), 4.0 (s, 3H), 2.32 (t, 2H), 2.0 (m, 2H), 1.7 (m, 2H), 1.5 (m, 2H).

6-(4-[3-Methyl-2,3-dihydro(benzo-1,3-thiazole)-2-methyliden]-1-quinolinium)-hexanoic acid N-hydroxysuccinimide ester (16). To a solution of 6-(4-[3-methyl-2,3-dihydro-(benzo-1,3-thiazole)-2-methylidene]-1-quinolinium)-hexanoic acid (2 g, 5 mmol) in N,N-dimethyl formamide (150 mL) was added 1,3-dicyclohexylcarbodiimide (3.2 g, 15.4 mmol) and N-hydroxysuccinimide (1.76 g, 15.4 mmol). The red turbid solution was stirred for 2 days at room temperature. After evaporation of the solvent the remaining residue was re-dissolved in 100 mL CH$_2$Cl$_2$ and filtered. The filtrate was concentrated to approximately 15 mL and precipitated in diethyl ether (500 mL). The 89.1% pure (HPLC) product was isolated as a red solid (2.9 g). $^1$H-NMR (300 MHz, d$_6$-DMSO): δ 8.8 (d, 1H), 8.65 (d, 1H), 8.15 (d, 1H), 8.05 (dd, 2H), 7.8 (dd, 2H), 7.6 (t, 1H), 7.4 (dd, 2H), 6.95 (s, 1H), 4.6 (t, 2H), 4.0 (s, 3H), 2.8 (s, 4H), 2.7 (t, 2H), 1.9 (m, 2H), 1.7 (m, 2H); 1.5 (m, 2H).

Example 9

Procedure for the Preparation of the Doubly Labeled Probes of Formula (17)

A linker-conjugated oligonucleotide (10 nmol) prepared according to the method described in Example 6 was dissolved in 10–20 µL of water. Sodium phosphate buffer (25 µL, 100 mM, pH 7) and solutions of an NHS ester functionalized dye in N,N-dimethylformamide (2.5 µL, 40 mM, tenfold molar excess) and a maleimide functionalized dye in N,N-dimethyl-formamide (2.5 µL, 40 mM, tenfold excess) were added. The volume of the reaction mixture was adjusted to 50 µL with water and the solution was incubated for 3 h at 37° C. The resulting product solution was stored at –20° C.

Alternatively the labeling reaction was performed using the following two separate steps:

1. A linker-conjugated oligonucleotide (10 nmol) prepared according to Example 6 was dissolved in 10–20 µL water. Sodium borate buffer (25 µL, 50 mM, pH 8.5) and a solution of an NHS ester functionalized dye in N,N-dimethylformamide (2.5 µL, 40 mM, tenfold molar excess) were added. The volume was adjusted to 50 µL with water and the solution was incubated for 3 h at 37° C. The mixture was concentrated to dryness in a vacuum centrifuge.

2. The singly labeled oligonucleotide from step 1 was dissolved in 10–20 µL water. Sodium phosphate buffer (25 µL, 100 mM, pH 5.5) and a solution of a maleimide functionalized dye in N,N-dimethylformamide (2.5 µL, 40 mM, tenfold excess) were added. The volume was adjusted to 50 µL with water and the solution was incubated for 3 h at 37° C. The resulting product solution was stored at –20° C.

The doubly labeled oligonucleotides were purified by gel electrophoresis (16% acrylamide, 7 M urea; 1.5 mm×40 cm×21 cm; constant power of 55 Watt). After completion of the electrophoresis the product bands were visualized by UV-shadowing and gel slices that contained the major product bands were cut out. The doubly labeled oligonucleotides were extracted from the gel slices with 0.5 mL water at 60° C. three times. The solutions containing the labeled oligonucleotides were concentrated in vacuo and subjected to ultracentrifugation with a 4 KDa cut-off. Followed by dilution in water and OD measurement the concentration of the oligonucleotide product solution was adjusted to 10 µM.

Examples of doubly labeled oligonucleotide probes that were prepared according to this procedure are listed in Table 1, compounds (17.1)–(17.33). The ethidium derivative (15) was used in all reactions where ethidium is attached to the oligonucleotide and the thiazole orange (TO) derivative (16) was used in all reactions where TO is attached to the oligonucleotide. The derivatives of ethidium and thiazole orange were prepared as described in Example 7 and Example 8. All other dye derivatives were purchased either from Molecular Probes Inc. (Eugene, Oreg., USA) or from Sigma-Aldrich Corp. (St. Louis, Mo., USA) and the abbreviations for the dyes are used in accordance with the catalogue of the supplier. One letter abbreviations of nucleotides that are printed in bold stand for LNA (locked nucleic acid) nucleotides.

The employed fluorescent dyes that were functionalized as an NHS ester or as a maleimide were the following:
Purchased from Molecular Probes, Inc. (Eugene, Oreg., USA):
5(6)-TAMRA-NHS (5-(and 6-)carboxytetramethylrhodamine succinimidyl ester)
5(6)-FAM-NHS (5-(and 6-)carboxyfluorescein succinimidyl ester)
7-QSY-NHS (carboxy-QSY-7-succinimidyl ester)
5-TAMRA-M (tetramethylrhodamine-5-maleimide)
7-QSY-M (QSY-7-maleimide)
Texas Red-M (Texas Red $C_2$ maleimide)
MDCC-M (7-diethylamino-3-((((2-maleimidyl)ethyl)amino)carbonyl)coumarin)
Purchased from Sigma-Aldrich Corp. (St. Louis, Mo., USA):
5-FAM-M (fluorescein-5-maleimide)

Doubly labeled oligonucleotide probes (17.1) to (17.33) were characterized by MALDI-TOF mass spectroscopy with a Biflex™ III (Bruker Daltonics Inc., Billerica, Mass., USA) instrument. The calculated and observed m/z ratios are listed in Table 2.

TABLE 2

Mass spectroscopic analysis of doubly labeled probes

| Doubly labeled probe | m/z calculated | m/z observed |
|---|---|---|
| (17.1) | 7687.9 | 7674.0 |
| (17.2) | 7404.5 | 7403.0 |
| (17.3) | 8230.3 | 8224.5 |
| (17.4) | 7947.8 | 7938.9 |
| (17.5) | 8026.9 | 8020.1 |
| (17.6) | 7975.8 | 7976.2 |
| (17.7) | 8258.3 | 8255.9 |
| (17.8) | 8054.6 | 8057.2 |
| (17.9) | 9470.8 | 9469.4 |
| (17.10) | 9495.8 | 9494.0 |
| (17.11) | 9812.4 | 9797.3 |
| (17.13) | 9498.5 | 9497.1 |
| (17.14) | 9718.2 | 9695.7 |
| (17.16) | 9400.4 | 9397.9 |
| (17.17) | 7895.8 | 7890.6 |
| (17.19) | 8240.1 | 8242.8 |
| (17.20) | 8541.6 | 8527.3 |
| (17.21) | 8196.1 | 8192.1 |
| (17.22) | 9551.83 | 9539.3 |
| (17.24) | 8967.1 | 8966.9 |
| (17.25) | 9011.1 | 9011.9 |
| (17.26) | 9065.2 | 9061 |
| (17.27) | 9336.3 | 9341.6 |
| (17.28) | 9202.9 | 9204 |
| (17.29) | 9246.9 | 9245.5 |
| (17.30) | 9301 | 9294.7 |
| (17.31) | 10694.8 | 10698.9 |
| (17.32) | 11008 | 11011.1 |
| (17.33) | 8607 | 8611.3 |

Example 10

Measurement of the Fluorescence of the Nucleic Acid Probe (17.2) in the Presence and Absence of a Complementary Sequence as a Function of Temperature The experiments were performed on a LIGHTCYCLER™ instrument (Roche Diagnostics, Indianapolis, Ind., USA). Either probe (17.2) (d(T)$_{20}$ with the covalently attached dyes fluorescein and ethidium, see Table 1, 0.5 µM) or a mixture of probe (17.2) (0.5 µM) with the complementary oligonucleotide d(A$_{20}$G) were employed. 20 µL of a solution containing the corresponding oligonucleotides in a PCR buffer (50 mM Tris/HCL, 10 mM KCl, 5 mM (NH$_4$)$_2$SO$_4$, 4 mM MgCl$_2$, pH 8.3 at 25° C.) were subjected to the following temperature program:
1. 95° C. for 5 min
2. cool down to 40° C. at 20° C. per second
3. heat up to 90° C. at 0.1° C. per second
4. cool down to 40° C. at 0.1° C. per second
5. repeat steps 3 and 4 two times During steps 3 and 4, the relative fluorescence intensity at 530 nm and 640 nm were recorded with irradiation of the solution at the excitation wavelength 470 nm. The averaged data are depicted in FIG. 14, curves A, A', B and B'.

Example 11

Measurement of the Fluorescence of the Nucleic Acid Probes (17.11), (17.20), and (17.21) in the Presence and Absence of a Complementary Sequence as a Function of Temperature The experiments were performed on a SPEX FLUOROMAX™-3 fluorescence spectrometer (Horiba Instruments, Inc., Calif., USA). The slit widths of both the emission and the excitation monochromator were adjusted to 2 nm. For all probes the oligonucleotide 5'-d(AGGGTGGACTTGAAGATGAGCGAAAAA)-3' (SEQ ID NO:) was employed as the complementary sequence. 200 μL of a solution containing either the nucleic acid probe (0.5 μM) or the nucleic acid probe with its complementary sequence (probe 0.5 μM, complementary sequence 5 μM) in a PCR buffer (50 mM Tris/HCL, 10 mM KCl, 5 mM (NH$_4$)$_2$SO$_4$, 4 mM MgCl$_2$, pH 8.3 at 25° C.) were subjected to the following temperature program:

The fluorescence emission intensities were determined by averaging over the data recorded successively four times at each 5° C. step of temperature increase. The respective excitation and emission wavelengths were 510/528 nm for probe (17.11), 510/625 nm for probe (17.20) and both 420/528 nm and 510/528 nm for probe (17.21) For each of the probes the fluorescence emission intensities observed with and without the presence of the complementary sequence ($I_F^{hyb}$ and $I_F^{free}$) and additionally the ratio $I_F^{hyb}/I_F^{free}$ of the fluorescence intensities with and without the presence of the complementary sequence are displayed as a function of temperature in FIG. 15 (probe (17.11)), FIG. 16 (probe (17.20)), FIG. 17 (probe (17.21) with excitation/emission at 510/528 nm) and FIG. 18 (probe (17.21) with excitation/emission at 420/528 nm).

Example 12

Stability of the Nucleic Acid Probe (17.13) Under PCR Conditions

The nucleic acid probe (17.13) (5'-d(TTTTTCGCTCATCTTCAAGTCCACCCG)-3' (SEQ ID NO:5) with the covalently attached dyes TAMRA and thiazole orange), see Table 1, 4 nmol) was dissolved in 430 μL PCR buffer (Tris/HCl (50 mM, pH 8.3). KCl (10 mM), (NH$_4$)$_2$SO$_4$ (5 mM). MuCl$_2$ (2 mM)) in the presence of 17.5 units of FastStartTaq DNA-Polymerase (Roche Diagnostics, Indianapolis, Ind, USA). 50% of the solution of the oligonucleotide was used as a reference sample. The reference sample was concentrated to dryness in a vacuum centrifuge and the residue was reconstituted in 20 μL 0.1 M TEAA buffer pH 7.0 with 5% acetonitrile. The resulting solution was injected in an analytical HPLC system and the oligonucleotide was analyzed at a flow rate of 1.0 mL/minute with a gradient elution of 5% to 100% acetonitrile in 0.1M TEAA buffer pH 7.0 for 15 minutes, followed by elution with 100% acetonitrile for 10 minutes on a C18 reversed phase column. The oligonucleotide eluted with a retention time of 21.5 and was approximately 80% pure by integration at 260 nm. The remaining solution of the oligonucleotide in PCR buffer was subjected to 40 temperature cycles ma PCR machine (1 minute 94° C., 1 minute 66° C., 1 minute 72° C.), concentrated to dryness and analyzed as described for the reference sample. The oligonucleotide was approximately 80% pure by integration at 260 nm and had an impurity profile that was virtually indistinguishable from the impurity profile of the reference sample.

Example 13

PCR with Doubly Labeled Nucleic Acid Probes and Human Genomic DNA

The experiments summarized in Table 3, below were performed on a MINICYCLER™ TTC-150 thermal cycler (MJ Research, Inc., Reno, Nev., USA). The PCR reactions were set up in a total volume of 25 μL with each tube containing Tris/HCl buffer (50 mM, pH 8.3), KCl(10 mM), (NH$_4$)$_2$SO$_4$ (5 mM), MgCl$_2$ (2 mM), the deoxynucleotide triphosphates dATP, dGTP, dCTP and dTTP (200 μM each), primers 1 and 2 according to table 3 (250 nM), human genomic DNA (10 ng), FastStartTaq DNA-Polymerase (1 unit, Roche Diagnostics, Indianapolis, Ind., USA) and BSA (0.5 mg/mL). The reactions were initiated at 94° C. for 10 minutes, followed by 30 cycles of denaturation at 94° C. for 1 minute, annealing at 66° C. for 1 minute, and elongation at 72° C. for 1 minute. Finally the reaction was kept at 72° C. for 7 minutes. The PCR products were analyzed by agarose gel electrophoresis and the corresponding PCR products were detected by staining with SYBR Gold (Molecular probes, Eugene, Oreg., USA). Specific PCR products of the expected length were obtained and all cases.

TABLE 3

PCR with doubly labeled probes and human genomic DNA

| Primer 1 [1] | Dye 1 | Dye 2 | 5'-Modification | Primer 2 [2] | Gene [3] | Amplicon |
|---|---|---|---|---|---|---|
| (17.4) | 5(6)-FAM | Ethidium | (14) | (22) | ADA | 254 bp |
| (17.15) | TO | MDCC | (14) | (22) | ADA | 259 bp |
| (17.16) | TO | MDCC | (14) | (22) | ADA | 259 bp |
| (17.21) | TO | MDCC | HEG/(14) | (22) | ADA | 254 bp |
| (17.24) | TO | MDCC | (14) | (23) | Prothrombin | 218 bp |
| (17.28) | TO | MDCC | (14) | (24) | TCRβ | 372 bp |

[1] Nucleic acid probes (17.15), (17.16) and (17.24) contain a 5'-leading sequence d(T)$_5$ that is not part of the corresponding gene.

[2] Primer (22) = 5'-d(GCT-CAA-CAC-AAA-GAT-GTC-TTC-TCT-GTG)3' (SEQ ID NO:13)

Primer (23) = 5'-d(GGG-TGA-AGG-CTG-TGA-CCG)-3' (SEQ ID NO 14)

Primer (24) = 5'-d(GGG-TGA-AGG-CTG-TGA-CCG)-3' (SEQ ID NO.14)

[3] Female human genomic DNA from Promega GmbH (Mannheim, Germany, catalogue no. G1521) was employed in all reactions except for the reaction with the nucleic acid probe (17.16) that represents an allele-specific primer for a single nucleotide polymorphism in the adenine deaminase (ADA) gene with a T to G substitution at position 1006, human genomic DNA from the Coriell Institute (Camden, NJ, USA) that was heterozygous with respect to the polymorphism was employed with probe (17.16)

Example 14

Real-Time PCR with the Nucleic Acid Probes (17.14), (17.21) and (17.24)

The experiments were performed with an "ICYCLER™ iQ" PCR machine (Bio-Rad Laboratories, Inc., USA). The PCR reactions were set up in a total volume of 25 μL containing Tris/HCl buffer(50 mM, pH 8.3), KCl (10 mM), $(NH_4)_2SO_4$ (5 mM), $MgCl_2$ (2 mM), the deoxynucleotide triphosphates dATP, dGTP, dCTP and dTTP (200 μM each), one of the nucleic acid probes (17.14), (17.21) or (17.24) as the first primer (800 nM), a second primer (primer (22)=5'-d(GCT-CAA-CAC-AAA-GAT-GTC-TTC-TCT-GTG)-3' (SEQ ID NO:) with probes (17.14) and (17.21), and primer (23)=5'-d(GGG-TGA-AGG-CTG-TGA-CCG)-3' (SEQ ID NO:) with probe (17.24), 800 nM), FastStartTaq DNA-Polymerase (1 unit, Roche Diagnostics, Indianapolis, Ind., USA) and BSA (0.5 mg/mL). An aliquot of a PCR product that was prepared according to Example 13, was employed as the template in each reaction. The reaptions with the probes (17.14) and (17.21) contained approximately 0.1% of the 254 bp or 259 bp PCR product that corresponds to a part of the human adenine deaminase (ADA) gene and the reaction with the probe (17.24) contained approximately 0.1% of the 218 bp PCR product that corresponds to a part of the human prothrombin gene. A filter set corresponding to an excitation wavelength of 490 nm and an emission wavelength of 530 nm was employed with the probes (17.21) and (17.24) and a filter set corresponding to an excitation wavelength of 490 nm and and emission wavelength of 625 nm was employed with the probe (17.14).

The reactions were initiated with 10 minutes at 94° C., followed by 30 cycles of denaturation at 94° C. for 1 minute, annealing at 66° C. for 1 minute, and elongation at 72° C. for 1 minute. Finally the reactions were kept at 72° C. for 7 minutes. The fluorescence emission intensities as a function of the cycle number that were observed with the nucleic acid probes (17.21) and (17.24) are depicted in FIG. 19 and FIG. 21. A nearly identical result was obtained with the nucleic acid probe (17.14). The PCR products were analyzed by agarose gel electrophoresis and the corresponding products with a length of 254 bp, 259 bp or 218 bp were detected by staining with SYBR Gold (Molecular probes, Eugene, Oreg., USA).

Example 15

Quantification of a Target Nucleic Acid with the Nucleic Acid Probe (17.21)

The experiments were performed with an "ICYCLER™ iQ" PCR machine (Bio-Rad Laboratories, Inc., USA). The PCR reactions were set up in a total volume of 25 μL containing Tris/HCl buffer (50 mM, pH 8.3), KCl (10 mM), $(NH_4)_2SO_4$ (5 mM), $MgCl_2$ (2 mM), the deoxynucleotide triphosphates dATP, dGTP, dCTP and dTTP (200 μM each), the primer (22) (5'-d(GCT-CAA-CAC-AAA-GAT-GTC-TTC-TCT-GTG)-3', (SEQ ID NO:) 800 nM), the nucleic acid probe (17.21) as the second primer (800 nM), FastStartTaq DNA-Polymerase (1 unit, Roche Diagnostics, Indianapolis, Ind., USA) and BSA (0.5 mg/mL). Aliquots of the 254 bp PCR product corresponding to the human adenine deaminase (ADA) gene that was prepared according to Example 13 were employed as the template in the reactions, Approximately 0.1%, 0.01%, 0.001% and 0.0001% of the PCR product was used. The reactions were performed in duplicate. A filter set corresponding to an excitation wavelength of 490 nm and an emission wavelength of 530 nm was employed.

The reactions were initiated with 10 minutes at 94° C., followed by 30 cycles of denaturation at 94° C. for 1 minute, annealing at 66° C. for 1 minute, and elongation at 72° C. for 1 minute. Finally the reactions were kept at 72° C. for 7 minutes. The observed fluorescence emission intensities as a function of the cycle number are depicted in FIG. 20. Curves A and B depict the observed fluorescence intensity where 0.1% of the total amount of a PCR product was employed as the template, curve C relates to a reaction where 0.01% of a PCR product was employed, curves D and E relate to reactions where 0.001% of a PCR product was employed, and curves F and G relate to reactions where 0.001% of a PCR product was employed. The PCR products were analyzed by agarose gel electrophoresis and the corresponding products with a length of 254 bp were detected by staining with SYBR Gold (Molecular probes, Eugene, Oreg., USA).

---

What is claimed is:

1. A method for the detection or quantification of a nucleic acid analyte comprising the steps of:
   a. providing a nucleic acid probe, wherein said nucleic acid probe is comprised of a nucleic acid that is derivatized with two or more non-identical covalently attached dyes, wherein at least one dye is fluorescent, and wherein at least one dye has a high affinity to double stranded nucleic acids, wherein the dyes are attached at either the same nucleotide of the nucleic probe or at nucleotides of the nucleic acid probe that are directly adjacent to each other;
   b. contacting said nucleic acid probe with a nucleic acid analyte so as to allow for the hybridization of the nucleic acid probe with the nucleic acid analyte; and
   c. detecting or quantifying said nucleic acid analyte by measuring the change in the fluorescence of the nucleic acid probe resulting from the specific interaction of at least one high affinity dye with the nucleic acid analyte upon the hybridization of the nucleic acid probe with the nucleic acid analyte.

2. The method of claim 1 wherein the dye that has a high affinity to double stranded nucleic acids is an intercalator.

3. The method of claim 1 wherein the dye that has a high affinity to double stranded nucleic acids is a groove binder.

4. The method of claim 1 wherein the nucleic acid probe comprises a fluorescent intercalator and a non-fluorescent quencher.

5. The method of claim 1 wherein the nucleic acid probe comprises a fluorescent intercalator and a second fluorescent dye wherein the second fluorescent dye functions as the donor of a FRET system formed between the intercalator and the second dye.

6. The method of claim 1 wherein the nucleic acid probe comprises a fluorescent intercalator and a second fluorescent dye wherein the second fluorescent dye functions as the acceptor of a FRET system formed between the intercalator and the second dye.

7. The method of claim 1 wherein the nucleic acid probe comprises a fluorescent intercalator and two dyes that form an excimer pair.

8. The method of claim 1 wherein the nucleic acid probe comprises a fluorescent intercalator and two dyes that form an exciplex pair.

9. The method of claim 1 wherein the nucleic acid probe comprises a fluorescent groove binder and a non-fluorescent quencher.

10. The method of claim 1 wherein the nucleic acid probe comprises a fluorescent groove binder and a second fluorescent dye wherein the second fluorescent dye functions as the donor of a FRET system formed between the fluorescent groove binder and the second dye.

11. The method of claim 1 wherein the nucleic acid probe comprises a fluorescent groove binder and a second fluorescent dye wherein the second fluorescent dye functions as the acceptor of a FRET system formed between the fluorescent groove binder and the second dye.

12. The method of claim 1 wherein the nucleic acid probe comprises a fluorescent groove binder and two dyes that form an excimer pair.

13. The method of claim 1 wherein the nucleic acid probe comprises a fluorescent groove binder and two dyes that form an exciplex pair.

14. The method of claim 1 carried out as a homogeneous assay to detect or quantify a nucleic acid analyte in a sample.

15. The method of claim 14 wherein the homogeneous assay is a polymerase chain reaction (PCR).

16. The method of claim 15 wherein the nucleic acid probe functions as a primer in the polymerase chain reaction, providing for a real-time detection or quantification of the amplification product.

17. The method of claim 15 wherein said nucleic acid probe functions as a hybridization probe in a polymerase chain reaction, providing for a real-time detection or quantification of the amplification product.

18. The method of claim 1 conducted in a multiplexed format.

19. The method of claim 18 performed by applying nucleic acid microarrays.

20. The method of claim 19 wherein the nucleic acid probe is provided on a microarray and the nucleic acid analyte is provided in solution.

21. The method of claim 20 wherein the nucleic acid analyte is hybridized to a microarray and the nucleic acid probe is brought into contact with the microarray.

22. A method for the detection or quantification of a nucleic acid analyte comprising the steps of:
   a. providing a nucleic acid probe, wherein said nucleic acid probe is comprised of a nucleic acid that is derivatized with two non-identical covalently attached dyes, of which at least one dye is fluorescent, and of which one dye is a pH-sensitive dye, wherein the dyes are attached at either the same nucleotide of the nucleic acid probe or at nucleotides of the nucleic acid probe that are directly adjacent to each other;
   b. contacting said nucleic acid probe with a nucleic acid analyte so as to allow for the hybridization of the nucleic acid probe with the nucleic acid analyte;
   c. removing the unhybridized nucleic acid probe from the mixture; and
   d. measuring the fluorescence of the hybridized nucleic acid probe under one or more conditions where the pH of the medium is defined.

23. The method of claim 22 wherein the nucleic acid analyte is hybridized to a microarray and the removal of the unhybridized nucleic acid probe is conducted by washing the microarray under conditions that leave the hybridized nucleic acid probe on the array.

24. The method of claim 22 wherein the pH-sensitive dye is selected from a substituted trityl group and wherein the covalent attachment of the substituted trityl group to the nucleic acid probe is provided through a linkage of one of the aromatic rings of the substituted trityl group to one of the nucleotides of the nucleic acid probe.

25. The method of claim 24 wherein the substituted trityl group is a derivative of the dimethoxytrityl group.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(20)

<400> SEQUENCE: 1
tttttttttt tttttttttt                                            20

<210> SEQ ID NO 2
<211> LENGTH: 22
<212> TYPE: DNA
<213> ORGANISM: Artificial
<220> FEATURE:
<223> OTHER INFORMATION: Synthetic Nucleic Acid Probe
<220> FEATURE:
```

-continued

```
<221> NAME/KEY: misc_feature
<222> LOCATION: (1)..(22)

<400> SEQUENCE: 2
cgctcatctt caagtccacc ct                                              22

<210> SEQ ID NO 3
<211> LENGTH: 22
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(22)

<400> SEQUENCE: 3
cgctcatctt caagtccacc cg                                              22

<210> SEQ ID NO 4
<211> LENGTH: 27
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(27)

<400> SEQUENCE: 4
tttttcgctc atcttcaagt ccaccct                                         27

<210> SEQ ID NO 5
<211> LENGTH: 27
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(27)

<400> SEQUENCE: 5
tttttcgctc atcttcaagt ccacccg                                         27

<210> SEQ ID NO 6
<211> LENGTH: 25
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(25)

<400> SEQUENCE: 6
tttttcactg ggagcattga ggctc                                           25

<210> SEQ ID NO 7
<211> LENGTH: 26
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(26)

<400> SEQUENCE: 7
```

```
attctcaact ctgactgtga gcaaca                                    26

<210> SEQ ID NO 8
<211> LENGTH: 30
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(30)

<400> SEQUENCE: 8
aactcctctt cagtaaagcc catgtcccgt                                30

<210> SEQ ID NO 9
<211> LENGTH: 31
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(31)

<400> SEQUENCE: 9
aaactcctct tcagtaaagc ccatgtcccg t                              31

<210> SEQ ID NO 10
<211> LENGTH: 23
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(23)

<400> SEQUENCE: 10
ttcagtaaag cccatgtccc gtt                                       23

<210> SEQ ID NO 11
<211> LENGTH: 27
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(27)

<400> SEQUENCE: 11
agggtggact tgtgaaagag cgaaaaa                                   27

<210> SEQ ID NO 12
<211> LENGTH: 25
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(25)

<400> SEQUENCE: 12
ccactatcct tcgcaagacc cttcc                                     25
```

```
<210> SEQ ID NO 13
<211> LENGTH: 27
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(27)

<400> SEQUENCE: 13
gctcaacaca aagatgtctt ctctgtg                                    27

<210> SEQ ID NO 14
<211> LENGTH: 18
<212> TYPE: DNA
<213> ORGANISM: Artificial
<220> FEATURE:
<223> OTHER INFORMATION: Synthetic Nucleic Acid Probe
<220> FEATURE:
<221> NAME/KEY: misc_feature
<222> LOCATION: (1)..(18)

<400> SEQUENCE: 14
gggtgaaggc tgtgaccg                                              18
```